United States Patent
Steenstrup et al.

(10) Patent No.: US 8,158,771 B2
(45) Date of Patent: Apr. 17, 2012

(54) HOST CELL PROTEIN KNOCK-OUT CELLS FOR PRODUCTION OF THERAPEUTIC PROTEINS

(75) Inventors: Thomas Dock Steenstrup, Gentofte (DK); Peder Lisby Norby, Copenhagen O (DK)

(73) Assignee: Novo Nordisk Health Care AG, Zurich (CH)

( * ) Notice: Subject to any disclaimer, the term of this patent is extended or adjusted under 35 U.S.C. 154(b) by 253 days.

(21) Appl. No.: 12/700,324

(22) Filed: Feb. 4, 2010

(65) Prior Publication Data
US 2010/0137570 A1 Jun. 3, 2010

Related U.S. Application Data

(62) Division of application No. 11/995,109, filed as application No. PCT/EP2006/064220 on Jul. 13, 2006, now Pat. No. 7,696,318.

(60) Provisional application No. 60/706,369, filed on Aug. 8, 2005.

(30) Foreign Application Priority Data

Jul. 13, 2005  (EP) ..................................... 05106401

(51) Int. Cl.
C12Q 1/68 (2006.01)
C12P 19/34 (2006.01)
C07H 21/02 (2006.01)
C07H 21/04 (2006.01)

(52) U.S. Cl. ..... 536/24.31; 435/6; 435/91.1; 435/91.31; 536/23.1

(58) Field of Classification Search ............. 435/6, 91.1, 435/91.31; 536/23.1, 24.31
See application file for complete search history.

*Primary Examiner* — Jane Zara
(74) *Attorney, Agent, or Firm* — Rosemarie R. Wilk-Orescan

(57) ABSTRACT

The present invention relates to methods and means for making Vitamin K-dependent protein compositions which are devoid or substantially devoid of protein contaminants. In particular, methods and means useful for the reduction or elimination of protein contaminants also being Vitamin K-dependent proteins are described.

2 Claims, 6 Drawing Sheets

FIGURE 3
A)
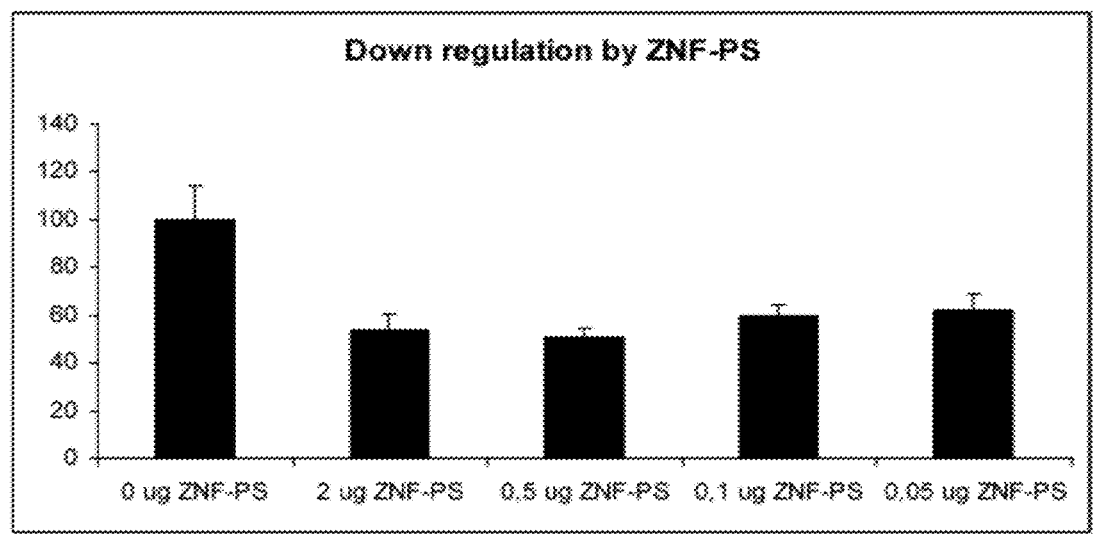
B)
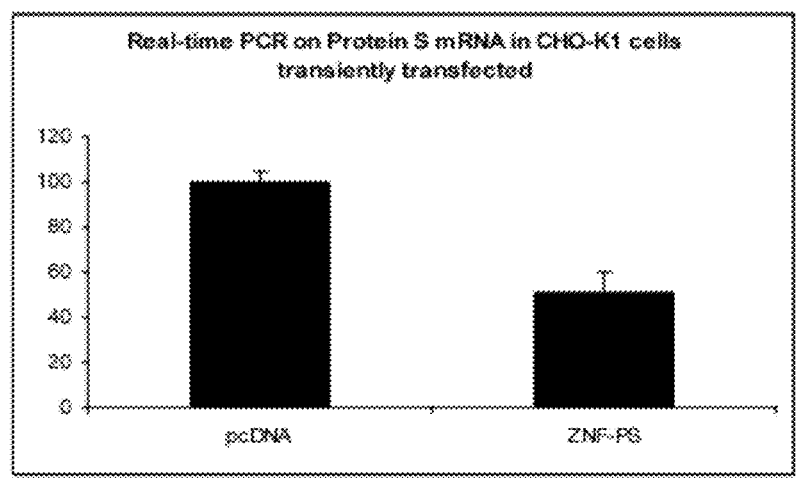

SEQUENCE LISTING

<160> NUMBER OF SEQ ID NOS: 52

<210> SEQ ID NO 1
<211> LENGTH: 23
<212> TYPE: DNA
<213> ORGANISM: Artificial
<220> FEATURE:
<223> OTHER INFORMATION: Synthetic DNA primer

<400> SEQUENCE: 1
gcccaggctc gcagctcctc tgg                                           23

<210> SEQ ID NO 2
<211> LENGTH: 23
<212> TYPE: DNA
<213> ORGANISM: Artificial
<220> FEATURE:
<223> OTHER INFORMATION: Synthetic DNA primer

<400> SEQUENCE: 2
caggtgacac ctgccagctg gtg                                           23

<210> SEQ ID NO 3
<211> LENGTH: 2306
<212> TYPE: DNA
<213> ORGANISM: Artificial
<220> FEATURE:
<223> OTHER INFORMATION: CHO Protein S cDNA sequence

<400> SEQUENCE: 3
gcccaggctc gcagctcctc tgggcggagc gccggctcgg tccccgctgc gccagccgtg     60
atccccggca gcctgctcag caatgagggt cctgagcgcg cgctgtcggc tactgctggt    120
atgcctagcc ctggtgctgc cagcctcgga caaactttt ttgtcaaaag aacatgcctc     180
gcaagtcctg gtgaggaagc gccgcgcaaa taccttgctt gaagaaacta aaagggcaa     240
tcttgaaaga gaatgcatcg aagagctctg caataaagag gaagccaggg aggtctttga    300
aaacaatccc gaaacggatt attttttatcc aaaatatttg ggttgtctgg gcatgttccg    360
tgctggcctg ttcagtgctg cgcggcagtc tgttaatgct taccccgacc tcaggagctg    420
tgtcaatgcc atcccagacc aatgtgatcc tatgccatgc aatgaagatg ggtatctgag    480
ctgcaaagat ggccaagctg cttttcacatg catctgcaaa ccaggatggc aaggggacaa    540
atgccagttt gatgtaaatg aatgtaaaga tccttaaat gtaatgggg gctgcagcca       600
gatttgtgac aacactcctg gaagttacca ctgctcctgc agaagtggct ttgctatgct    660
ttcaaacaaa aaagactgca agatgtgga tgaatgctct atgaagccca gtgtttgtgg     720
ctcagctgtg tgcaagaaca ctccaggaga ctatgagtgt gaatgtcctg acggctacag    780
atatgatccc tcatcgaagt cttgcaaaga tgtggacgaa tgctctgaga catgtgtgc     840
tcaattgtgt gtcaattacc ctggaggcta ctcttgttac tgtgatggaa agaaaggatt    900
caagcttgcc caagatcaga gagttgtga gggtattcca gtgtgccttc ccttgaacct    960
tgacaaaaat tatgaattat tgtacttggc tgagcagttt gtaggagttg tcttatatct   1020
gaaatttcgt ttgccagaaa ttaccagatt ttcagctgaa tttgatttc ggacatatga    1080
ttcagagggc atcatcctgt atgcagaatc tcttgatcac tcaaattggc tcctgattgc    1140
acttcgtgat ggaaaaattg aagttcagtt taagaatgag ttttcaaccc aaatcacaac    1200
cggaggcaat gttattaaca atggtaaatg gaacatggta tccgtggaag aattagacga    1260

```
cagtgttagc attaaaatag ctaaagaagc tgtgatgaat ataaataaat tgggagcct     1320 ctttaaacct acagatggat ttctggacac caaaatatac tttgcaggat tacctcgggt     1380
agtggaaagt gcactcatta aaccgattaa ccctcgtctg gatggatgta tacgaggctg     1440
gaacttgatg aaacaaggag ctttaggtgc aaaggaaatt attcaaggaa aacaaaataa     1500
gcattgcttc ctcatggtgg agaagggctc ctactaccct ggttctggaa ttgctcggtt     1560
cagcatagat tacaataatg taaccaatgc agagggctgg caaataaatg tgaccttgaa     1620
tattcgtcca tccactggca ctggaattat gcttgccttg gtttctggag acaaagtgcc     1680
cttgtgcttg tccttggtgg gctccagctc tgaaaattct caggatattg tggtatttgt     1740
tgaaaattca gtggtggctc gaatggaggc cataactctg tgttctgacc agcaatccca     1800
actgaaatgt aatgttaaca gacatggcct agagctatgg agcccactga gaaagatgt     1860 catctactct aaagatattc aaggacaact agcagtcttg gacaaagcaa tgaaaggaaa     1920
cgtggccact tatctgggtg gcattccaga tctttccttc agtgccacgc cagtgaatgc     1980
cttctacagt ggctgcatgg aagtgaacat caacggggtg cagttggatc tggatgaagc     2040
catttctaaa cataatgaca tcagagctca ctcatgtcct tcagttaaga aaatccagaa     2100
gaacgtctaa tgtctgtttt ctgtgcttat aatgccccct tccttgtaat tatgctcacg     2160
cccctatcac cagctggcag gtgtcacctg tgaagtgcaa tgtttgaaat gatgtggtac     2220
tttgtccttc agattttgt tatataaacc acgtttttt tttttttta aagtctttct     2280 tctattgctg tctagaaatt aaataa                                           2306

<210> SEQ ID NO 4
<211> LENGTH: 2028
<212> TYPE: DNA
<213> ORGANISM: Artificial
<220> FEATURE:
<223> OTHER INFORMATION: CHO Protein S coding sequence

<400> SEQUENCE: 4
atgagggtcc tgagcgcgcg ctgtcggcta ctgctggtat gcctagccct ggtgctgcca       60
gcctcggaga caaacttttt gtcaaaagaa catgcctcgc aagtcctggt gaggaagcgc      120
cgcgcaaata ccttgcttga agaaactaaa aagggcaatc ttgaaagaga atgcatcgaa      180
gagctctgca ataagaggaa gccaggagg tctttgaaaa caatcccga aacgactat         240 ttttatccaa aatattttggg ttgtctgggc atgttccgtg ctggcctgtt cagtgctgcg      300
cggcagtctg ttaatgctta cccccgacctc aggagctgtg tcaatgccat ccagaccaa      360 tgtgatccta tgccatgcaa tgaagatggg tatctgagct gcaaagatgg ccaagctgct      420
ttcacatgca tctgcaaacc aggatggcaa ggggacaaat gccagtttga tgtaaatgaa      480
tgtaaagatc ccttaaatgt aaatgggggc tgcagccaga tttgtgacaa cactcctgga      540
agttaccact gctcctgcag aagtggcttt gctatgcttt caaacaaaaa agactgcaaa      600
gatgtggatg aatgctctat gaagcccagt gtttgtggct cagctgtgtg caagaacact      660
ccaggagact atgagtgtga atgtcctgac ggctacagat atgatccctc atcgaagtct      720
tgcaaagatg tggacgaatg ctctgagaac atgtgtgctc aattgtgtgt caattaccct      780
ggaggctact cttgttactg tgatggaaag aaaggattca gcttgcccca agatcagaag      840
agttgtgagg gtattccagt gtgccttccc ttgaaccttg acaaaaatta tgaattattg      900
tacttggctg agcagtttgt aggagttgtc ttatatctga atttcgtttt gccagaaatt      960
accagatttt cagctgaatt tgatttttgg acatatgatt cagagggcat catcctgtat     1020
```

-continued

```
gcagaatctc ttgatcactc aaattggctc ctgattgcac ttcgtgatgg aaaaattgaa      1080
gttcagttta agaatgagtt ttcaacccaa atcacaaccg gaggcaatgt tattaacaat      1140
ggtaaatgga acatggtatc cgtggaagaa ttagacgaca gtgttagcat taaaatagct      1200
aaagaagctg tgatgaatat aaataaattt gggagcctct ttaaacctac agatggattt      1260
ctggacacca aaatatactt tgcaggatta cctcgggtag tggaaagtgc actcattaaa      1320
ccgattaacc ctcgtctgga tggatgtata cgaggctgga acttgatgaa acaaggagct      1380
ttaggtgcaa aggaaattat tcaaggaaaa caaaataagc attgcttcct catggtggag      1440
aagggctcct actaccctgg ttctggaatt gctcggttca gcatagatta caataatgta      1500
accaatgcag agggctggca aataaatgtg accttgaata ttcgtccatc cactggcact      1560
ggaattatgc ttgccttggt ttctggagac aaagtgccct ttgccttgtc cttggtgggc      1620
tccagctctg aaaattctca ggatattgtg gtatttgttg aaaattcagt ggtggctcga      1680
atggaggcca taactctgtg ttctgaccag caatcccaac tgaaatgtaa tgttaacaga      1740
catggcctag agctatggag cccactgaag aaagatgtca tctactctaa agatattcaa      1800
ggacaactag cagtcttgga caaagcaatg aaaggaaacg tggccactta tctgggtggc      1860
attccagatc tttccttcag tgccacgcca gtgaatgcct tctacagtgg ctgcatggaa      1920
gtgaacatca acggggtgca gttggatctg gatgaagcca tttctaaaca taatgacatc      1980
agagctcact catgtccttc agttaagaaa atccagaaga acgtctaa                  2028
```

<210> SEQ ID NO 5  
<211> LENGTH: 675  
<212> TYPE: PRT  
<213> ORGANISM: Artificial  
<220> FEATURE:  
<223> OTHER INFORMATION: CHO Protein S amino acid sequence

<400> SEQUENCE: 5

```
Met Arg Val Leu Ser Ala Arg Cys Arg Leu Leu Leu Val Cys Leu Ala
  1               5                  10                  15

Leu Val Leu Pro Ala Ser Glu Thr Asn Phe Leu Ser Lys Glu His Ala
             20                  25                  30

Ser Gln Val Leu Val Arg Lys Arg Ala Asn Thr Leu Leu Glu Glu
         35                  40                  45

Thr Lys Lys Gly Asn Leu Glu Arg Glu Cys Ile Glu Glu Leu Cys Asn
 50                  55                  60

Lys Glu Glu Ala Arg Glu Val Phe Glu Asn Pro Glu Thr Asp Tyr
 65                  70                  75                  80

Phe Tyr Pro Lys Tyr Leu Gly Cys Leu Gly Met Phe Arg Ala Gly Leu
                 85                  90                  95

Phe Ser Ala Ala Arg Gln Ser Val Asn Ala Tyr Pro Asp Leu Arg Ser
            100                 105                 110

Cys Val Asn Ala Ile Pro Asp Gln Cys Asp Pro Met Pro Cys Asn Glu
        115                 120                 125

Asp Gly Tyr Leu Ser Cys Lys Asp Gly Gln Ala Ala Phe Thr Cys Ile
    130                 135                 140

Cys Lys Pro Gly Trp Gln Gly Asp Lys Cys Gln Phe Asp Val Asn Glu
145                 150                 155                 160

Cys Lys Asp Pro Leu Asn Val Asn Gly Gly Cys Ser Gln Ile Cys Asp
                165                 170                 175

Asn Thr Pro Gly Ser Tyr His Cys Ser Cys Arg Ser Gly Phe Ala Met
            180                 185                 190
```

```
Leu Ser Asn Lys Lys Asp Cys Lys Asp Val Asp Glu Cys Ser Met Lys
            195                 200                 205

Pro Ser Val Cys Gly Ser Ala Val Cys Lys Asn Thr Pro Gly Asp Tyr
        210                 215                 220

Glu Cys Glu Cys Pro Asp Gly Tyr Arg Tyr Asp Pro Ser Ser Lys Ser
225                 230                 235                 240

Cys Lys Asp Val Asp Glu Cys Ser Glu Asn Met Cys Ala Gln Leu Cys
                245                 250                 255

Val Asn Tyr Pro Gly Gly Tyr Ser Cys Tyr Cys Asp Gly Lys Lys Gly
            260                 265                 270

Phe Lys Leu Ala Gln Asp Gln Lys Ser Cys Glu Gly Ile Pro Val Cys
        275                 280                 285

Leu Pro Leu Asn Leu Asp Lys Asn Tyr Glu Leu Leu Tyr Leu Ala Glu
        290                 295                 300

Gln Phe Val Gly Val Val Leu Tyr Leu Lys Phe Arg Leu Pro Glu Ile
305                 310                 315                 320

Thr Arg Phe Ser Ala Glu Phe Asp Phe Arg Thr Tyr Asp Ser Glu Gly
                325                 330                 335

Ile Ile Leu Tyr Ala Glu Ser Leu Asp His Ser Asn Trp Leu Leu Ile
            340                 345                 350

Ala Leu Arg Asp Gly Lys Ile Glu Val Gln Phe Lys Asn Glu Phe Ser
        355                 360                 365

Thr Gln Ile Thr Thr Gly Gly Asn Val Ile Asn Asn Gly Lys Trp Asn
        370                 375                 380

Met Val Ser Val Glu Glu Leu Asp Asp Ser Val Ser Ile Lys Ile Ala
385                 390                 395                 400

Lys Glu Ala Val Met Asn Ile Asn Lys Phe Gly Ser Leu Phe Lys Pro
                405                 410                 415

Thr Asp Gly Phe Leu Asp Thr Lys Ile Tyr Phe Ala Gly Leu Pro Arg
            420                 425                 430

Val Val Glu Ser Ala Leu Ile Lys Pro Ile Asn Pro Arg Leu Asp Gly
        435                 440                 445

Cys Ile Arg Gly Trp Asn Leu Met Lys Gln Gly Ala Leu Gly Ala Lys
450                 455                 460

Glu Ile Ile Gln Gly Lys Gln Asn Lys His Cys Phe Leu Met Val Glu
465                 470                 475                 480

Lys Gly Ser Tyr Tyr Pro Gly Ser Gly Ile Ala Arg Phe Ser Ile Asp
                485                 490                 495

Tyr Asn Asn Val Thr Asn Ala Glu Gly Trp Gln Ile Asn Val Thr Leu
            500                 505                 510

Asn Ile Arg Pro Ser Thr Gly Thr Gly Ile Met Leu Ala Leu Val Ser
        515                 520                 525

Gly Asp Lys Val Pro Phe Ala Leu Ser Leu Val Gly Ser Ser Ser Glu
        530                 535                 540

Asn Ser Gln Asp Ile Val Val Phe Val Glu Asn Ser Val Val Ala Arg
545                 550                 555                 560

Met Glu Ala Ile Thr Leu Cys Ser Asp Gln Ser Gln Leu Lys Cys
                565                 570                 575

Asn Val Asn Arg His Gly Leu Glu Leu Trp Ser Pro Leu Lys Lys Asp
            580                 585                 590

Val Ile Tyr Ser Lys Asp Ile Gln Gly Gln Leu Ala Val Leu Asp Lys
        595                 600                 605

Ala Met Lys Gly Asn Val Ala Thr Tyr Leu Gly Gly Ile Pro Asp Leu
        610                 615                 620
```

```
Ser Phe Ser Ala Thr Pro Val Asn Ala Phe Tyr Ser Gly Cys Met Glu
625                 630                 635                 640

Val Asn Ile Asn Gly Val Gln Leu Asp Leu Asp Glu Ala Ile Ser Lys
            645                 650                 655

His Asn Asp Ile Arg Ala His Ser Cys Pro Ser Val Lys Lys Ile Gln
        660                 665                 670

Lys Asn Val
        675

<210> SEQ ID NO 6
<211> LENGTH: 21
<212> TYPE: DNA
<213> ORGANISM: Artificial
<220> FEATURE:
<223> OTHER INFORMATION: SiRNA target sequence
<220> FEATURE:
<221> NAME/KEY: misc_feature
<222> LOCATION: (3)..(19)
<223> OTHER INFORMATION: n is a, c, g, or t

<400> SEQUENCE: 6
agnnnnnnnn nnnnnnnnnc t                                          21

<210> SEQ ID NO 7
<211> LENGTH: 21
<212> TYPE: DNA
<213> ORGANISM: Artificial
<220> FEATURE:
<223> OTHER INFORMATION: Synthetic DNA sequence

<400> SEQUENCE: 7
agtgtgaatg tcctgacggc t                                          21

<210> SEQ ID NO 8
<211> LENGTH: 37
<212> TYPE: DNA
<213> ORGANISM: Artificial
<220> FEATURE:
<223> OTHER INFORMATION: Synthetic DNA sequence

<400> SEQUENCE: 8
gatctaaaaa agtgtgaatg tcctgacggc tttttta                         37

<210> SEQ ID NO 9
<211> LENGTH: 37
<212> TYPE: DNA
<213> ORGANISM: Artificial
<220> FEATURE:
<223> OTHER INFORMATION: Synthetic DNA sequence

<400> SEQUENCE: 9
gatctaaaaa agccgtcagg acattcacac tttttta                         37

<210> SEQ ID NO 10
<211> LENGTH: 21
<212> TYPE: DNA
<213> ORGANISM: Artificial
<220> FEATURE:
<223> OTHER INFORMATION: Synthetic DNA sequence

<400> SEQUENCE: 10
agctgcaaag atggccaagc t                                          21

<210> SEQ ID NO 11
<211> LENGTH: 37
```

```
<212> TYPE: DNA
<213> ORGANISM: Artificial
<220> FEATURE:
<223> OTHER INFORMATION: Synthetic DNA sequence

<400> SEQUENCE: 11
gatctaaaaa agctgcaaag atggccaagc tttttta                              37

<210> SEQ ID NO 12
<211> LENGTH: 37
<212> TYPE: DNA
<213> ORGANISM: Artificial
<220> FEATURE:
<223> OTHER INFORMATION: Synthetic DNA sequence

<400> SEQUENCE: 12
gatctaaaaa agcttggcca tctttgcagc tttttta                              37

<210> SEQ ID NO 13
<211> LENGTH: 21
<212> TYPE: DNA
<213> ORGANISM: Artificial
<220> FEATURE:
<223> OTHER INFORMATION: Synthetic DNA sequence

<400> SEQUENCE: 13
agaacatgcc tcgcaagtcc t                                               21

<210> SEQ ID NO 14
<211> LENGTH: 37
<212> TYPE: DNA
<213> ORGANISM: Artificial
<220> FEATURE:
<223> OTHER INFORMATION: Synthetic DNA sequece

<400> SEQUENCE: 14
gatctaaaaa agaacatgcc tcgcaagtcc tttttta                              37

<210> SEQ ID NO 15
<211> LENGTH: 37
<212> TYPE: DNA
<213> ORGANISM: Artificial
<220> FEATURE:
<223> OTHER INFORMATION: Synthetic DNA sequence

<400> SEQUENCE: 15
gatctaaaaa aggacttgcg aggcatgttc tttttta                              37

<210> SEQ ID NO 16
<211> LENGTH: 21
<212> TYPE: DNA
<213> ORGANISM: Artificial
<220> FEATURE:
<223> OTHER INFORMATION: Synthetic DNA sequence

<400> SEQUENCE: 16
agaaactaaa aagggcaatc t                                               21

<210> SEQ ID NO 17
<211> LENGTH: 37
<212> TYPE: DNA
<213> ORGANISM: Artificial
<220> FEATURE:
<223> OTHER INFORMATION: Synthetic DNA sequence

<400> SEQUENCE: 17
gatctaaaaa agaaactaaa aagggcaatc tttttta                              37
```

```
<210> SEQ ID NO 18
<211> LENGTH: 37
<212> TYPE: DNA
<213> ORGANISM: Artificial
<220> FEATURE:
<223> OTHER INFORMATION: Synthetic DNA sequence

<400> SEQUENCE: 18
gatctaaaaa agattgccct ttttagtttc tttttta                              37

<210> SEQ ID NO 19
<211> LENGTH: 21
<212> TYPE: DNA
<213> ORGANISM: Artificial
<220> FEATURE:
<223> OTHER INFORMATION: Synthetic DNA sequence

<400> SEQUENCE: 19
agccagattt gtgacaacac t                                               21

<210> SEQ ID NO 20
<211> LENGTH: 37
<212> TYPE: DNA
<213> ORGANISM: Artificial
<220> FEATURE:
<223> OTHER INFORMATION: Synthetic DNA sequence

<400> SEQUENCE: 20
gatctaaaaa agccagattt gtgacaacac tttttta                              37

<210> SEQ ID NO 21
<211> LENGTH: 37
<212> TYPE: DNA
<213> ORGANISM: Artificial
<220> FEATURE:
<223> OTHER INFORMATION: Synthetic DNA sequence

<400> SEQUENCE: 21
gatctaaaaa agtgttgtca caaatctggc tttttta                              37

<210> SEQ ID NO 22
<211> LENGTH: 25
<212> TYPE: PRT
<213> ORGANISM: Artificial
<220> FEATURE:
<223> OTHER INFORMATION: Artificial construct

<400> SEQUENCE: 22

Met Arg Val Leu Ser Val Arg Cys Arg Leu Leu Leu Val Cys Leu Ala
1               5                   10                  15
Leu Val Leu Pro Ala Ser Glu Thr Asn
            20                  25

<210> SEQ ID NO 23
<211> LENGTH: 24
<212> TYPE: DNA
<213> ORGANISM: Artificial
<220> FEATURE:
<223> OTHER INFORMATION: Synthetic DNA primer

<400> SEQUENCE: 23
ctgctggtat gcctagccct ggtg                                            24

<210> SEQ ID NO 24
<211> LENGTH: 24
```

```
<212> TYPE: DNA
<213> ORGANISM: Artificial
<220> FEATURE:
<223> OTHER INFORMATION: DNA primer

<400> SEQUENCE: 24
tgcagagctc ttcgatgcat tctc                                         24

<210> SEQ ID NO 25
<211> LENGTH: 24
<212> TYPE: DNA
<213> ORGANISM: Artificial
<220> FEATURE:
<223> OTHER INFORMATION: DNA primer

<400> SEQUENCE: 25
aagggcaatc ttgaaagaga atgc                                         24

<210> SEQ ID NO 26
<211> LENGTH: 25
<212> TYPE: DNA
<213> ORGANISM: Artificial
<220> FEATURE:
<223> OTHER INFORMATION: DNA primer

<400> SEQUENCE: 26
ccaaatattt tggataaaaa taatc                                        25

<210> SEQ ID NO 27
<211> LENGTH: 20
<212> TYPE: DNA
<213> ORGANISM: Artificial
<220> FEATURE:
<223> OTHER INFORMATION: DNA primer
<220> FEATURE:
<221> NAME/KEY: misc_feature
<222> LOCATION: (1)..(20)
<223> OTHER INFORMATION: n in position 3 is Adenosine or Guanosine

<400> SEQUENCE: 27
aancaacccc ttttgaccat                                              20

<210> SEQ ID NO 28
<211> LENGTH: 21
<212> TYPE: DNA
<213> ORGANISM: Artificial
<220> FEATURE:
<223> OTHER INFORMATION: DNA primer

<400> SEQUENCE: 28
cccagaggag ctgcgagcct g                                            21

<210> SEQ ID NO 29
<211> LENGTH: 1631
<212> TYPE: DNA
<213> ORGANISM: Artificial
<220> FEATURE:
<223> OTHER INFORMATION: immediately 5' to coding sequence

<400> SEQUENCE: 29
aarcaacccc ttttgaccat acacatttct actctttgtg tttgctggag ctgttttctc      60
cccacactca accccctttg ctgaagcctg gaacttgctt tccacagctt aagttgttat     120
aggtttcaat catctgtcca cctccctgac tttcataatt ttgtgaaata cccttgcata     180
tatatatggg actaaatatt attttctcct ggttgtccat aatagattaa tttaattcct     240
aaacaaagaa cagaacatag attggtatag tagaagagtt tcccttctcc ctactgcatg     300
```

```
aatggaaatt ccccaaacca tccttatcag agaaattaac tcacatacta gtcacctttc    360
attcagctgg atgacaaaat cattttaaaa aagagaata agaaaacag ataagaacaa       420 ctagatctag gaataatact taaaatatga ttctgcttag taggtttcat tcacacacct    480
agaaaaaaaa atcagtcaat gtttcctttg gcagaaaat gagcaataat gggtatgcat     540
tgaccactac tgttggacat agccttattg cttcatatag catctattca aagtctcaga   600
tcaacactat gaaaacctgt catctctgta ttagatgatg tgactggggc tgtaaagggt   660
aagctctttt cttacagcta tacaacaacg ctaagaccaa gttctgtgct ttgagcccag   720
gcagtttagt ttcccaggag caacctaaag cctgattcac aggcatatgt atgatccaaa   780
ctgaatggta gtacatcaat accaaaacaa tctattggtg aaacacacc ataggtgatc     840 gaaatactcc attttctttt cctctcatga cttctgttct gagcagtcct cttcctaaag   900
tctacattgt cttctgagtt caggctgaca tcttgacatc tcctggctg gcacagtctc     960 tggacaagga gggaagaagg agagaagggg aaagggagag gaggggggga gggagagaaa  1020
gaatgggaag aggaaggata tgaaagagag aagagaggag ggaaggcggg aggaagggag  1080
ggagggaggg agggagagag ggagagagag gagagagaga gagagagaga gagagagaga  1140
gagagagaga gagagagaga gagagaggga gagggagaga gagacagaga gagagagagg  1200
gagagggaga gagagagaga gagagagaga gagagagaga gagagagaga gtgaggagag  1260
agagagagag ttttcttcac cattggacat tcctaaagaa aagaagtaaa tgcaggattg  1320
gggacagtga cagaggacct ctgataaact ttctgaggcc tctgacctca ctctctcgga  1380
gccctcctcc accacccacc cccccctcc ctagctgaga aaagcttcca ggaaatgtcc   1440
cagtcatcgc ttcccctccc gggctggggg ctggagcgg gcggtcccct caggccaggg    1500
ctgctccggc cgcgctcggg cagggccaca acagagctgg gaaagctgag cccaggctcg  1560
cagctcctct gggcggagcg ccggctcggt ccccgctgcg ccagccgtga tccccggcag  1620
cctgctcagc a                                                         1631
```

<210> SEQ ID NO 30
<211> LENGTH: 75
<212> TYPE: DNA
<213> ORGANISM: Artificial
<220> FEATURE:
<223> OTHER INFORMATION: exon 1 in CHO Protein S

<400> SEQUENCE: 30

```
atgagggtcc tgagcgtacg ctgtcggcta ctgctggtat gcctagccct ggtgctgcca    60
gcctcggaga caaac                                                      75
```

<210> SEQ ID NO 31
<211> LENGTH: 4209
<212> TYPE: DNA
<213> ORGANISM: Artificial
<220> FEATURE:
<223> OTHER INFORMATION: Intron 1 in CHO Protein S
<220> FEATURE:
<221> NAME/KEY: misc_feature
<222> LOCATION: (2647)..(2652)
<223> OTHER INFORMATION: n is a, c, g, or t

<400> SEQUENCE: 31

```
tgtaagtaat ccatacctcc tggcttctcc attccctatg tgccccggct tgaagatttt    60
ccactaggct gtttgctgcc tcctaagttt ccagtaagtc cgccaccatt cagagagtcg   120
cggcagcctg ggtctggtgg gcagtgtaaa ggtgggacag gatcaaagct tgccttgctt   180
```

```
tgagaaccat tgtccacagg acttgattcc agaacccggg tgacactaag tgtcaaagga      240
attgcttgaa catagtccta aatattgcta ggaaagctaa gtcaagcctg ttgccctcct      300
cccgtttaca agagtgcccc agcccgcacc ctctcctgcg gctaaccttc cttttgcaat      360
ttctggactt tgaacttgat tgactggtct cacattgaca aactgtttgg ggactgctgg      420
ggtgttacat atgattctct aaccttgata taagaaatag ctgttggatg ttaccttgta      480
ccgaggatca ttttctgagg gttttgactg ttgccgcttt gagatggcag caagaattct      540
gtacaacaca cacattttg tgtttcttgg tctttcctct tcccattctc agattccggg       600
cagtatatcg agttttctct tagaaatata aaacgaacca caaggtttta gtacatttta      660
atggtcaatt aaattgtttt tagaagctta aatatgttca taattaacac tgctttcttt      720
tgctcttttg tagtcccagt cactggcatg ggagcaataa ctgtataaca aataccactt      780
aggtcactgc gagcaccaaa gaaacttttc aaagatggta attaagtagg agtttgctgg      840
aattgcaagt ttttattaat tagtaaggaa tctagcctga tattttaaa tgtctaacta      900 agttaaagac cagaatgaaa ctggttcact ttttattgag gataaacaag ttacagttat      960
aaagcctcaa caatcaaagc cctacgatga agcagcgtgt gactgtatgc acatgatcta    1020
tcttgttcag aggaacaatc aaacattttc agatagcatc agggcggtgg tggtactcgc    1080
ctataatcct agcaaagtca gaggcaagca gatctctgtg ttcaaggcca gcctagtcta    1140
cagagtgagt tccaggacaa ctggggctac acagagaaac ctgtctcaga gaaaaacaaa    1200
ataaaaccaa attcagatag ctggtgtttg ggaaaagagc aaaagacagc agtgctggcc    1260
acacagagag tagacaagtt cattctacaa ggacatcaca gaaagaatat gtgacccaat    1320
gacgaccata aactttcttg ttcctgtgtc aaattatctc cggtttattg atgaagaacc    1380
agacactatg agctgcgtct cctccttaag attttgtttt ggtgtcttgt ttttgtcaag    1440
gggtttcatt gtggccctga gcattagatc cagggctttg tgcatgctag gccagggagc    1500
tatattcccg aactccagaa gactaggaat ttgagatata aatagaattt gaattacctt    1560
ctgtacaatt gattgtatgg ttctagaaat attgctatat taagggaagc cttttgcagaa    1620 gacagttatt ttgagatggt gcataacaca aaagaaatga actaaagcct gaggcctgct    1680
ctgtagctct gccttgccct tagcctacaa taactttctt tacctttcaa gcatgtgcca    1740
ccacgcctga ctttcaggcc cttcatttta acaagaaagc aagtattcag ttatcaactg    1800
actttccaaa tgcatttgta tgaataaaaa ctacaaaaat ataaaataa gaactataca     1860 cacaaaagcc ttgtatttaa aatttacgct gtggacatat tttgctcatc attcgtgaga    1920
gcttgcggta aaaaggcaaa ggggaagagg aggatatcta ttttgggtag gctaatttgg    1980
ccttatccag acttcccttt tgggtggatg cagtctgccc agcacactat tggcccattt    2040
cttctacatg gctttgtgct ctgctctgcc cttagctaat tgtcccctt gacatgcttt      2100 tgtctttcct taaagtttct atacttcaaa aaccatcccg ctacactaat ggagtgattt    2160
tctcaagggt tgctttatgt ttggggtttg tactgcaaga gttagtttct gatatagcaa    2220
tggtgatagt atagtcttct accatgaact ctatgccagc aagtacaggg gtatatttca    2280
catgggtgtt ttctgttcac tgagtttcat gtcttctttg tatcttttg ttttgttttg     2340 tgagacaggg tttctctgta gcttttgagt cagtcctgga acttgctggc cggccttgaa    2400
ctcacagaga ttcacctgcc tctgcctccc aagtgctggg atttaaggtg tgagtcacca    2460
ctgccaggtt ttttctttgt atcttgagtg aactaaatag gtaagcttta aataataata    2520
tgagcagtct atttatatac attaaatatt aaatgcattg tgagatgagc atagcctttg    2580
```

```
aggcccagga acagaaagat ttacttcaca ttgtaaatat actggtatac atacaaacgt    2640
acatacnnnn nngtgtgtgt gtgtgtgtgt gtgtgtgtgt gcatgccata gcacacatgt    2700
gaagtccaga gtacagcatt ctcttttcct acctttctgt agattcttgt ggtcagagtc    2760
aggtcaaatc aaatcagaca gatgcatgta taaaatgctc ttacccactg aaccatcttg    2820
ctgcttggtc cacaagctta gtggaagaat gctgggaagt gaatagtatg ttttaaaatg    2880
tagttaacct tgacttttg ttgttgttgc tgttattgag gccacatttt cattgttctg    2940
agaaaatatt actattttcc tcagacagaa ttatatattt atttgaagtt catgaattcc    3000
atattatttt cctgtattta ttacaaatag catgcttaaa cacttccaag tagtgaaaca    3060
gctgctcatg taggacacgg attattgaca gtgctgccat ttatcagcca gtaatccact    3120
tggcaggtag cacgctcatc gttatccttt atgcacacaa agccttgttt gaattttatc    3180
ttttaatgag tgtcaatgaa atggaaagag ataagagtta aaatacaac ccaaactatt    3240 gtatttacat ttctctttta gaagaaacct aaagcagcat tacttcttgc ccatatttaa    3300
taaataacat catttacccct tgttccctgc ctccagactc tcccatatac tcctctttca    3360
attttattgg cccctttaaa tgacatatca ttacatgtat atccctacac ataagtataa    3420
ccagttcagt ttgtataatg ttacttgcat gtgtgttttc aatgctgatc atttggtagt    3480
ggataaccaa tggtgtgccc tatgaagggg cagagtattt gtatcatgct tagcattcct    3540
ttgttgactg taggattttg tttaaggttg aggtctcttg gtctttcccc tgtctgcttc    3600
tgcatgtcca tggccatcct tgttcagctc atgtttatgt agtcatgctg atgaggcttt    3660
atggatgtag cttctgacat tgctaagcaa cacagtctca gcaaactccc cagtcctctg    3720
gttcttacaa tctttccaca ctgtttcacc atgttgtctg agcctaggt gctgaagttg    3780 ttttgtgtct gtatccattg ggactaggct ccacatgtct gcattttgat tacttgtggt    3840
tttctgtaac ggtctctatg tgttgcaacg agaaggagta gttgctttga cgatgtgtaa    3900
agactatctt gtgggtataa ggacaaatat ttgcatgaag ctatggatta tgctggtctc    3960
aagcatgaac tggataaatt gtacagctca cacaaaacag ctatagctag ctgcacagtc    4020
aggcatgcac tgatctgctt ggggagttgt taaccaaagg gcttacatag ctatgtattt    4080
tctaagctct agttttacta tcacaaagaa aattaattca cccttaattg tttaataaga    4140
tgatatatct tagggaaaaa atgaaggtct ttttttgact tatataaaag cttatgtttt    4200
ctacagttt                                                            4209
```

<210> SEQ ID NO 32
<211> LENGTH: 155
<212> TYPE: DNA
<213> ORGANISM: Artificial
<220> FEATURE:
<223> OTHER INFORMATION: Exon 2 in CHO Protein S

<400> SEQUENCE: 32

```
tgtcaaaaga acatgcctcg caagtcctgg tgaggaagcg ccgcgcaaat accttgcttg     60
aagaaactaa aaagggcaat cttgaaagag aatgcatcga agagctctgc aataaagagg    120
aagccaggga ggtctttgaa aacaatcccg aaacg                                155
```

<210> SEQ ID NO 33
<211> LENGTH: 3239
<212> TYPE: DNA
<213> ORGANISM: Artificial
<220> FEATURE:
<223> OTHER INFORMATION: Intron 2 in CHO Protein S

<400> SEQUENCE: 33

```
gtaagagttc gtggaaatga ccaagtccac actcggatat atattggcag tcagaacact    60
gccagcttga gctaccttgc ttctgtttga aagctaatga cttaggagtt catttctcat   120
gtgttaccac tgacatttca ggcaggctgc caatgacagg cactccagcc aaactccatt   180
tcccttaagt ctcattactc gcaactagta tcgactttat aatgtgtgac tattttatta   240
tcctaaccaa atctggtagc cttgagggtg caagagaaga tgcgactgaa gggtaagtga   300
ccatatatgt acttgcattg tcactgtgct tttgttttgg ttgattgtgt ttgagacagt   360
ctcttactct gtagctccaa ctacaaggag ctccctatcc atctgctttg cttcagcct    420
cccaagtact gtgattatag actggtgtgt cttgccattt atctttaaga ggctctagat   480
agaaatgggg ccacctaact gagattagtc attacagcat tatgtatgct gactgtatac   540
tattctgtaa ccttcatgaa gtttcccgag gccactgata atcagcagta atcattagtg   600
tctaaaaatt tccaagttac ccacccgcca aacataacaa aaagacagca acatgggact   660
ctttgtccat tctgtgtttc aggagagggc aatttatagt atgcttgtaa ctaacaggag   720
tagcattaat atctccaagg agcactttga gcatgacctt gagagtctac atggaacact   780
gttcagggtc tcctcagatg ttctacctga gctgaattat acaatctgga ggaaaagaaa   840
gagatgacat acacaaggct cctcctttgc ctctgccaca gctcccagaa ccatgacaac   900
agctgagtga taaagagcaa ggactctttg tccatactta gaaaatttgt ccccaactgt   960
agctacttgt ggtctgtggt tgttattgta gctctttttt aatccctatg tgttctgata  1020
ggttcaaaga agaaattttc cccaaatatg caacaattaa attttaatct acctagaatt  1080
gagacaaaaa tgtgacgaaa taccttgatc aaaaaaacaa ctcaggagga aagggttttt  1140
tttttttttt ttggtttact aacctgaatt gagggaagca aaagtaggag ctcaaaccag  1200
gtgggaacct ggaggcagga gctgatgcag aggcatggag gagtgctgct tactggtctg  1260
ctcctcatgg cttgctcagc ttgttttctt atagaaccca gggccaccgt cacaaaagta  1320
ccatcacctg caatgggttg ggcccttccc cagggatctc tgattaagaa aattccctac  1380
aggtctgtct acaattcttt tttgtttgtt tgtttgtttg tttgtttgtt tgttttcgag  1440
acagggtttg tctgtatagc tttggagcct gtcctggaac tcactctgta gaccaggttg  1500
gcctcgaagt cacaaagatc cacctgcctt tgcctcccta gtgctgggat taaaggcttg  1560
tgtcaccact gccaggccta ttttaaggaa gcattttct ccttgagatt ccttcctctc  1620
aaatgattct agcttgtatc aagttgacat aaaattagcc agcacagaca acaacaatag  1680
aaaattttct atcctacaca atgtaataaa tttattgggt aggatttaac atatgtattc  1740
tatgttttac attctcattc taaaaaggaa tgtgtatgca ctcttacaaa cttccataat  1800
acaaaagaat acagtatgta ttagatatgt gcatatattc cttcccttta tggaaagttt  1860
aaaaagtaga agaatggta taataaactg caacacaaca cgtccctcta ataagatcaa  1920
ggctttcatt tgattttgcc tatccaccac atctaatcaa tggttttgct ttgagcaatc  1980
aagtcacatg attatattac ccatacttga gttgtatatc tgcattgtag atatgttctc  2040
aaagctcagc ctttaagag tagtaggag ggaagatgga ccacaggaag aaggggagg  2100
aaggtgaaga aggaaaacac attcgtgttt ctttaccttc actaatagtt ttgttgacag  2160
attccaccta ctccctgtcc atatccctca tactcttagg ccagtattcc cagtgttatt  2220
gaccctgatg tttacctgtt cgcttgtcat cagcatgtca ccaatcttta aatgccattg  2280
tttgtctcct tattgtcttg tctctgcttc tgcagtaaac aacactgttg tctgaatgag  2340
```

```
tcagtgtcag gcccctttct tataagccag tagaaacgtg caagtttgta catgataaga   2400
ggaaagagtg tagattttga tgtagaaaaa gccaagctcc actctaagcc agaattttga   2460
atacttttta tgcagaaatt ttgttttttgt atgaaatatt cttgtgttat ttatttacat   2520
tatgagtgta ctgtcagaag ctcataaaaa ttaccctgtt cataaaatac attccttcat   2580
ccatatgtca tcattatttt gctatccatc aatatataag gaaggtgttt cacatgcatt   2640
agatgcaata aggtaagtgg tcattttagt tctctttaaa tgatttcatt gttgactcca   2700
gtgtagatag tcatcatggc ataagatgta tcaaatgaag actaggtgtg gtggtgcata   2760
ccttcagtcc cagcacacag aggcagagga acatggattg ctgtgagttt caggtggacc   2820
tggtctacat agtgagttcc aaggtagata gagggtgtct cgagagaccc tgtaagaaaa   2880
gtctatgttt aattgccatg aaaaaattag aggattataa aagagggaat atattgttat   2940
agttatcaac tacaaccagt tcaaatcaga agctttaaaa tgttatttta ttgttcagta   3000
gtgttttaag catatatatg tatacacaca aacatatatg tgtttatata tatgtatatg   3060
tatactggtc aagtattggc tatctattct tgaagtattt atagaaaaat tagaaatgtg   3120
aaaacataca acatgtaggt catttccata ttcatataaa agcaaattag aaaaattaat   3180
ctttaactct gtagtgatat ttgagtttgc taatatctat ttttttattt tctttctag   3239

<210> SEQ ID NO 34
<211> LENGTH: 25
<212> TYPE: DNA
<213> ORGANISM: Artificial
<220> FEATURE:
<223> OTHER INFORMATION: exon3 in CHO Protein S

<400> SEQUENCE: 34 gattatttttt atccaaaata tttgg                                         25

<210> SEQ ID NO 35
<211> LENGTH: 15
<212> TYPE: DNA
<213> ORGANISM: Artificial
<220> FEATURE:
<223> OTHER INFORMATION: DNA element from the CHO Protein S promoter

<400> SEQUENCE: 35
ggagaggagg ggggg                                                     15

<210> SEQ ID NO 36
<211> LENGTH: 21
<212> TYPE: PRT
<213> ORGANISM: Artificial
<220> FEATURE:
<223> OTHER INFORMATION: Zinc finger motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(9)
<223> OTHER INFORMATION: Xaa can be any naturally occurring amino acid
<220> FEATURE:
<221> NAME/KEY: misc_feature
<222> LOCATION: (18)..(20)
<223> OTHER INFORMATION: Xaa can be any naturally occurring amino acid

<400> SEQUENCE: 36

Cys Xaa Xaa Cys Xaa Xaa Xaa Xaa Xaa Gln Ser Gly His Leu Gln Arg
1               5                   10                  15
```

His Xaa Xaa Xaa His
            20

<210> SEQ ID NO 37
<211> LENGTH: 23
<212> TYPE: PRT
<213> ORGANISM: Artificial
<220> FEATURE:
<223> OTHER INFORMATION: Zinc finger motif
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(11)
<223> OTHER INFORMATION: Xaa can be any naturally occurring amino acid
<220> FEATURE:
<221> NAME/KEY: misc_feature
<222> LOCATION: (20)..(22)
<223> OTHER INFORMATION: Xaa can be any naturally occurring amino acid

<400> SEQUENCE: 37

Cys Xaa Xaa Xaa Xaa Cys Xaa Xaa Xaa Xaa Xaa Arg Ser Asp Asn Leu
1               5                   10                  15

Ala Arg His Xaa Xaa Xaa His
            20

<210> SEQ ID NO 38
<211> LENGTH: 21
<212> TYPE: PRT
<213> ORGANISM: Artificial
<220> FEATURE:
<223> OTHER INFORMATION: Zinc finger motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(9)
<223> OTHER INFORMATION: Xaa can be any naturally occurring amino acid
<220> FEATURE:
<221> NAME/KEY: misc_feature
<222> LOCATION: (18)..(20)
<223> OTHER INFORMATION: Xaa can be any naturally occurring amino acid

<400> SEQUENCE: 38

Cys Xaa Xaa Cys Xaa Xaa Xaa Xaa Xaa Arg Ser Asp Asn Leu Thr Arg
1               5                   10                  15

His Xaa Xaa Xaa His
            20

<210> SEQ ID NO 39
<211> LENGTH: 23
<212> TYPE: PRT
<213> ORGANISM: Artificial
<220> FEATURE:
<223> OTHER INFORMATION: Zinc finger motif
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(11)
<223> OTHER INFORMATION: Xaa can be any naturally occurring amino acid
<220> FEATURE:
<221> NAME/KEY: misc_feature
<222> LOCATION: (20)..(22)
<223> OTHER INFORMATION: Xaa can be any naturally occurring amino acid

<400> SEQUENCE: 39

Cys Xaa Xaa Xaa Cys Xaa Xaa Xaa Xaa Arg Ser Asp His Leu
1               5                   10                  15

Thr Arg His Xaa Xaa Xaa His
            20

<210> SEQ ID NO 40
<211> LENGTH: 23
<212> TYPE: PRT
<213> ORGANISM: Artificial
<220> FEATURE:
<223> OTHER INFORMATION: Zinc finger motif
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(11)
<223> OTHER INFORMATION: Xaa can be any naturally occurring amino acid
<220> FEATURE:
<221> NAME/KEY: misc_feature
<222> LOCATION: (20)..(22)
<223> OTHER INFORMATION: Xaa can be any naturally occurring amino acid

<400> SEQUENCE: 40

Cys Xaa Xaa Xaa Xaa Cys Xaa Xaa Xaa Xaa Arg Ser Asp His Leu
1               5                   10                  15

Ala Arg His Xaa Xaa Xaa His
            20

<210> SEQ ID NO 41
<211> LENGTH: 15
<212> TYPE: PRT
<213> ORGANISM: Artificial
<220> FEATURE:
<223> OTHER INFORMATION: Protein sequence target

<400> SEQUENCE: 41

Gly Gly Ala Gly Ala Gly Gly Ala Gly Gly Gly Gly Gly Gly
1               5                   10                  15

<210> SEQ ID NO 42
<211> LENGTH: 321
<212> TYPE: PRT
<213> ORGANISM: Artificial
<220> FEATURE:
<223> OTHER INFORMATION: ZNF-PS protein sequence

<400> SEQUENCE: 42

Met Asp Ala Lys Ser Leu Thr Ala Trp Ser Arg Thr Leu Val Thr Phe
1               5                   10                  15

Lys Asp Val Phe Val Asp Phe Thr Arg Glu Glu Trp Lys Leu Leu Asp
                20                  25                  30

Thr Ala Gln Gln Ile Val Tyr Arg Asn Val Met Leu Glu Asn Tyr Lys
            35                  40                  45

Asn Leu Val Ser Leu Gly Tyr Gln Leu Thr Lys Pro Asp Val Ile Leu
        50                  55                  60

Arg Leu Glu Lys Gly Glu Glu Pro Trp Leu Val Arg Glu Ile His
65                  70                  75                  80

Gln Glu Thr His Pro Asp Ser Glu Thr Ala Phe Glu Ile Lys Ser Ser
                85                  90                  95

Val Ser Ser Arg Ser Ile Phe Lys Asp Lys Gln Ser Cys Asp Ile Lys
            100                 105                 110

Met Glu Gly Met Ala Arg Asn Asp Leu Trp Tyr Leu Ser Leu Glu Glu

```
                     115                 120                 125
Val Trp Lys Pro Gly Lys Lys Gln His Ile Cys His Ile Gln Gly
130                 135                 140

Cys Gly Lys Val Tyr Gly Arg Ser Asp His Leu Ala Arg His Leu Arg
145                 150                 155                 160

Trp His Thr Gly Glu Arg Pro Phe Met Cys Thr Trp Ser Tyr Cys Gly
                165                 170                 175

Lys Arg Phe Thr Arg Ser Asp His Leu Thr Arg His Lys Arg Thr His
                180                 185                 190

Thr Gly Glu Lys Lys Phe Ala Cys Pro Glu Cys Pro Lys Arg Phe Met
            195                 200                 205

Arg Ser Asp Asn Leu Thr Arg His Ile Lys Thr His Thr Gly Glu Arg
210                 215                 220

Pro Phe Ala Cys Asp Trp Gln Gly Cys Asp Lys Lys Phe Ala Arg Ser
225                 230                 235                 240

Asp Asn Leu Ala Arg His His Arg Thr His Thr Gly Glu Lys Arg Phe
                245                 250                 255

Ser Cys Pro Leu Cys Ser Lys Arg Phe Thr Gln Ser Gly His Leu Gln
                260                 265                 270

Arg His Ala Arg Arg His Pro Gly Phe His Pro Asp Leu Leu Arg Arg
            275                 280                 285

Pro Gly Ala Arg Ser Thr Pro Ser Asp Ser Leu Pro Cys Ser Leu
290                 295                 300

Ala Gly Ser Pro Ala Pro Ser Pro Ala Pro Ser Pro Ala Pro Ala Gly
305                 310                 315                 320

Leu

<210> SEQ ID NO 43
<211> LENGTH: 4364
<212> TYPE: DNA
<213> ORGANISM: Artificial
<220> FEATURE:
<223> OTHER INFORMATION: DNA Probe
<220> FEATURE:
<221> NAME/KEY: misc_feature
<222> LOCATION: (2692)..(2697)
<223> OTHER INFORMATION: n is a, c, g, or t

<400> SEQUENCE: 43
ctgctggtat gcctagccct ggtgctgcca gcctcggaga caaactgtaa gtaatccata      60
cctcctggct tctccattcc ctatgtgccc cggcttgaag attttccact aggctgtttg     120
ctgcctccta gtttccagt aagtccgcca ccattcagag agtcgcggca gcctgggtct      180
ggtgggcagt gtaaaggtgg gacaggatca aagcttgcct tgctttgaga accattgtcc     240
acaggacttg attccagaac ccgggtgaca ctaagtgtca aaggaattgc ttgaacatag     300 tcctaaaatat tgctaggaaa gctaagtcaa gcctgttgcc ctcctcccgt ttacaagagt    360
gccccagccc gcaccctctc ctgcggctaa ccttcctttt gcaatttctg gactttgaac    420
ttgattgact ggtctcacat tgacaaactg tttggggact gctggggtgt acatatgat     480 tctctaacct tgatataaga aatagctgtt ggatgttacc ttgtaccgag gatcattttc    540
tgagggtttt gactgttgcc gctttgagat ggcagcaaga attctgtaca acacacacat    600
ttttgtgttt cttggtcttt cctcttccca ttctcagatt ccgggcagta tatcgagttt    660
tctcttagaa atataaaacg aaccacaagg tttagtaca ttttaatggt caattaaatt     720
gtttttagaa gcttaaatat gttcataatt aacactgctt tcttttgctc ttttgtagtc    780
```

```
ccagtcactg gcatgggagc aataactgta taacaaatac cacttaggtc actgcgagca    840
ccaaagaaac ttttcaaaga tggtaattaa gtaggagttt gctggaattg caagttttta    900
ttaattagta aggaatctag cctgatattt ttaaatgtct aactaagtta aagaccagaa    960
tgaaactggt tcactttta ttgaggataa acaagttaca gttataaagc ctcaacaatc   1020
aaagccctac gatgaagcag cgtgtgactg tatgcacatg atctatcttg ttcagaggaa   1080
caatcaaaca ttttcagata gcatcagggc ggtggtggta ctcgcctata atcctagcaa   1140
agtcagaggc aagcagatct ctgtgttcaa ggccagccta gtctacagag tgagttccag   1200
gacaactggg gctacacaga gaaacctgtc tcagagaaaa acaaaataaa accaaattca   1260
gatagctggt gtttgggaaa agagcaaaag acagcagtgc tggccacaca gagagtagac   1320
aagttcattc tacaaggaca tcacagaaag aatatgtgac ccaatgacga ccataaactt   1380
tcttgttcct gtgtcaaatt atctccggtt tattgatgaa gaaccagaca ctatgagctg   1440
cgtctcctcc ttaagatttt gttttggtgt cttgttttg tcaaggggtt tcattgtggc   1500
cctgagcatt agatccaggg ctttgtgcat gctaggccag ggagctatat tcccgaactc   1560
cagaagacta ggaatttgag atataaatag aatttgaatt accttctgta caattgattg   1620
tatggttcta gaaatattgc tatattaagg gaagcctttg cagaagacag ttattttgag   1680
atggtgcata acacaaaaga aatgaactaa agcctgaggc ctgctctgta gctctgcctt   1740
gcccttagcc tacaataact ttctttacct ttcaagcatg tgccaccacg cctgactttc   1800
aggcccttca ttttaacaag aaagcaagta ttcagttatc aactgacttt ccaaatgcat   1860
ttgtatgaat aaaaactaca aaaatataaa aataagaact atacacacaa aagccttgta   1920
tttaaaattt acgctgtgga catatttgc tcatcattcg tgagagcttg cggtaaaaag   1980
gcaaggggga agaggaggat atctattttg ggtaggctaa tttggcctta tccagacttc   2040
ccttttgggt ggatgcagtc tgcccagcac actattggcc catttcttct acatggcttt   2100
gtgctctgct ctgcccttag ctaattgtcc cctttgacat gcttttgtct ttccttaaag   2160
tttctatact tcaaaaacca tcccgctaca ctaatggagt gatttctca agggttgctt   2220 tatgtttggg gtttgtactg caagagttag tttctgatat agcaatggtg atagtatagt   2280
cttctaccat gaactctatg ccagcaagta caggggtata tttcacatgg gtgttttctg   2340
ttcactgagt ttcatgtctt cttttgtatct ttttgttttg ttttgtgaga cagggttct    2400 ctgtagcttt tgagtcagtc ctggaacttg ctggccggcc ttgaactcac agagattcac   2460
ctgcctctgc ctcccaagtg ctgggattta aggtgtgagt caccactgcc aggttttttc   2520
tttgtatctt gagtgaacta aataggtaag ctttaaataa taatatgagc agtctattta   2580
tatacattaa atattaaatg cattgtgaga tgagcatagc ctttgaggcc caggaacaga   2640
aagatttact tcacattgta aatatactgg tatacataca aacgtacata cnnnnnngtg   2700
tgtgtgtgtg tgtgtgtgtg tgtgtgcatg ccatagcaca catgtgaagt ccagagtaca   2760
gcattctctt tttctacctt tctgtagatt cttgtggtca gagtcaggtc aaatcaaatc   2820
agacagatgc atgtataaaa tgctcttacc cactgaacca tcttgctgct tggtccacaa   2880
gcttagtgga agaatgctgg gaagtgaata gtatgttttt aaatgtagtt aaccttgact   2940
ttttgttgtt gttgctgtta ttgaggccac attttcattg ttctgagaaa atattactat   3000
tttcctcaga cagaattata tatttatttg aagttcatga attccatatt attttcctgt   3060
atttattaca aatagcatgc ttaaacactt ccaagtagtg aaacagctgc tcatgtagga   3120
cacggattat tgacagtgct gccatttatc agccagtaat ccacttggca ggtagcacgc   3180
```

-continued

```
tcatcgttat cctttatgca cacaaagcct tgtttgaatt ttatctttta atgagtgtca    3240
atgaaatgga aagagataag agttaaaaat acaacccaaa ctattgtatt tacatttctc    3300
ttttagaaga aacctaaagc agcattactt cttgcccata tttaataaat aacatcattt    3360
acccttgttc cctgcctcca gactctccca tatactcctc tttcaatttt attggcccct    3420
ttaaatgaca tatcattaca tgtatatccc tacacataag tataaccagt tcagtttgta    3480
taatgttact tgcatgtgtg ttttcaatgc tgatcatttg gtagtggata accaatggtg    3540
tgccctatga agggcagag tatttgtatc atgcttagca ttcctttgtt gactgtagga    3600
ttttgtttaa ggttgaggtc tcttggtctt tcccctgtct gcttctgcat gtccatggcc    3660
atccttgttc agctcatgtt tatgtagtca tgctgatgag gctttatgga tgtagcttct    3720
gacattgcta agcaacacag tctcagcaaa ctccccagtc ctctggttct tacaatcttt    3780
ccacactgtt tcaccatgtt gtctgagcct taggtgctga agttgttttg tgtctgtatc    3840
cattgggact aggctccaca tgtctgcatt ttgattactt gtggttttct gtaacggtct    3900
ctatgtgttg caacgagaag gagtagttgc tttgacgatg tgtaaagact atcttgtggg    3960
tataaggaca atatttgca tgaagctatg gattatgctg gtctcaagca tgaactggat    4020
aaattgtaca gctcacacaa aacagctata gctagctgca cagtcaggca tgcactgatc    4080
tgcttgggga gttgttaacc aaagggctta catagctatg tattttctaa gctctagttt    4140
tactatcaca agaaaatta attcacccctt aattgtttaa taagatgata tatcttaggg    4200
aaaaaatgaa ggtctttttt tgacttatat aaaagcttat gttttctaca gttttgtcaa    4260
aagaacatgc ctcgcaagtc ctggtgagga agcgccgcgc aaataccttg cttgaagaaa    4320
ctaaaaaggg caatcttgaa agagaatgca tcgaagagct ctgc                    4364
```

<210> SEQ ID NO 44
<211> LENGTH: 948
<212> TYPE: DNA
<213> ORGANISM: Artificial
<220> FEATURE:
<223> OTHER INFORMATION: DNA Probe

<400> SEQUENCE: 44

```
atgaagctac tgtcttctat cgaacaagca tgcccaaaaa agaagagaaa ggtagatgaa      60
aaaccttaca gtgtccgga atgtgggaag tcctttagtc ggagcgacaa cctgccccgg     120
caccagcgga cgcataccgg tgagaagccc tacaaatgcc agaatgcgg aaaatcattt     180 tcgcggagca gcaacctgcg ggagcaccaa cgaacccaca caggcgagaa ccatttaaa    240 tgtcctgagt gtggtaagag ctttagccgg agcgacaacc tgacccggca tcaagctact    300
catacgggcg gcgtggcag cggtggcggt agcggcggtg gcagcggtgg cggatcccaa    360
ctagtcaaaa gtgaactgga ggagaagaaa tctgaacttc gtcataaatt gaaatatgtg    420
cctcatgaat atattgaatt aattgaaatt gccagaaatt ccactcagga tagaattctt    480
gaaatgaagg taatggaatt ttttatgaaa gtttatggat atagaggtaa acatttgggt    540
ggatcaagga aaccggacgg agcaatttat actgtcggat ctcctattga ttacggtgtg    600
atcgtggata ctaaagctta tagcggaggt tataatctgc caattggcca agcagatgaa    660
atgcaacgat atgtcgaaga aaatcaaaca cgaaacaaac atatcaaccc taatgaatgg    720
tggaaagtct atccatcttc tgtaacggaa tttaagtttt tatttgtgag tggtcacttt    780
aaaggaaact acaaagctca gcttacacga ttaaatcata tcactaattg taatggagct    840
gttcttagtg tagaagagct tttaattggt ggagaaatga ttaaagccgg cacattaacc    900
```
ttagaggaag tgagacggaa attttaataac ggcgagataa acttttag        948

<210> SEQ ID NO 45
<211> LENGTH: 978
<212> TYPE: DNA
<213> ORGANISM: Artificial
<220> FEATURE:
<223> OTHER INFORMATION: DNA Probe

<400> SEQUENCE: 45
atgaagctac tgtcttctat cgaacaagca tgcccaaaaa agaagagaaa ggtagatgaa        60
aaaccttaca agtgtccgga atgtgggaag tcctttagtc ggagcgacaa cctggcccgg       120
caccagcgga cgcataccgg tgagaagccc tacaaatgcc agaatgcgg aaaatcattt        180
tcgcggagca gcaacctgcg ggagcaccaa cgaacccaca caggcgagaa accatttaaa       240
tgtcctgagt gtggtaagag ctttagccgg agcgacaacc tgacccggca tcaagctact       300
catacgggcg gcgtggcag cggtggcggt agcggcggtg gcagcggtgg cggatccgta        360
ttagaaaaaa gtgatattga aaaatttaag aatcaattgc gtacggaact aaccaatatt       420
gaccattctt atcttaaagg aattgatata gctagtaaaa agaaaaccag taatgttgaa       480
aatacggaat ttgaagcaat atcaaccaag atttttacgg atgagttggg tttttcaggc       540
aaacatctag gaggaagcaa caaaccagat ggactcctgt gggatgatga ttgtgcaatt       600
attcttgatt caaaagctta ctcagaaggc tttccactca ctgcctccca cacagatgct       660
atgggaagat atttgaggca atttacgag cgaaaagaag aaataaagcc aacgtggtgg        720
gatattgctc cagaacattt agacaataca tatttcgctt acgtttctgg gagttttcg        780
ggtaattata aggaacagtt acaaaaattt aggcaagata caaaccattt aggtggggca       840
ctagagtttg ttaaattgtt attactagca ataattata aaactcaaaa aatgagtaaa        900
aaagaagtta agaaaagtat tcttgattat aatatttcat atgaagaata tgctccatta       960
cttgcagaaa tagagtaa                                                     978

<210> SEQ ID NO 46
<211> LENGTH: 948
<212> TYPE: DNA
<213> ORGANISM: Artificial
<220> FEATURE:
<223> OTHER INFORMATION: DNA Probe

<400> SEQUENCE: 46
atgaagctac tgtcttctat cgaacaagca tgcccaaaaa agaagagaaa ggtagatgaa        60
aaaccttaca agtgtccgga atgtgggaag tcctttagtc ggagcgacgc cctgacccag       120
caccagcgga cgcataccgg tgagaagccc tacaaatgcc agaatgcgg aaaatcattt        180
tcgcagagca gccacctggc ccggcaccaa cgaacccaca caggcgagaa accatttaaa       240
tgtcctgagt gtggtaagag ctttagccag agcagccacc tgacccggca tcaagctact       300
catacgggcg gcgtggcag cggtggcggt agcggcggtg gcagcggtgg cggatcccaa        360
ctagtcaaaa gtgaactgga ggagaagaaa tctgaacttc gtcataaatt gaaatatgtg       420
cctcatgaat atattgaatt aattgaaatt gccagaaatt ccactcagga tagaattctt       480
gaaatgaagg taatggaatt ttttatgaaa gtttatggat atagaggtaa acatttgggt       540
ggatcaagga aaccggacgg agcaatttat actgtcggat ctcctattga ttacggtgtg       600
atcgtggata ctaaagctta tagcggaggt tataatctgc caattggcca agcagatgaa       660
atgcaacgat atgtcgaaga aaatcaaaca cgaaacaaac atatcaaccc taatgaatgg       720

```
tggaaagtct atccatcttc tgtaacggaa tttaagtttt tatttgtgag tggtcacttt      780
aaaggaaact acaaagctca gcttacacga ttaaatcata tcactaattg taatggagct      840
gttcttagtg tagaagagct tttaattggt ggagaaatga ttaaagccgg cacattaacc      900
ttagaggaag tgagacggaa atttaataac ggcgagataa acttttag                  948
```

<210> SEQ ID NO 47
<211> LENGTH: 978
<212> TYPE: DNA
<213> ORGANISM: Artificial
<220> FEATURE:
<223> OTHER INFORMATION: DNA Probe

<400> SEQUENCE: 47

```
atgaagctac tgtcttctat cgaacaagca tgcccaaaaa agaagagaaa ggtagatgaa       60
aaaccttaca gtgtccggaa atgtgggaag tcctttagtc ggagcgacgc cctgacccag      120
caccagcgga cgcataccgg tgagaagccc tacaaatgcc cagaatgcgg aaaatcattt      180
tcgcagagca gccacctggc ccggcaccaa cgaacccaca caggcgagaa accatttaaa      240
tgtcctgagt gtggtaagag ctttagccag agcagccacc tgacccggca tcaagctact      300
catacgggcg gcggtggcag cggtggcggt agcggcggtg gcagcggtgg cggatccgta      360
ttagaaaaaa gtgatattga aaaatttaag aatcaattgc gtacggaact aaccaatatt      420
gaccattctt atcttaaagg aattgatata gctagtaaaa agaaaaccag taatgttgaa      480
aatacggaat tgaagcaat atcaaccaag atttttacgg atgagttggg ttttcaggc       540 aaacatctag gaggaagcaa caaaccagat ggactcctgt gggatgatga ttgtgcaatt      600
attcttgatt caaagctta ctcagaaggc tttccactca ctgcctccca cacagatgct      660
atgggaagat atttgaggca atttacgag cgaaaagaag aaataaagcc aacgtggtgg       720
gatattgctc cagaacattt agacaataca tatttcgctt acgtttctgg gagttttcg       780 ggtaattata aggaacagtt acaaaaattt aggcaagata caaaccattt aggtggggca      840
ctagagtttg ttaaattgtt attactagca ataattata aaactcaaaa aatgagtaaa      900
aaagaagtta agaaaagtat tcttgattat aatatttcat atgaagaata tgctccatta      960
cttgcagaaa tagagtaa                                                  978
```

<210> SEQ ID NO 48
<211> LENGTH: 315
<212> TYPE: PRT
<213> ORGANISM: Artificial
<220> FEATURE:
<223> OTHER INFORMATION: Left zinc finger-Fok I protein sequence

<400> SEQUENCE: 48

```
Met Lys Leu Leu Ser Ser Ile Glu Gln Ala Cys Pro Lys Lys Lys Arg
1               5                   10                  15

Lys Val Asp Glu Lys Pro Tyr Lys Cys Pro Glu Cys Gly Lys Ser Phe
            20                  25                  30

Ser Arg Ser Asp Asn Leu Ala Arg His Gln Arg Thr His Thr Gly Glu
        35                  40                  45

Lys Pro Tyr Lys Cys Pro Glu Cys Gly Lys Ser Phe Ser Arg Ser Ser
    50                  55                  60

Asn Leu Arg Glu His Gln Arg Thr His Thr Gly Glu Lys Pro Phe Lys
65                  70                  75                  80

Cys Pro Glu Cys Gly Lys Ser Phe Ser Arg Ser Asp Asn Leu Thr Arg
                85                  90                  95
```

```
His Gln Ala Thr His Thr Gly Gly Gly Ser Gly Gly Gly Ser Gly
            100                 105                 110

Gly Gly Ser Gly Gly Gly Ser Gln Leu Val Lys Ser Glu Leu Glu
        115                 120                 125

Glu Lys Lys Ser Glu Leu Arg His Lys Leu Lys Tyr Val Pro His Glu Tyr
    130                 135                 140

Ile Glu Leu Ile Glu Ile Ala Arg Asn Ser Thr Gln Asp Arg Ile Leu
145                 150                 155                 160

Glu Met Lys Val Met Glu Phe Phe Met Lys Val Tyr Gly Tyr Arg Gly
                165                 170                 175

Lys His Leu Gly Gly Ser Arg Lys Pro Asp Gly Ala Ile Tyr Thr Val
            180                 185                 190

Gly Ser Pro Ile Asp Tyr Gly Val Ile Val Asp Thr Lys Ala Tyr Ser
        195                 200                 205

Gly Gly Tyr Asn Leu Pro Ile Gly Gln Ala Asp Glu Met Gln Arg Tyr
    210                 215                 220

Val Glu Glu Asn Gln Thr Arg Asn Lys His Ile Asn Pro Asn Glu Trp
225                 230                 235                 240

Trp Lys Val Tyr Pro Ser Ser Val Thr Glu Phe Lys Phe Leu Phe Val
                245                 250                 255

Ser Gly His Phe Lys Gly Asn Tyr Lys Ala Gln Leu Thr Arg Leu Asn
            260                 265                 270

His Ile Thr Asn Cys Asn Gly Ala Val Leu Ser Val Glu Glu Leu Leu
        275                 280                 285

Ile Gly Gly Glu Met Ile Lys Ala Gly Thr Leu Thr Leu Glu Glu Val
    290                 295                 300

Arg Arg Lys Phe Asn Asn Gly Glu Ile Asn Phe
305                 310                 315

<210> SEQ ID NO 49
<211> LENGTH: 325
<212> TYPE: PRT
<213> ORGANISM: Artificial
<220> FEATURE:
<223> OTHER INFORMATION: Left zinc finger-Sts I protein sequence

<400> SEQUENCE: 49

Met Lys Leu Leu Ser Ser Ile Glu Gln Ala Cys Pro Lys Lys Arg
1               5                   10                  15

Lys Val Asp Glu Lys Pro Tyr Lys Cys Pro Glu Cys Gly Lys Ser Phe
            20                  25                  30

Ser Arg Ser Asp Asn Leu Ala Arg His Gln Arg Thr His Thr Gly Glu
        35                  40                  45

Lys Pro Tyr Lys Cys Pro Glu Cys Gly Lys Ser Phe Ser Arg Ser Ser
    50                  55                  60

Asn Leu Arg Glu His Gln Arg Thr His Thr Gly Glu Lys Pro Phe Lys
65                  70                  75                  80

Cys Pro Glu Cys Gly Lys Ser Phe Ser Arg Ser Asp Asn Leu Thr Arg
                85                  90                  95

His Gln Ala Thr His Thr Gly Gly Gly Ser Gly Gly Gly Ser Gly
            100                 105                 110

Gly Gly Ser Gly Gly Gly Ser Val Leu Glu Lys Ser Asp Ile Glu Lys
        115                 120                 125

Phe Lys Asn Gln Leu Arg Thr Glu Leu Thr Asn Ile Asp His Ser Tyr
    130                 135                 140

Leu Lys Gly Ile Asp Ile Ala Ser Lys Lys Lys Thr Ser Asn Val Glu
```

```
                145                 150                 155                 160
Asn Thr Glu Phe Glu Ala Ile Ser Thr Lys Ile Phe Thr Asp Glu Leu
                    165                 170                 175
Gly Phe Ser Gly Lys His Leu Gly Gly Ser Asn Lys Pro Asp Gly Leu
                    180                 185                 190
Leu Trp Asp Asp Asp Cys Ala Ile Ile Leu Asp Ser Lys Ala Tyr Ser
                195                 200                 205
Glu Gly Phe Pro Leu Thr Ala Ser His Thr Asp Ala Met Gly Arg Tyr
                210                 215                 220
Leu Arg Gln Phe Thr Glu Arg Lys Glu Ile Lys Pro Thr Trp Trp
225                 230                 235                 240
Asp Ile Ala Pro Glu His Leu Asp Asn Thr Tyr Phe Ala Tyr Val Ser
                    245                 250                 255
Gly Ser Phe Ser Gly Asn Tyr Lys Glu Gln Leu Gln Lys Phe Arg Gln
                    260                 265                 270
Asp Thr Asn His Leu Gly Gly Ala Leu Glu Phe Val Lys Leu Leu Leu
                275                 280                 285
Leu Ala Asn Asn Tyr Lys Thr Gln Lys Met Ser Lys Lys Glu Val Lys
                290                 295                 300
Lys Ser Ile Leu Asp Tyr Asn Ile Ser Tyr Glu Glu Tyr Ala Pro Leu
305                 310                 315                 320
Leu Ala Glu Ile Glu
                325

<210> SEQ ID NO 50
<211> LENGTH: 315
<212> TYPE: PRT
<213> ORGANISM: Artificial
<220> FEATURE:
<223> OTHER INFORMATION: Right zinc finger-Fok I protein sequence

<400> SEQUENCE: 50

Met Lys Leu Leu Ser Ser Ile Glu Gln Ala Cys Pro Lys Lys Lys Arg
1               5                   10                  15
Lys Val Asp Glu Lys Pro Tyr Lys Cys Pro Glu Cys Gly Lys Ser Phe
                20                  25                  30
Ser Arg Ser Asp Ala Leu Thr Gln His Gln Arg Thr His Thr Gly Glu
            35                  40                  45
Lys Pro Tyr Lys Cys Pro Glu Cys Gly Lys Ser Phe Ser Gln Ser Ser
        50                  55                  60
His Leu Ala Arg His Gln Arg Thr His Thr Gly Glu Lys Pro Phe Lys
65                  70                  75                  80
Cys Pro Glu Cys Gly Lys Ser Phe Ser Gln Ser Ser His Leu Thr Arg
                85                  90                  95
His Gln Ala Thr His Thr Gly Gly Gly Gly Ser Gly Gly Gly Ser Gly
                    100                 105                 110
Gly Gly Ser Gly Gly Gly Ser Gln Leu Val Lys Ser Glu Leu Glu Glu
                115                 120                 125
Lys Lys Ser Glu Leu Arg His Lys Leu Lys Tyr Val Pro His Glu Tyr
                130                 135                 140
Ile Glu Leu Ile Glu Ile Ala Arg Asn Ser Thr Gln Asp Arg Ile Leu
145                 150                 155                 160
Glu Met Lys Val Met Glu Phe Phe Met Lys Val Tyr Gly Tyr Arg Gly
                    165                 170                 175
Lys His Leu Gly Gly Ser Arg Lys Pro Asp Gly Ala Ile Tyr Thr Val
                180                 185                 190
```

```
Gly Ser Pro Ile Asp Tyr Gly Val Ile Val Asp Thr Lys Ala Tyr Ser
            195                 200                 205

Gly Gly Tyr Asn Leu Pro Ile Gly Gln Ala Asp Glu Met Gln Arg Tyr
            210                 215                 220

Val Glu Glu Asn Gln Thr Arg Asn Lys His Ile Asn Pro Asn Glu Trp
225                 230                 235                 240

Trp Lys Val Tyr Pro Ser Ser Val Thr Glu Phe Lys Phe Leu Phe Val
                245                 250                 255

Ser Gly His Phe Lys Gly Asn Tyr Lys Ala Gln Leu Thr Arg Leu Asn
            260                 265                 270

His Ile Thr Asn Cys Asn Gly Ala Val Leu Ser Val Glu Glu Leu Leu
            275                 280                 285

Ile Gly Gly Glu Met Ile Lys Ala Gly Thr Leu Thr Leu Glu Glu Val
            290                 295                 300

Arg Arg Lys Phe Asn Asn Gly Glu Ile Asn Phe
305                 310                 315
```

<210> SEQ ID NO 51
<211> LENGTH: 325
<212> TYPE: PRT
<213> ORGANISM: Artificial
<220> FEATURE:
<223> OTHER INFORMATION: Right zinc finger-Sts I protein sequence

<400> SEQUENCE: 51

```
Met Lys Leu Leu Ser Ser Ile Glu Gln Ala Cys Pro Lys Lys Lys Arg
1               5                   10                  15

Lys Val Asp Glu Lys Pro Tyr Lys Cys Pro Glu Cys Gly Lys Ser Phe
                20                  25                  30

Ser Arg Ser Asp Ala Leu Thr Gln His Gln Arg Thr His Thr Gly Glu
            35                  40                  45

Lys Pro Tyr Lys Cys Pro Glu Cys Gly Lys Ser Phe Ser Gln Ser Ser
        50                  55                  60

His Leu Ala Arg His Gln Arg Thr His Thr Gly Glu Lys Pro Phe Lys
65                  70                  75                  80

Cys Pro Glu Cys Gly Lys Ser Phe Ser Gln Ser Ser His Leu Thr Arg
                85                  90                  95

His Gln Ala Thr His Thr Gly Gly Gly Gly Ser Gly Gly Gly Ser Gly
            100                 105                 110

Gly Gly Ser Gly Gly Gly Ser Val Leu Glu Lys Ser Asp Ile Glu Lys
        115                 120                 125

Phe Lys Asn Gln Leu Arg Thr Glu Leu Thr Asn Ile Asp His Ser Tyr
    130                 135                 140

Leu Lys Gly Ile Asp Ile Ala Ser Lys Lys Thr Ser Asn Val Glu
145                 150                 155                 160

Asn Thr Glu Phe Glu Ala Ile Ser Thr Lys Ile Phe Thr Asp Glu Leu
                165                 170                 175

Gly Phe Ser Gly Lys His Leu Gly Gly Ser Asn Lys Pro Asp Gly Leu
            180                 185                 190

Leu Trp Asp Asp Asp Cys Ala Ile Ile Leu Asp Ser Lys Ala Tyr Ser
        195                 200                 205

Glu Gly Phe Pro Leu Thr Ala Ser His Thr Asp Ala Met Gly Arg Tyr
    210                 215                 220

Leu Arg Gln Phe Thr Glu Arg Lys Glu Glu Ile Lys Pro Thr Trp Trp
225                 230                 235                 240
```

```
Asp Ile Ala Pro Glu His Leu Asp Asn Thr Tyr Phe Ala Tyr Val Ser
            245                 250                 255

Gly Ser Phe Ser Gly Asn Tyr Lys Glu Gln Leu Gln Lys Phe Arg Gln
        260                 265                 270

Asp Thr Asn His Leu Gly Gly Ala Leu Glu Phe Val Lys Leu Leu Leu
        275                 280                 285

Leu Ala Asn Asn Tyr Lys Thr Gln Lys Met Ser Lys Lys Glu Val Lys
        290                 295                 300

Lys Ser Ile Leu Asp Tyr Asn Ile Ser Tyr Glu Glu Tyr Ala Pro Leu
305                 310                 315                 320

Leu Ala Glu Ile Glu
            325

<210> SEQ ID NO 52
<211> LENGTH: 9064
<212> TYPE: DNA
<213> ORGANISM: Artificial
<220> FEATURE:
<223> OTHER INFORMATION: Protein S promoter-EGFP-Protein S intron 1
      targeting construct
<220> FEATURE:
<221> NAME/KEY: misc_feature
<222> LOCATION: (5360)..(5365)
<223> OTHER INFORMATION: n is a, c, g, or t

<400> SEQUENCE: 52
ggtaccgagc tcttacgcgt gctagcccgg gctcgagatc tcaacccctt ttgaccatac      60
acatttctac tctttgtgtt tgctggagct gttttctccc cacactcaac ccccttttgct    120 gaagcctgga acttgctttc cacagcttaa gttgttatag gtttcaatca tctgtccacc    180
tccctgactt tcataatttt gtgaaatacc cttgcatata tatatgggac taaatattat    240
tttctcctgg ttgtccataa tagattaatt taattcctaa acaaagaaca gaacatagat    300
tggtatagta gaagagtttc ccttctcct actgcatgaa tggaaattcc ccaaaccatc     360
cttatcagag aaattaactc acatactagt caccctttcat tcagctggat gacaaaatca    420
ttttaaaaaa agagaataaa gaaaacagat aagaacaact agatctagga ataatactta    480
aaatatgatt ctgcttagta ggtttcattc acacacctag aaaaaaaaat cagtcaatgt    540
ttcctttggg cagaaaatga gcaataatgg gtatgcattg accactactg ttggacatag    600
ccttattgct tcatatagca tctattcaaa gtctcagatc aacactatga aaacctgtca    660
tctctgtatt agatgatgtg actggggctg taaagggtaa gctcttttct tacagctata    720
caacaacgct aagaccaagt tctgtgctt gagcccaggc agtttagttt cccaggagca    780
acctaaagcc tgattcacag gcatatgtat gatccaaact gaatggtagt acatcaatac    840
caaaacaatc tattggtgga aacacaccat aggtgatcga aatactccat tttcttttcc    900
tctcatgact tctgttctga gcagtcctct tcctaaagtc tacattgtct tctgagttca    960
ggctgacatc ttgacatcct cctggctggc acagtctctg gacaaggagg gaagaaggag   1020
agaaggggaa agggagagga gggggggagg gagagaaaga atgggaagag gaaggatatg   1080
aaagagagaa gagaggaggg aaggcgggag gaagggaggg aggagggggag ggagagaggg   1140 agagagagga gagagagaga gagagagaga gagagagaga gagagagaga gagagagaga   1200
gagagggaga gggagagaga gacagagaga gagagaggga gagggagaga gagagagaga   1260
gagagagaga gagagagaga gagagagagt gaggagagag agagagagtt tcttcacca    1320 ttggacattc ctaagaaaaa gaagtaaatg caggattggg gacagtgaca gaggacctct   1380
gataaacttt ctgaggcctc tgacctcact ctctcggagc cctcctccac cacccacccc   1440
```

```
cccccctccct agctgagaaa agcttccagg aaatgtccca gtcatcgctt ccctcccgg    1500 gctgggggct gggagcgggc ggtcccctca ggccagggct gctccggccg cgctcgggca    1560
gggccacaac agagctggga aagctgagcc caggctcgca gctcctctgg gcggagcgcc    1620
ggctcggtcc ccgctgcgcc agccgtgatc cccggcagcc tgctcagcca tggtgagcaa    1680
gggcgaggag ctgttcaccg gggtggtgcc catcctggtc gagctggacg gcgacgtaaa    1740
cggccacaag ttcagcgtgt ccggcgaggg cgagggcgat gccacctacg gcaagctgac    1800
cctgaagttc atctgcacca ccggcaagct gcccgtgccc tggcccaccc tcgtgaccac    1860
cctgacctac ggcgtgcagt gcttcagccg ctaccccgac cacatgaagc agcacgactt    1920
cttcaagtcc gccatgcccg aaggctacgt ccaggagcgc accatcttct caaggacga    1980 cggcaactac aagacccgcg ccgaggtgaa gttcgagggc gacaccctgg tgaaccgcat    2040
cgagctgaag ggcatcgact tcaaggagga cggcaacatc ctggggcaca agctggagta    2100
caactacaac agccacaacg tctatatcat ggccgacaag cagaagaacg gcatcaaggt    2160
gaacttcaag atccgccaca acatcgagga cggcagcgtg cagctcgccg accactacca    2220
gcagaacacc cccatcggcg acggccccgt gctgctgccc gacaaccact acctgagcac    2280
ccagtccgcc ctgagcaaag accccaacga gaagcgcgat cacatggtcc tgctggagtt    2340
cgtgaccgcc gccgggatca ctctcggcat ggacgagctg tacaagtaaa gcggccgcga    2400
ctctagagtc ggggcggccg gccgcttcga gcagacatga taagatacat tgatgagttt    2460
ggacaaacca aactagaat gcagtgaaaa aaatgcttta tttgtgaaat ttgtgatgct    2520
attgctttat ttgtaaccat tataagctgc aataaacaag ttaacaacaa caattgcatt    2580
cattttatgt ttcaggttca gggggaggtg tgggaggttt tttaaagcaa gtaaaacctc    2640
tacaaatgtg gtaaaatcga taaggatcct gctggtatgc ctagccctgg tgctgccagc    2700
ctcggagaca aactgtaagt aatccatacc tcctggcttc tccattccct atgtgccccg    2760
gcttgaagat tttccactag gctgtttgct gcctcctaag tttccagtaa gtccgccacc    2820
attcagagag tcgcggcagc ctgggtctgg tgggcagtgt aaaggtggga caggatcaaa    2880
gcttgccttg cttttgagaac cattgtccac aggacttgat tccagaaccc gggtgacact    2940
aagtgtcaaa ggaattgctt gaacatagtc ctaaatattg ctaggaaagc taagtcaagc    3000
ctgttgccct cctcccgttt acaagagtgc cccagcccgc accctctcct gcggctaacc    3060
ttccttttgc aatttctgga ctttgaactt gattgactgg tctcacattg acaaactgtt    3120
tggggactgc tggggtgtta catatgattc tctaaccttg atataagaaa tagctgttgg    3180
atgttacctt gtaccgagga tcattttctg agggttttga ctgttgccgc tttgagatgg    3240
cagcaagaat tctgtacaac acacacattt ttgtgtttct tggtcttttcc tcttcccatt    3300 ctcagattcc gggcagtata tcgagttttc tcttagaaat ataaaacgaa ccacaaggtt    3360
ttagtacatt ttaatggtca attaaattgt ttttagaagc ttaaatatgt tcataattaa    3420
cactgctttc ttttgctctt ttgtagtccc agtcactggc atgggagcaa taactgtata    3480
acaaatacca cttaggtcac tgcgagcacc aaagaaactt ttcaaagatg gtaattaagt    3540
aggagtttgc tggaattgca gttttttatt aattagtaag gaatctagcc tgatattttt    3600
aaatgtctaa ctaagttaaa gaccagaatg aaactggttc acttttttatt gaggataaac    3660 aagttacagt tataaagcct caacaatcaa agccctacga tgaagcagcg tgtgactgta    3720
tgcacatgat ctatcttgtt cagaggaaca atcaaacatt ttcagatagc atcagggcgg    3780
tggtggtact cgcctataat cctagcaaag tcagaggcaa gcagatctct gtgttcaagg    3840
```

```
ccagcctagt ctacagagtg agttccagga caactggggc tacacagaga aacctgtctc    3900
agagaaaaac aaaataaaac caaattcaga tagctggtgt ttgggaaaag agcaaaagac    3960
agcagtgctg gccacacaga gagtagacaa gttcattcta caaggacatc acagaaagaa    4020
tatgtgaccc aatgacgacc ataaactttc ttgttcctgt gtcaaattat ctccggttta    4080
ttgatgaaga accagacact atgagctgcg tctcctcctt aagattttgt tttggtgtct    4140
tgtttttgtc aaggggtttc attgtggccc tgagcattag atccagggct ttgtgcatgc    4200
taggccaggg agctatattc ccgaactcca gaagactagg aatttgagat ataaatagaa    4260
tttgaattac cttctgtaca attgattgta tggttctaga atattgcta tattaaggga     4320 agcctttgca gaagacagtt attttgagat ggtgcataac acaaaagaaa tgaactaaag    4380
cctgaggcct gctctgtagc tctgccttgc ccttagccta caataacttt ctttaccttt    4440
caagcatgtg ccaccacgcc tgactttcag gcccttcatt ttaacaagaa agcaagtatt    4500
cagttatcaa ctgactttcc aaatgcattt gtatgaataa aaactacaaa aatataaaaa    4560
taagaactat acacacaaaa gccttgtatt taaaatttac gctgtggaca tattttgctc    4620
atcattcgtg agagcttgcg gtaaaaaggc aaggggaag aggaggatat ctattttggg     4680
taggctaatt tggccttatc cagacttccc ttttgggtgg atgcagtctg cccagcacac    4740
tattggccca tttcttctac atggctttgt gctctgctct gcccttagct aattgtcccc    4800
tttgacatgc ttttgtcttt ccttaaagtt tctatacttc aaaaaccatc ccgctacact    4860
aatggagtga ttttctcaag ggttgcttta tgtttgggt ttgtactgca agagttagtt     4920
tctgatatag caatggtgat agtatagtct tctaccatga actctatgcc agcaagtaca    4980
ggggtatatt tcacatgggt gttttctgtt cactgagttt catgtcttct ttgtatcttt    5040
ttgttttgtt ttgtgagaca gggtttctct gtagcttttg agtcagtcct ggaacttgct    5100
ggccggcctt gaactcacag agattcacct gcctctgcct cccaagtgct gggatttaag    5160
gtgtgagtca ccactgccag gttttttctt tgtatcttga gtgaactaaa taggtaagct    5220
ttaaataata atatgagcag tctatttata tacattaaat attaaatgca ttgtgagatg    5280
agcatagcct ttgaggccca ggaacagaaa gatttacttc acattgtaaa tatactggta    5340
tacatacaaa cgtacatacn nnnnngtgtg tgtgtgtg tgtgtgtg tgtgcatgcc         5400 atagcacaca tgtgaagtcc agagtacagc attctctttt tctacctttc tgtagattct    5460
tgtggtcaga gtcaggtcaa atcaaatcag acagatgcat gtataaaatg ctcttaccca    5520
ctgaaccatc ttgctgcttg gtccacaagc ttagtggaag aatgctggga agtgaatagt    5580 atgttttaa atgtagttaa ccttgacttt ttgttgttgt tgctgttatt gaggccacat     5640
tttcattgtt ctgagaaaat attactattt tcctcagaca gaattatata tttatttgaa    5700
gttcatgaat tccatattat tttcctgtat ttattacaaa tagcatgctt aaacacttcc    5760
aagtagtgaa acagctgctc atgtaggaca cggattattg acagtgctgc catttatcag    5820
ccagtaatcc acttggcagg tagcacgctc atcgttatcc tttatgcaca caaagccttg    5880 tttgaattt atctttaat gagtgtcaat gaaatgaaa gagataagag ttaaaaatac        5940
aacccaaact attgtattta catttctctt ttagaagaaa cctaaagcag cattacttct    6000
tgcccatatt taataaataa catcatttac ccttgttccc tgcctccaga ctctcccata    6060
tactcctctt tcaatttat tggccccttt aaatgacata tcattacatg tatatcccta     6120
cacataagta taaccagttc agtttgtata atgttacttg catgtgtgtt ttcaatgctg    6180
atcatttggt agtggataac caatggtgtg ccctatgaag gggcagagta tttgtatcat    6240
```

```
gcttagcatt cctttgtcga ccgatgccct tgagagcctt caacccagtc agctccttcc   6300
ggtgggcgcg gggcatgact atcgtcgccg cacttatgac tgtcttcttt atcatgcaac   6360
tcgtaggaca ggtgccggca gcgctcttcc gcttcctcgc tcactgactc gctgcgctcg   6420
gtcgttcggc tgcggcgagc ggtatcagct cactcaaagg cggtaatacg gttatccaca   6480
gaatcagggg ataacgcagg aaagaacatg tgagcaaaag gccagcaaaa ggccaggaac   6540
cgtaaaaagg ccgcgttgct ggcgtttttc cataggctcc gcccccctga cgagcatcac   6600
aaaaatcgac gctcaagtca gaggtggcga acccgacag gactataaag ataccaggcg   6660
tttccccctg gaagctccct cgtgcgctct cctgttccga ccctgccgct taccggatac   6720
ctgtccgcct ttctcccttc gggaagcgtg gcgctttctc atagctcacg ctgtaggtat   6780
ctcagttcgg tgtaggtcgt tcgctccaag ctgggctgtg tgcacgaacc ccccgttcag   6840
cccgaccgct gcgccttatc cggtaactat cgtcttgagt ccaacccggt aagacacgac   6900
ttatcgccac tggcagcagc cactggtaac aggattagca gagcgaggta tgtaggcggt   6960
gctacagagt tcttgaagtg gtggcctaac tacggctaca ctagaagaac agtatttggt   7020
atctgcgctc tgctgaagcc agttaccttc ggaaaaagag ttggtagctc ttgatccggc   7080
aaacaaacca ccgctggtag cggtggtttt tttgtttgca agcagcagat tacgcgcaga   7140
aaaaaaggat ctcaagaaga tcctttgatc ttttctacgg ggtctgacgc tcagtggaac   7200
gaaaactcac gttaagggat tttggtcatg agattatcaa aaaggatctt cacctagatc   7260
cttttaaatt aaaaatgaag ttttaaatca atctaaagta tatatgagta aacttggtct   7320
gacagttacc aatgcttaat cagtgaggca cctatctcag cgatctgtct atttcgttca   7380
tccatagttg cctgactccc cgtcgtgtag ataactacga tacgggaggg cttaccatct   7440
ggccccagtg ctgcaatgat accgcgagac ccacgctcac cggctccaga tttatcagca   7500
ataaaccagc cagccggaag ggccgagcgc agaagtggtc ctgcaacttt atccgcctcc   7560
atccagtcta ttaattgttg ccgggaagct agagtaagta gttcgccagt taatagtttg   7620
cgcaacgttg ttgccattgc tacaggcatc gtggtgtcac gctcgtcgtt tggtatggct   7680
tcattcagct ccggttccca acgatcaagg cgagttacat gatccccat gttgtgcaaa   7740 aaagcggtta gctccttcgg tcctccgatc gttgtcagaa gtaagttggc cgcagtgtta   7800
tcactcatgg ttatggcagc actgcataat tctcttactg tcatgccatc cgtaagatgc   7860
ttttctgtga ctggtgagta ctcaaccaag tcattctgag aatagtgtat gcggcgaccg   7920
agttgctctt gcccggcgtc aatacgggat aataccgcgc cacatagcag aactttaaaa   7980
gtgctcatca ttggaaaacg ttcttcgggg cgaaaactct caaggatctt accgctgttg   8040
agatccagtt cgatgtaacc cactcgtgca cccaactgat cttcagcatc ttttactttc   8100
accagcgttt ctgggtgagc aaaaacagga aggcaaaatg ccgcaaaaaa gggaataagg   8160
gcgacacgga aatgttgaat actcatactc ttcctttttc aatattattg aagcatttat   8220
cagggttatt gtctcatgag cggatacata tttgaatgta tttagaaaaa taaacaaata   8280
ggggttccgc gcacatttcc ccgaaaagtg ccacctgacg cgcccgtag cggcgcatta   8340 agcgcggcgg gtgtggtggt tacgcgcagc gtgaccgcta cacttgccag cgccctagcg   8400
cccgctcctt tcgctttctt cccttccttt ctcgccacgt tcgccggctt tccccgtcaa   8460
gctctaaatc gggggctccc tttagggttc cgatttagtg ctttacggca cctcgacccc   8520
aaaaaacttg attagggtga tggttcacgt agtgggccat cgccctgata cggtttttt   8580 cgcccttga cgttggagtc cacgttcttt aatagtggac tcttgttcca aactggaaca   8640
```

-continued

```
acactcaacc ctatctcggt ctattctttt gatttataag ggattttgcc gatttcggcc    8700
tattggttaa aaaatgagct gatttaacaa aaatttaacg cgaattttaa caaaatatta    8760
acgcttacaa tttgccattc gccattcagg ctgcgcaact gttgggaagg gcgatcggtg    8820
cgggcctctt cgctattacg ccagcccaag ctaccatgat aagtaagtaa tattaaggta    8880
cgggaggtac ttggagcggc cgcaataaaa tatctttatt ttcattacat ctgtgtgttg    8940
gtttttgtg tgaatcgata gtactaacat acgctctcca tcaaaacaaa acgaaacaaa    9000
acaaactagc aaaataggct gtccccagtg caagtgcagg tgccagaaca tttctctatc    9060
gata                                                                 9064
```

US 8,158,771 B2

HOST CELL PROTEIN KNOCK-OUT CELLS FOR PRODUCTION OF THERAPEUTIC PROTEINS

CROSS-REFERENCE TO RELATED APPLICATIONS

This application is a divisional of U.S. application Ser. No. 11/995,109, filed Jan. 9, 2008 which is a 35 U.S.C. §371 national stage application of International Patent Application PCT/EP2006/064220 (published as WO 2007/006808 A1), filed Jul. 13, 2006, which claimed priority of European Patent Application 05106401.2, filed Jul. 13, 2005; this application further claims priority under 35 U.S.C. §119 of U.S. Provisional Application 60/706,369, filed Aug. 8, 2005.

FIELD OF THE INVENTION

The present invention relates to methods for producing compositions comprising Vitamin K-dependent protein having a very low or negligible content of protein contaminants and to compositions derived from such methods. Such methods may either be used alone or in combination with other methods for the purpose of reducing the relative content of protein contaminants. The present invention is particularly relevant in the preparation of compositions of coagulation factors selected from Thrombin polypeptides (FII/FIIa), Factor X polypeptides (FX/FXa), Factor IX polypeptides FIX/FIXa), Factor VII polypeptides (FVII/FVIIa), and the anticoagulant Protein C, in particular Factor VII polypeptides.

BACKGROUND OF THE INVENTION

In the production of recombinant proteins from cultures of microorganisms or cell lines, the final production step is the recovery and optionally the concentration of the product of interest. Culture media in which the cells have been grown and which contain secreted proteins, and, in particular, cell lysates containing intracellular proteins of interest also contain, to a greater or lesser extent, other proteins produced by the cells, apart from other contaminants, such as media components, nucleic acids and the like. In order to obtain a purified protein product, it is therefore necessary to separate the protein of interest from other proteins and polypeptides and other impurities in the crude material containing the protein of interest. It is however, often difficult to remove protein contaminants comprising domains of the same nature as the polypeptide of interest.

Vitamin K-dependent proteins are distinguished from other proteins by sharing a common structural feature in their amino terminal part of the molecule. The N-terminal of these proteins, also referred to as the Gla-domain, is rich in the unusual amino acid γ-carboxy glutamic acid which is synthesized from glutamate in a Vitamin K dependent reaction catalysed by the enzyme γ-glutamyl carboxylase. Because of the presence of about 9 to 12 Gla residues, the Gla-domain is characterised by being capable of binding divalent cations such as $Ca^{2+}$. Upon binding of metal ions, these proteins undergo conformational changes which can be measured by several techniques such as circular dichroism and fluorescence emission.

The discovery of metal induced conformational changes of Gla-containing proteins (Nelsestuen et. al., J. Biol. Chem. 1976; 251, 6886-6893) together with identification of conformation specific polyclonal antibodies (Furie et al., J. Biol. Chem. 1978; 253, 8980-8987) opened the way for the introduction of conformation specific immunoaffinity chromatography. These antibodies could recognise and bind the Gla-domain in the presence of $Ca^{2+}$ ions but released the protein upon removal of $Ca^{2+}$ ions using a $Ca^{2+}$ chelator such as EDTA or citrate.

In 1980's conformation specific pseudoaffinity chromatography was developed making use of the unique property of Gla containing proteins to undergo metal induced changes in conformation. Pseudoaffinity chromatography differs from the conventional affinity chromatography in that there is no immobilized affinity ligand involved and it is performed on a conventional chromatographic matrix (Yan S. B., J. Mol. Recog. 1996; 9, 211-218). The Gla protein can be adsorbed to an anion exchange material by eliminating divalent metal ions. Subsequently, elution is performed by adding $Ca^{2+}$ to the elution buffer.

In 1986, Bjørn and Thim reported purification of rFVII on an anion exchange material taking advantage of $Ca^{2+}$-binding property of Gla-domain of FVII (Bjørn S. and Thim L., Research Dislosure, 1986, 26960-26962.). Adsorption was achieved in a buffer without $Ca^{2+}$ and elution of FVII was possible using a $Ca^{2+}$ containing buffer with low ionic strength and under mild conditions. Yan et al. have used the same principle for the purification of recombinant human Protein C (Yan S. B. et al., Bio/technology. 1990; 8, 655-661).

Brown et al. (Brown et al., J. Biol. Chem. 2000; 275, 19795-19802.) have reported monoclonal antibodies specific for Gla residues. These antibodies could recognize all of the Gla proteins tested: Factor VII, Factor IX, Factor II, Protein C, Protein S, GAS-6, bone matrix Gla protein, conantokin G. Several conformational specific antibodies raised against one Gla protein show cross reactivity with other Gla proteins (Furie B. and Furie B., J. Biol. Chem. 1979; 254, 9766-9771; Church et al., J. Biol. Chem. 1988; 263, 6259-6267).

While the presence of the Gla-domain provides an advantage for separation of Gla containing proteins from other proteins, the inventors of present invention observed that similar properties and behaviour of the Gla containing proteins makes it difficult to separate them from each other.

Proteins with a Gla-domain comprise the following proteins: GAS-6, Protein S, Factor II (Prothrombin), Factor X, Factor IX, Protein C, Factor VII, Protein Z, Transmembrane gamma-carboxyglutamic acid protein 1, Transmembrane gamma-carboxyglutamic acid protein 2, Transmembrane gamma carboxyglutamic acid protein 3, Transmembrane gamma-carboxyglutamic acid protein 4, Bone Gla protein, Matrix Gla protein, and Osteocalcin.

The need for efficiently separating a Vitamin K-dependent protein of interest, such as a Gla-domain containing polypeptide of interest, from protein contaminants is a particularly relevant issue when dealing with the purification of such polypeptides produced in cell cultures, because the host cell may produce significant amounts of protein contaminants that may cause undesirable immunogenic reactions upon use of the polypeptide.

SUMMARY OF THE INVENTION

The present invention relates in a broad aspect to the generation of compositions comprising a Vitamin K-dependent protein of interest which is devoid or substantially devoid of at least one protein contaminant expressed by the host cell.

Thus in a first aspect the present invention relates to a host cell expressing a Vitamin K-dependent protein of interest, the host cell being modified to express a substantially lower amount of at least one protein contaminant expressed endogenous by the host cell in the absence of the modification. In one embodiment the host cell is transfected with a polynucleotide construct to encode the Vitamin K-dependent protein of interest.

The term "modified" as used herein refers to a cell that has been engineered by any man-made molecular or cell biology techniques or process useful in the industry.

In a second aspect the present invention relates to a method for producing a host cell according to the invention, the method comprising the following steps in any order:
a) optionally transfecting the host cell with a polynucleotide construct encoding a Vitamin K-dependent protein of interest; and
b) modifying the host cell to express a substantially lower amount of at least one protein contaminant expressed endogenous by the host cell in the absence of the modification.

In a further aspect the present invention relates to a method for producing a composition comprising a Vitamin K-dependent protein of interest with a substantially lower amount of at least one protein contaminant expressed endogenous by the host cell in the absence of modification, the method comprising the steps of growing a host cell expressing a Vitamin K-dependent protein of interest, the host cell being modified to express a substantially lower amount of at least one protein contaminant expressed endogenous by the host cell in the absence of the modification, in a growth medium and harvesting the growth medium comprising the Vitamin K-dependent protein of interest.

In a further aspect the present invention relates to a method for producing a composition comprising a Vitamin K-dependent protein of interest with a substantially lower amount of at least one protein contaminant expressed endogenous by the host cell in the absence of modification, the method comprising the steps of:
a) producing a host cell according to the invention; and
b) growing the host cell in a growth medium and harvesting the growth medium comprising the Vitamin K-dependent protein of interest.

In a further aspect the present invention relates to a composition produced by a method for producing a composition comprising a Vitamin K-dependent protein of interest with a substantially lower amount of at least one protein contaminant expressed endogenous by the host cell in the absence of modification, the method comprising the steps of growing a host cell expressing a Vitamin K-dependent protein of interest, the host cell being modified to express a substantially lower amount of at least one protein contaminant expressed endogenous by the host cell in the absence of the modification, in a growth medium and harvesting the growth medium comprising the Vitamin K-dependent protein of interest.

In a further aspect the invention relates to modified cells expressing a Vitamin K-dependent protein of interest useful for generating compositions comprising a Vitamin K-dependent protein of interest, devoid or substantially devoid of protein contaminants expressed by the host cell.

In a further aspect the invention relates to methods for reducing or eliminating the content of at least one protein contaminant in a composition comprising a Vitamin K-dependent protein of interest wherein at least one protein contaminant expressed by the host cell is inhibited.

In a further aspect the invention relates to new nucleic acid sequences encoding protein S in CHO cell.

In a further aspect the invention relates to a new amino acid sequence of protein S in CHO cell.

BRIEF DESCRIPTION OF THE DRAWINGS

FIG. 3 illustrates down regulation of the Protein S gene in CHO-K1 cells using the synthetic made gene ZNF-PS.

FIG. 3a: The synthetic gene ZNF-PS downregulates Protein S transcription in CHO-K1 cells, determined by luciferase reporter assay. The figure shows luciferase readout from a reporter containing the Protein S promoter. The pRL-CMV (Promega, Madison) vector was used as control for transfection efficiency. ZNF-PS down regulates Protein S promoter activity by 50% in a transient transfection.

FIG. 3b: The synthetic gene ZNF-PS downregulates Protein S transcription in CHO-K1 cells, determined by real-time PCR on Protein S mRNA. The figure illustrates a realtime PCR quantitation of the Protein S mRNA in CHO-K1 transiently trans-fected with ZNF-PS. The pEGFP (Clontech, Mountain View) vector was used as control for transfection efficiency. In this experiment ZNF-PS also down regulates Protein S 50%.

DETAILED DESCRIPTION OF THE INVENTION

Figure 1:
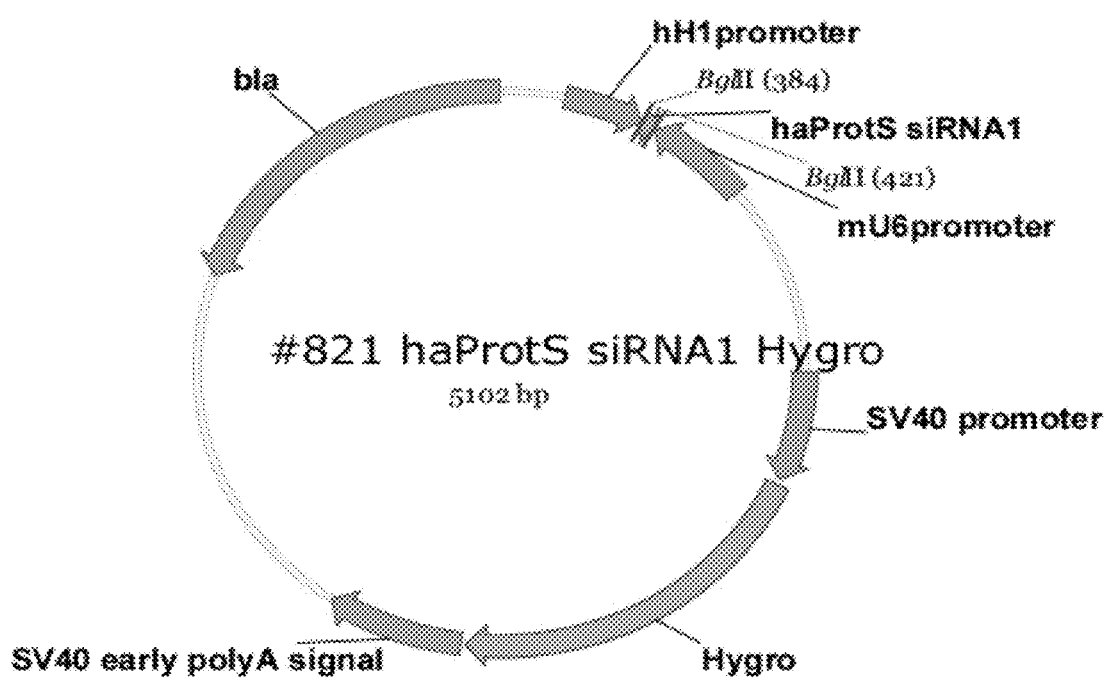
FIG. 1 illustrates the RansiRNA vector.
The vector is composed of two polymerase III promoters transcribing the siRNA template in each direction. The two RNA transcripts are complementary and anneal to form the final siRNA molecule. The vector contains a hygromycin resistance gene which makes it possible to select for stable cell clones.
Figure 2:
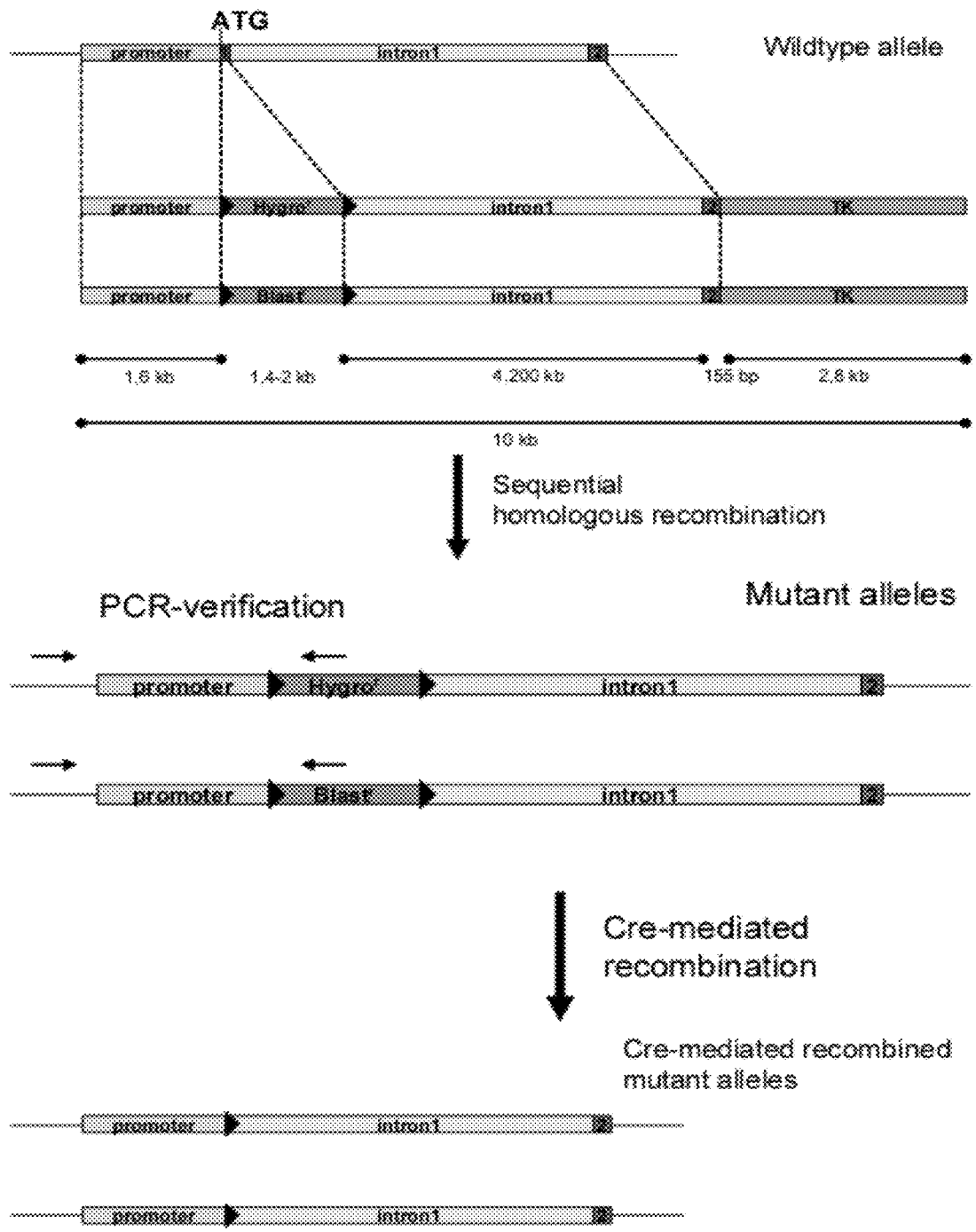
FIG. 2 illustrates steps in the Gene targeting method.
In the CHO Protein S gene targeting construct the coding part of exon 1 has been exchanged by a hygromycin or a blasticidin resistance gene for positive selection. Furthermore, the TK gene is inserted next to exon 2 for negative selection. Two cre/lox sites are flanking the resistance gene. Following homologous recombination the cell population can be screened using primers specific to promoter region outside the construct and to the resistance gene in the construct. Once the alleles have been knocked-out for wildtype Protein S, the cells may be transfected by an expression plasmids containing Cre recombinase. The Cre recombinase will recombine at the cre/lox sites and resistance genes are deleted from the cell genome.

The present invention relates to a host cell for the production of recombinant proteins, wherein this host cell is modified to express a substantially lower amount of at least one protein contaminant expressed endogenous by the host cell in the absence of the modification.

It will be understood that any method or technique for reducing expression of the contaminating protein may be used. The examples of such methods including siRNA targeting, targeted gene knock-out, transfection with a transcriptional factor, and site-specific cleavage of the DNA strands encoding protein contaminants are not to be construed limiting in any way. In principle, any molecular biology, cell biology, or selection method may be used to reduce the expression level of a particular protein contaminant. The present invention is particular useful in the situation, where the Vitamin K-dependent protein of interest is very closely related with one or more protein contaminants, such as when the protein contaminant is a second vitamin K-dependent protein. Due to the close relationship between a vitamin K-dependent protein of interest and a protein contaminant, which is a second vitamin K-dependent protein, such protein contaminant may be very difficult remove by purification methods.

The present invention further relates to compositions comprising Vitamin K-dependent proteins of interest devoid or substantially devoid of at least one protein contaminant expressed by a host cell.

In one embodiment of the invention, the Vitamin K-dependent protein of interest is selected from the group consisting of GAS-6, Protein S, Factor II (Prothrombin), Factor X, Factor IX, Protein C, Factor VII, Protein Z, Transmembrane gamma-carboxyglutamic acid protein 1, Transmembrane gamma-carboxyglutamic acid protein 2, Transmembrane gamma carboxyglutamic acid protein 3, Transmembrane gamma-carboxyglutamic acid protein 4, Bone Gla protein, Matrix Gla protein, and Osteocalcin. The Vitamin K-dependent proteins may be in either an activated or a non-activated form, such as Factor II and Factor IIa, and Factor X and Factor Xa.

In one embodiment of the invention the Vitamin K-dependent protein of interest is a coagulation factor, such as e.g. FVII or FVIIa polypeptides. In one embodiment the Vitamin K-dependent protein of interest is wild type human FVIIa.

In one embodiment of the invention, the protein contaminants is a second different Vitamin K-dependent protein. Thus, the protein of interest and the protein contaminant may both be a Vitamin K-dependent protein.

In one embodiment of the invention the protein contaminants is Protein S. In one embodiment, the protein contaminants is hamster Protein S.

In one embodiment of the invention the host cell is selected from the group consisting of CHO cells, 293 (HEK293) cells, BKH cells, HKB11 cells, SP2/0 cells, and NS0 cells.

The present invention furthermore relates to a host cell expressing a Vitamin K-dependent protein of interest, which host cell comprises a siRNA construct targeting at least one protein contaminant expressed by the host cell.

The term "siRNA" as used herein refers to small interfering RNA, sometimes known as short interfering RNA or silencing RNA known in the art of molecular biology.

In one embodiment the host cell has been modified by transfection with at least one siRNA polynucleotide construct targeting a mRNA encoding a protein contaminant expressed endogenous by the host cell.

In one embodiment the host cell expressing a Vitamin K-dependent protein of interest comprises a siRNA construct targeting at least one protein contaminant expressed by the host cell, wherein the protein contaminant is a second vitamin K-dependent protein.

In one embodiment the host cell expressing a Vitamin K-dependent protein of interest comprises a siRNA construct targeting at least one protein contaminant expressed by the host cell, wherein the protein contaminant is Protein S.

The present invention also relates to a cell expressing a Vitamin K-dependent protein of interest comprising a disrupted gene for at least one protein contaminant expressed by the host cell.

In one embodiment the host cell has been modified by disruption by gene knock-out of at least one endogenous gene encoding a protein contaminant expressed endogenous by the host cell. In one embodiment the endogenous gene encoding Protein S has been disrupted by gene knock-out of exon 1.

In one embodiment the host cell expressing a Vitamin K-dependent protein of interest comprises a disrupted gene for at least one protein contaminant expressed by the host cell, wherein the protein contaminant is a second vitamin K-dependent protein.

In one embodiment the host cell expressing a Vitamin K-dependent protein of interest comprises a disrupted gene for at least one protein contaminant expressed by the host cell, wherein the protein contaminant is Protein S.

In one embodiment the host cell expressing a Vitamin K-dependent protein of interest comprises a disrupted gene for Protein S, wherein the Protein S gene is disrupted by omission of exon 1.

In one embodiment the host cell expressing a Vitamin K-dependent protein of interest has been modified by transfection with at least one transcription factor binding to a DNA element of the gene encoding the protein contaminant expressed endogenous by the host cell.

In one embodiment the host cell expressing a Vitamin K-dependent protein of interest has been modified by transfection with at least one nuclease fusion protein for site-specific cleavage of the DNA strands encoding the protein contaminant expressed endogenous by the host cell.

The present invention furthermore relates to a cell expressing a Vitamin K-dependent protein of interest comprising a transcription factor binding to at least one protein contaminant expressed by the host cell.

In one embodiment the host cell expressing a Vitamin K-dependent protein of interest comprising a transcription factor binding to the DNA sequence encoding at least one protein contaminant, the protein contaminant is a second vitamin K-dependent protein.

In one embodiment the host cell expressing a Vitamin K-dependent protein of interest comprises a transcription factor binding to the DNA sequence encoding at least one protein contaminant, the protein contaminant is Protein S.

In one embodiment of the invention the transcription factor is a Zinc finger protein. In one embodiment of the invention the Zinc finger protein binds a DNA element comprising the sequence of SEQ ID NO 35.

In one embodiment of the invention the Zinc finger protein binds the GGAGAGGAGGGGGGG DNA element.

In one embodiment the host cell expressing a Vitamin K-dependent protein of interest is modified by random mutagenesis for disruption of at least one endogenous gene encoding a protein contaminant expressed endogenous by the host cell.

The present invention also relates to a method for reducing the content of at least one protein contaminant in a composition comprising a Vitamin K-dependent protein of interest, wherein at least one protein contaminant expressed by the host cell is inhibited.

In one embodiment the method for reducing the content of at least one protein contaminant in a composition comprising a Vitamin K-dependent protein of interest, wherein at least one protein contaminant expressed by the host cell is inhibited is a method comprising the use of siRNA.

In one embodiment the method for reducing the content of at least one protein contaminant in a composition comprising a Vitamin K-dependent protein of interest, wherein at least one protein contaminant expressed by the host cell is inhibited is a method comprising the use of Random mutagenesis.

In one embodiment the method for reducing the content of at least one protein contaminant in a composition comprising a Vitamin K-dependent protein of interest, wherein at least one protein contaminant expressed by the host cell is inhibited is a method comprising the use of Targeted knock-out.

The present invention furthermore relates to a nucleic acid sequence comprising the CHO Protein S cDNA sequence having the sequence of SEQ ID NO 3 or any functional fragments thereof.

The present invention also relates to a nucleic acid sequence comprising the CHO Protein S coding sequence having the sequence of SEQ ID NO 4 or any functional fragments thereof.

The present invention relates to an amino acid sequence comprising CHO Protein S sequence having the sequence of SEQ ID NO 5 or any functional fragments thereof.

The methods and means described herein may in principle be applied for generating compositions comprising any Vitamin K-dependent protein of interest which is devoid or substantially devoid of protein contaminants.

"Polypeptides" means any protein comprising the amino acid sequence of the wild-type protein, as well as their respective "variants", "related polypeptides", "derivatives" and "conjugates" thereof.

In particular, as used herein, the terms "Factor VII polypeptide" or "FVII polypeptide" means any protein comprising the amino acid sequence 1-406 of wild-type human Factor VIIa (i.e., a polypeptide having the amino acid sequence disclosed in U.S. Pat. No. 4,784,950), variants thereof as well as Factor VII-related polypeptides, Factor VII derivatives and Factor VII conjugates. This includes FVII variants, Factor VII-related polypeptides, Factor VII derivatives and Factor VII conjugates exhibiting substantially the same or improved biological activity relative to wild-type human Factor VIIa.

The term "Factor VII" is intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa.

Variants of Factor VII may exhibit different properties relative to human Factor VII, including stability, phospholipid binding, altered specific activity, and the like.

"Factor VII" or "Factor VIIa" within the above definition also includes natural allelic variations that may exist and occur from one individual to another. Also, degree and location of glycosylation or other post-translation modifications may vary depending on the chosen host cells and the nature of the host cellular environment.

As used herein, "wild type human FVIIa" is a polypeptide having the amino acid sequence disclosed in U.S. Pat. No. 4,784,950.

The term "Factor VII derivative" as used herein, is intended to designate a FVII polypeptide exhibiting substantially the same or improved biological activity relative to wild-type Factor VII, in which one or more of the amino acids of the parent peptide have been genetically and/or chemically and/or enzymatically modified, e.g. by alkylation, glycosylation, PEGylation, acylation, ester formation or amide formation or the like. This includes but is not limited to PEGylated human Factor VIIa, cysteine-PEGylated human Factor VIIa and variants thereof. Non-limiting examples of Factor VII derivatives includes GlycoPegylated FVII derivatives as disclosed in WO 03/31464 and US Patent applications US 20040043446, US 20040063911, US 20040142856, US 20040137557, and US 20040132640 (Neose Technologies, Inc.); FVII conjugates as disclosed in WO 01/04287, US patent application 20030165996, WO 01/58935, WO 03/93465 (Maxygen ApS) and WO 02/02764, US patent application 20030211094 (University of Minnesota).

The term "improved biological activity" refers to FVII polypeptides with i) substantially the same or increased proteolytic activity compared to recombinant wild type human Factor VIIa or ii) to FVII polypeptides with substantially the same or increased TF binding activity compared to recombinant wild type human Factor VIIa or iii) to FVII polypeptides with substantially the same or increased half life in blood plasma compared to recombinant wild type human Factor VIIa. The term "PEGylated human Factor VIIa" means human Factor VIIa, having a PEG molecule conjugated to a human Factor VIIa polypeptide. It is to be understood, that the PEG molecule may be attached to any part of the Factor VIIa polypeptide including any amino acid residue or carbohydrate moiety of the Factor VIIa polypeptide. The term "cysteine-PEGylated human Factor VIIa" means Factor VIIa having a PEG molecule conjugated to a sulfhydryl group of a cysteine introduced in human Factor VIIa.

Non-limiting examples of Factor VII variants having substantially the same or increased proteolytic activity compared to recombinant wild type human Factor VIIa include S52A-FVIIa, S60A-FVIIa (Lino et al., Arch. Biochem. Biophys. 352: 182-192, 1998); FVIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., Biotechnol. Bioeng. 48:501-505, 1995); oxidized forms of Factor VIIa (Kornfelt et al., Arch. Biochem. Biophys. 363:43-54, 1999); FVII variants as disclosed in PCT/DK02/00189 (corresponding to WO 02/077218); and FVII variants exhibiting increased proteolytic stability as disclosed in WO 02/38162 (Scripps Research Institute); FVII variants having a modified Gla-domain and exhibiting an enhanced membrane binding as disclosed in WO 99/20767, U.S. Pat. No. 6,017,882 and U.S. Pat. No. 6,747,003, US patent application 20030100506 (University of Minnesota) and WO 00/66753, US patent applications US 20010018414, US 2004220106, and US 200131005, U.S. Pat. No. 6,762,286 and U.S. Pat. No. 6,693,075 (University of Minnesota); and FVII variants as disclosed in WO 01/58935, U.S. Pat. No. 6,806,063, US patent application 20030096338 (Maxygen ApS), WO 03/93465 (Maxygen ApS), WO 04/029091 (Maxygen ApS), WO 04/083361 (Maxygen ApS), and WO 04/111242 (Maxygen ApS), as well as in WO 04/108763 (Canadian Blood Services).

Non-limiting examples of FVII variants having increased biological activity compared to wild-type FVIIa include FVII variants as disclosed in WO 01/83725, WO 02/22776, WO 02/077218, WO 03/027147, WO 04/029090, WO 05/075635, and European patent application with application number 05108713.8 (Novo Nordisk A/S), WO 02/38162 (Scripps Research Institute); and FVIIa variants with enhanced activity as disclosed in JP 2001061479 (Chemo-Sero-Therapeutic Res Inst.).

Examples of variants of factor VII include, without limitation, P10Q-FVII, K32E-FVII, P10Q/K32E-FVII, L305V-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII, L305V/K337A-FVII, L305V/V158D-FVII, L305V/E296V-FVII, L305V/M298Q-FVII, L305V/V158T-FVII, L305V/K337A/V158T-FVII, L305V/K337A/M298Q-FVII, L305V/K337A/E296V-FVII, L305V/K337A/V158D-FVII, L305V/V158D/M298Q-FVII, L305V/V158D/E296V-FVII, L305V/V158T/M298Q-FVII, L305V/V158T/E296V-FVII, L305V/E296V/M298Q-FVII, L305V/V158D/E296V/M298Q-FVII, L305V/V158T/E296V/M298Q-FVII, L305V/V158T/K337A/M298Q-FVII, L305V/V158T/E296V/K337A-FVII, L305V/V158D/K337A/M298Q-FVII, L305V/V158D/E296V/K337A-FVII, L305V/V158D/E296V/M298Q/K337A-FVII, L305V/V158T/E296V/M298Q/K337A-FVII, S314E/K316H-FVII, S314E/K316Q-FVII, S314E/L305V-FVII, S314E/K337A-FVII, S314E/V158D-FVII, S314E/E296V-FVII, S314E/M298Q-FVII, S314E/V158T-FVII, K316H/L305V-FVII, K316H/K337A-FVII, K316H/V158D-FVII, K316H/E296V-FVII, K316H/M298Q-FVII, K316H/V158T-FVII, K316Q/L305V-FVII, K316Q/K337A-FVII, K316Q/V158D-FVII, K316Q/E296V-FVII, K316Q/M298Q-FVII, K316Q/V158T-FVII, S314E/L305V/K337A-FVII, S314E/L305V/V158D-FVII, S314E/L305V/E296V-FVII, S314E/L305V/M298Q-FVII, S314E/L305V/V158T-FVII, S314E/L305V/K337A/V158T-FVII, S314E/L305V/K337A/M298Q-FVII, S314E/L305V/K337A/E296V-FVII, S314E/L305V/K337A/V158D-FVII, S314E/L305V/V158D/M298Q-FVII, S314E/L305V/V158D/E296V-FVII, S314E/L305V/V158T/M298Q-FVII, S314E/L305V/V158T/E296V-FVII, S314E/L305V/E296V/M298Q-FVII, S314E/L305V/V158D/E296V/M298Q-FVII, S314E/L305V/V158T/E296V/M298Q-FVII, S314E/L305V/V158T/K337A/M298Q-FVII, S314E/L305V/V158T/E296V/K337A-FVII, S314E/L305V/V158D/K337A/M298Q-FVII, S314E/L305V/V158D/E296V/K337A-FVII, S314E/L305V/V158D/E296V/M298Q/K337A-FVII, S314E/L305V/V158T/E296V/M298Q/K337A-FVII, K316H/L305V/K337A-FVII, K316H/L305V/V158D-FVII, K316H/L305V/E296V-FVII, K316H/L305V/M298Q-FVII, K316H/L305V/V158T-FVII, K316H/L305V/K337A/V158T-FVII, K316H/L305V/K337A/M298Q-FVII, K316H/L305V/K337A/E296V-FVII, K316H/L305V/K337A/V158D-FVII, K316H/L305V/V158D/M298Q-FVII, K316H/L305V/V158D/E296V-FVII, K316H/L305V/V158T/M298Q-FVII, K316H/L305V/V158T/E296V-FVII, K316H/L305V/E296V/M298Q-FVII, K316H/L305V/V158D/E296V/M298Q-FVII, K316H/L305V/V158T/E296V/M298Q-FVII, K316H/L305V/V158T/K337A/M298Q-FVII, K316H/L305V/V158T/E296V/K337A-FVII, K316H/L305V/V158D/K337A/M298Q-FVII, K316H/L305V/V158D/E296V/K337A-FVII, K316H/L305V/V158D/E296V/M298Q/K337A-FVII, K316H/L305V/V158T/E296V/M298Q/K337A-FVII, K316Q/L305V/K337A-FVII, K316Q/L305V/V158D-FVII, K316Q/L305V/E296V-FVII, K316Q/L305V/M298Q-FVII, K316Q/L305V/V158T-FVII, K316Q/L305V/K337A/V158T-FVII, K316Q/L305V/K337A/M298Q-FVII, K316Q/L305V/K337A/E296V-FVII, K316Q/L305V/K337A/V158D-FVII, K316Q/L305V/V158D/M298Q-FVII, K316Q/L305V/V158D/E296V-FVII, K316Q/L305V/V158T/M298Q-FVII, K316Q/L305V/V158T/E296V-FVII, K316Q/L305V/E296V/M298Q-FVII, K316Q/L305V/V158D/E296V/M298Q-FVII, K316Q/L305V/V158T/E296V/M298Q-FVII, K316Q/L305V/V158T/K337A/M298Q-FVII, K316Q/L305V/V158T/E296V/K337A-FVII, K316Q/L305V/V158D/K337A/M298Q-FVII, K316Q/L305V/V158D/E296V/K337A-FVII, K316Q/L305V/V158D/E296V/M298Q/K337A-FVII, K316Q/L305V/V158T/E296V/M298Q/K337A-FVII, F374Y/K337A-FVII, F374Y/V158D-FVII, F374Y/E296V-FVII, F374Y/M298Q-FVII, F374Y/V158T-FVII, F374Y/S314E-FVII, F374Y/L305V-FVII, F374Y/L305V/K337A-FVII, F374Y/L305V/V158D-FVII, F374Y/L305V/E296V-FVII, F374Y/L305V/M298Q-FVII, F374Y/L305V/V158T-FVII, F374Y/L305V/S314E-FVII, F374Y/K337A/S314E-FVII, F374Y/K337A/V158T-FVII, F374Y/K337A/M298Q-FVII, F374Y/K337A/E296V-FVII, F374Y/K337A/V158D-FVII, F374Y/V158D/S314E-FVII, F374Y/V158D/M298Q-FVII, F374Y/V158D/E296V-FVII, F374Y/V158T/S314E-FVII, F374Y/V158T/M298Q-FVII, F374Y/V158T/E296V-FVII, F374Y/E296V/S314E-FVII, F374Y/S314E/M298Q-FVII, F374Y/E296V/M298Q-FVII, F374Y/L305V/K337A/V158D-FVII, F374Y/L305V/K337A/E296V-FVII, F374Y/L305V/K337A/M298Q-FVII, F374Y/L305V/K337A/V158T-FVII, F374Y/L305V/K337A/S314E-FVII, F374Y/L305V/V158D/E296V-FVII, F374Y/L305V/V158D/M298Q-FVII, F374Y/L305V/V158D/S314E-FVII, F374Y/L305V/E296V/M298Q-FVII, F374Y/L305V/E296V/V158T-FVII, F374Y/L305V/E296V/S314E-FVII, F374Y/L305V/M298Q/V158T-FVII, F374Y/L305V/M298Q/S314E-FVII, F374Y/L305V/V158T/S314E-FVII, F374Y/K337A/S314E/V158T-FVII, F374Y/K337A/S314E/M298Q-FVII, F374Y/K337A/S314E/E296V-FVII, F374Y/K337A/S314E/V158D-FVII, F374Y/K337A/V158T/M298Q-FVII, F374Y/K337A/V158T/E296V-FVII, F374Y/K337A/M298Q/E296V-FVII, F374Y/K337A/M298Q/V158D-FVII, F374Y/K337A/E296V/V158D-FVII, F374Y/V158D/S314E/M298Q-FVII, F374Y/V158D/S314E/E296V-FVII, F374Y/V158D/M298Q/E296V-FVII, F374Y/V158T/S314E/E296V-FVII, F374Y/V158T/S314E/M298Q-FVII, F374Y/V158T/M298Q/E296V-FVII, F374Y/E296V/S314E/M298Q-FVII, F374Y/L305V/M298Q/K337A/S314E-FVII, F374Y/L305V/E296V/K337A/S314E-FVII, F374Y/E296V/M298Q/K337A/S314E-FVII, F374Y/L305V/E296V/M298Q/K337A-FVII, F374Y/L305V/E296V/M298Q/S314E-FVII, F374Y/V158D/E296V/M298Q/K337A-FVII, F374Y/V158D/E296V/M298Q/S314E-FVII, F374Y/L305V/V158D/K337A/S314E-FVII, F374Y/V158D/M298Q/K337A/S314E-FVII, F374Y/V158D/E296V/K337A/S314E-FVII, F374Y/L305V/V158D/E296V/M298Q-FVII, F374Y/L305V/V158D/M298Q/K337A-FVII, F374Y/L305V/V158D/E296V/K337A-FVII, F374Y/L305V/V158D/M298Q/S314E-FVII, F374Y/L305V/V158D/E296V/S314E-FVII, F374Y/V158T/E296V/M298Q/K337A-FVII, F374Y/V158T/E296V/M298Q/S314E-FVII, F374Y/L305V/V158T/E296V/M298Q-FVII, F374Y/L305V/V158T/K337A/S314E-FVII, F374Y/V158T/M298Q/K337A/S314E-FVII, F374Y/V158T/E296V/K337A/S314E-FVII, F374Y/L305V/V158T/E296V/M298Q-FVII, F374Y/L305V/V158T/M298Q/K337A-FVII, F374Y/L305V/V158T/E296V/K337A-FVII, F374Y/L305V/V158T/M298Q/S314E-FVII, F374Y/L305V/V158T/E296V/S314E-FVII, F374Y/E296V/M298Q/K337A/V158T/S314E-FVII, F374Y/V158D/E296V/M298Q/K337A/S314E-FVII, F374Y/L305V/

V158D/E296V/M298Q/S314E-FVII, F374Y/L305V/E296V/M298Q/V158T/S314E-FVII, F374Y/L305V/E296V/M298Q/K337A/V158T-FVII, F374Y/L305V/E296V/K337A/V158T/S314E-FVII, F374Y/L305V/M298Q/K337A/V158T/S314E-FVII, F374Y/L305V/V158D/E296V/M298Q/K337A-FVII, F374Y/L305V/V158D/E296V/K337A/S314E-FVII, F374Y/L305V/V158D/M298Q/K337A/S314E-FVII, F374Y/L305V/E296V/M298Q/K337A/V158T/S314E-FVII, F374Y/L305V/V158D/E296V/M298Q/K337A/S314E-FVII, S52A-Factor VII, S60A-Factor VII; R152E-Factor VII, S344A-Factor VII, T106N-FVII, K143N/N145T-FVII, V253N-FVII, R290N/A292T-FVII, G291N-FVII, R315N/V317T-FVII, K143N/N145T/R315N/V317T-FVII; and FVII having substitutions, additions or deletions in the amino acid sequence from 233Thr to 240Asn; FVII having substitutions, additions or deletions in the amino acid sequence from 304Arg to 329Cys; and FVII having substitutions, additions or deletions in the amino acid sequence from 153Ile to 223Arg.

Thus, substitution variants in a factor VII polypeptide include, without limitation substitutions in positions P10, K32, L305, M306, D309, L305, L305, F374, V158, M298, V158, E296, K337, M298, M298, S336, S314, K316, K316, F374, S52, S60, R152, S344, T106, K143, N145, V253, R290, A292, G291, R315, V317, and substitutions, additions or deletions in the amino acid sequence from T233 to N240 or from R304 to C329; or from I153 to R223, or combinations thereof, in particular variants such as P10Q, K32E, L305V, M306D, D309S, L305I, L305T, F374P, V158T, M298Q, V158D, E296V, K337A, M298Q, M298K, S336G, S314E, K316H, K316Q, F374Y, S52A, S60A, R152E, S344A, T106N, K143N, N145T, V253N, R290N, A292T, G291N, R315N, V317T, and substitutions, additions or deletions in the amino acid sequence from T233 to N240, or from R304 to C329, or from I153 to R223, or combinations thereof.

"A Vitamin K-dependent protein of interest" as used herein refers to the single Vitamin K-dependent protein product produced by the host cells, which is relevant to obtain in the most pure form. In one embodiment vitamin K-dependent protein of interest is the protein product produced in the highest amount by the host cell. In one embodiment, the Vitamin K-dependent protein of interest in transfected into the host cell.

"Composition" as used herein, means any composition, such as a liquid composition, such as an aqueous liquid composition.

The Vitamin K-dependent protein of interest is most typically one produced under cell culture conditions, i.e. the Vitamin K-dependent protein of interest is either obtained directly as a constituent of a cell culture supernatant, or obtained from a cell culture supernatant after one or more subsequent purification process steps.

Typically, the total content of protein contaminants in the non-purified composition is at least 200 ppm, such as at least 300 ppm, e.g. at least 400 ppm, or at least 500 ppm. Also typically, the total content of Protein S contaminants in the non-purified composition is at least 200 ppm, such as at least 300 ppm, e.g. at least 400 ppm, or at least 500 ppm.

"Protein contaminant" and "protein contaminants" as used herein, means protein or polypeptide constituents produced endogenously by the host cell and constituting an impurity in relation to the Vitamin K-dependent protein of interest. Thus, the Vitamin K-dependent protein of interest is obviously not be counted as a protein contaminant.

"Devoid or substantially devoid" as used herein, refers to a composition wherein the total content of a protein contaminant in the composition is at the most 500 ppm, such as at the most 100 ppm, such as at the most 10 ppm, e.g. at the most 1 ppm, or at the most 0.1 ppm. Also typically, the total content of Protein S contaminants in the composition is at the most 500 ppm, such as at the most 100 ppm, such as at the most 10 ppm, e.g. at the most 1 ppm, or at the most 0.1 ppm.

The phrase "express a substantially lower amount of at least one protein contaminant" as used herein, refers to the expression level of an endogenous protein contaminant, which is reduced by at least 30%, such as by at least 40%, such as by at least 50%, such as by at least 60%, such as by at least 80%, such as by at least 90%, such as by at least 95%, such as by at least 99%.

A particularly relevant class of protein contaminant are proteins very similar to the Vitamin K-dependent protein of interest, such as any other protein containing a Gla-domain including the proteins: GAS-6, Protein S, Factor II (Prothrombin), Factor Xa, Factor IXa, Protein C, Factor VIIa, Protein Z, Transmembrane gamma-carboxyglutamic acid protein 1, Transmembrane gamma-carboxyglutamic acid protein 2, Transmembrane gamma carboxyglutamic acid protein 3, Transmembrane gamma-carboxyglutamic acid protein 4, Matrix Gla protein, and Osteocalcin.

As a non-limiting example, Protein S is sometimes seen as an impurity in the production of recombinant FVIIa in mammalian cells. Protein S is like FVII a Vitamin K-dependent plasma glycoprotein containing an EGF-like domain and a gamma-carboxyglutamate (Gla) domain. Due to the structural similarity between FVII(a) and Protein S, it is difficult to recover FVII by means of chromatographic methods supra without contamination with Protein S. It would therefore be desirable to prevent the expression of Protein S by the host cell. This may be obtained by targeting the mRNA or the genome.

Stable expression of small interfering RNA, siRNA, is a new technology that enables reduction of targeted mRNA and thus suppression of targeted gene expression in mammalian cells (T. R. Brummelkamp, R. Bernards, and R. Agami. Science 296(5567): 550-553, 2002 & M. Mivaaishi and K Taira. Nat Biotechnol 20(5):497-200, 2002.) A number of individual siRNA have been generated in a strategy similar to the ones described in the references. Some of these siRNAs have proven useful (Example 2).

The use of random mutagenesis to introduce genomic changes in the host cells, some of which may prevent the generation of mRNA in the host cell may also be exploited. This may be achieved by treating a population of CHO cells with a mutagen such as e.g. Ethyl Methane Sulfonate, EMS, which induces point mutations in the cells. The surviving cells may exhibit altered phenotypes, because of these mutations. The cells may be seeded in a screening format (e.g. 96-well plates) to allow isolation of clonal cell populations. Following a growth period, medium may be harvested from the wells and assayed for Protein S content. Clones without Protein S expression may be isolated and used for production of Protein S-free Factor VII.

Disruption of the genome may be obtained by gene targeting or the knock-out technique (Example 3). The generation of knock-out cells is a well-described technique for eradicating expression of endogenous proteins, and a CHO knock-out cell was recently described in Yamane-Ohnukiet al. Biotechnol. Bioeng. 87 (5):614-622, 2004.

Genomic Protein S knockout plasmid was generated and transfected into CHO cells. By homologous recombination the Protein S gene in the CHO cells was disrupted. This procedure was repeated until all alleles of the Protein S gene was stably removed (Example 3).

Transcription factor engineering for transcriptional down regulation is an alternative way of modifying the gene expression (Example 4).

These methods may in theory be suitable for removing any unwanted host cell protein contaminants. For all of these methods to be applied it requires the knowledge of the gene sequence of the contaminating protein. The sequence of Protein S for Chinese Ovary Hamster, CHO, is not public available and a cloning of CHO Protein S cDNA was performed as described in Example 1 and disclosed as SEQ ID NO 1. The CHO Protein S coding sequence and the CHO Protein S amino acid sequence are disclosed as SEQ ID NO 2 and 3 respectively.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EMBODIMENTS OF THE INVENTION

1. A composition comprising a Vitamin K-dependent protein of interest devoid or substantially devoid of at least one protein contaminant expressed by a host cell.
2. The composition according to embodiment 1, wherein the Vitamin K-dependent protein of interest is selected from the group consisting of GAS-6, Protein S, Factor II (Prothrombin), Factor X, Factor IX, Protein C, Factor VII, Protein Z, Transmembrane gamma-carboxyglutamic acid protein 1, Transmembrane gamma-carboxyglutamic acid protein 2, Transmembrane gamma carboxyglutamic acid protein 3, Transmembrane gamma-carboxyglutamic acid protein 4, Bone Gla protein, Matrix Gla protein, and Osteocalcin.
3. The composition according to embodiment 1, wherein at least one of said protein contaminants is a vitamin K-dependent protein.
4. The composition according to embodiment 1, wherein at least one of said protein contaminants is Protein S.
5. The composition according to embodiment 1, wherein the host cell is selected from the group consisting of CHO cells, 293 (HEK293) cells, BKH cells, HKB11 cells, SP2/0 cells, and NS0 cells.
6. A cell expressing a Vitamin K-dependent protein of interest according to any of embodiments 1-5 further comprising a siRNA construct targeting at least one protein contaminant expressed by the host cell.
7. The cell according to embodiment 6, wherein said at least one protein contaminant is a vitamin K-dependent protein.
8. The cell according to any of embodiments 6-7, wherein said at least one protein contaminant is Protein S.
9. A cell expressing a Vitamin K-dependent protein of interest according to any of embodiments 1-5 further comprising a disrupted gene for at least one protein contaminant expressed by the host cell.
10. The cell according to embodiment 9, wherein said at least one protein contaminant is a vitamin K-dependent protein
11. The cell according to any of embodiments 9-10, wherein said at least one protein con-taminant is Protein S.
12. The cell according to any of embodiments 9-11, wherein the Protein S gene is disrupted by omission of exon 1
13. A cell expressing a Vitamin K-dependent protein of interest according to any of embodiments 1-5 further comprising a transcription factor binding to at least one protein contaminant expressed by the host cell.
14. The cell according to embodiment 13, wherein said at least one protein contaminant is a vitamin K-dependent protein
15. The cell according to any of embodiments 13-14, wherein said at least one protein contaminant is Protein S.
16. The cell according to any of embodiments 13-15, wherein the transcription factor is a Zinc finger protein.
17. The cell according to any of embodiments 15-16, wherein the Zinc finger protein binds the GGAGAGGAGGGGGGG DNA element.
18. A method for reducing the content of at least one protein contaminant in a composition comprising a Vitamin K-dependent protein of interest wherein at least one protein contaminant expressed by the host cell is inhibited
19. The method according to embodiment 18, wherein the method comprises the use of siRNA.
20. The method according to embodiment 18, wherein the method comprises the use of Random mutagenesis.
21. The method according to embodiment 18, wherein the method comprises the use of Targeted knock-out.
22. A nucleic acid sequence comprising the CHO Protein S cDNA sequence having the sequence of SEQ ID NO 1.
23. A nucleic acid sequence comprising the CHO Protein S coding sequence having the sequence of SEQ ID NO 2.
24. An amino acid sequence comprising CHO Protein S sequence having the sequence of SEQ ID NO 3.

Further Embodiments of the Invention

1a. A host cell expressing a Vitamin K-dependent protein of interest, said host cell being modified to express a substantially lower amount of at least one protein contaminant expressed endogenous by said host cell in the absence of said modification.
2a. The host cell according to embodiment 1a, wherein said Vitamin K-dependent protein of interest is selected from the group consisting of GAS-6, Protein S, Factor II (Prothrombin), Factor X, Factor IX, Protein C, Factor VII, Protein Z, Transmembrane gamma-carboxyglutamic acid protein 1, Transmembrane gamma-carboxyglutamic acid protein 2, Transmembrane gamma carboxyglutamic acid protein 3, Transmembrane gamma-carboxyglutamic acid protein 4, Bone Gla protein, Matrix Gla protein, and Osteocalcin.
3a. The host cell according to any one of embodiments 1a-2a, wherein said protein contaminants is a second vitamin K-dependent protein.
4a. The host cell according to any one of embodiments 1a-3a, wherein said protein contaminant is Protein S.
5a. The host cell according to any one of embodiments 1a-4a, wherein the host cell is selected from the group consisting of CHO cells, 293 (HEK293) cells, BKH cells, HKB11 cells, SP2/0 cells, and NS0 cells.
6a. The host cell according to any one of embodiments 1a-5a, wherein said cell has been modified by transfection with at least one siRNA polynucleotide construct targeting a mRNA encoding a protein contaminant expressed endogenous by said host cell.
7a. The host cell according to any one of embodiments 1a-6a, wherein said cell has been modified by disruption by gene knock-out of at least one endogenous gene encoding a protein contaminant expressed endogenous by said host cell.
8a. The host cell according to embodiment 7a, wherein the endogenous gene encoding Protein S has been disrupted by gene knock-out of exon 1.
9a. The host cell according to any one of embodiments 1a-8a, wherein said cell has been modified by transfection with at least one transcription factor binding to a DNA element of the gene encoding said protein contaminant expressed endogenous by said host cell.

10a. The host cell according to embodiment 9a, wherein said transcription factor is a Zinc finger protein.

11a. The host cell according to embodiment 10a, wherein said Zinc finger protein binds a DNA element comprising the sequence of SEQ ID NO 35.

12a. The host cell according to any one of embodiments 1a-11a, wherein said cell has been modified by random mutagenesis for disruption of at least one endogenous gene encoding a protein contaminant expressed endogenous by said host cell.

13a. A method for producing a host cell according to any one of embodiments 1a-12a, said method comprising the following steps in any order:
a) optionally transfecting said cell with a polynucleotide construct encoding a Vitamin K-dependent protein of interest; and
b) modifying said cell to express a substantially lower amount of at least one protein contaminant expressed endogenous by said host cell in the absence of said modification.

14a. The method according to embodiment 13a, wherein said Vitamin K-dependent protein of interest is selected from the group consisting of GAS-6, Protein S, Factor II (Prothrombin), Factor X, Factor IX, Protein C, Factor VII, Protein Z, Transmembrane gamma-carboxyglutamic acid protein 1, Transmembrane gamma-carboxyglutamic acid protein 2, Transmembrane gamma carboxyglutamic acid protein 3, Transmembrane gamma-carboxyglutamic acid protein 4, Bone Gla protein, Matrix Gla protein, and Osteocalcin.

15a. The method according to any one of embodiments 13a-14a, wherein said protein contaminants is a second vitamin K-dependent protein.

16a. The method according to any one of embodiments 13a-15a, wherein said protein contaminant is Protein S.

17a. The method according to any one of embodiments 13a-16a, wherein the host cell is selected from the group consisting of CHO cells, 293 (HEK293) cells, BKH cells, HKB11 cells, SP2/0 cells, and NS0 cells.

18a. The method according to any one of embodiments 13a-17a, wherein said cell has been modified by transfection with at least one siRNA polynucleotide construct targeting a mRNA encoding a protein contaminant expressed endogenous by said host cell.

19a. The method according to any one of embodiments 13a-18a, wherein said cell has been modified by disruption by gene knock-out of at least one endogenous gene encoding a protein contaminant expressed endogenous by said host cell.

20a. The method according to embodiment 19a, wherein the endogenous gene encoding Protein S has been disrupted by gene knock-out of exon 1.

21a. The method according to any one of embodiments 13a-20a, wherein said cell has been modified by transfection with at least one transcription factor binding to a DNA element of the gene encoding said protein contaminant expressed endogenous by said host cell.

22a. The method according to embodiment 21a, wherein said transcription factor is a Zinc finger protein.

23a. The method according to embodiment 22a, wherein said Zinc finger protein binds a DNA element comprising the sequence of SEQ ID NO 35.

24a. The method according to any one of embodiments 13a-23a, wherein said cell has been modified by random mutagenesis for disruption of at least one endogenous gene encoding a protein contaminant expressed endogenous by said host cell.

25a. A method for producing a composition comprising a Vitamin K-dependent protein of interest with a substantially lower amount of at least one protein contaminant expressed endogenous by said host cell in the absence of modification, said method comprising the steps of:
a) producing a host cell according to any one methods of embodiments 13a-24a; and
b) growing said host cell in a growth medium and harvesting said growth medium comprising said Vitamin K-dependent protein of interest.

26a. A composition produced by the method according to embodiment 25a.

27a. A nucleic acid sequence comprising the sequence of SEQ ID NO 1.

28a. A nucleic acid sequence comprising the sequence of SEQ ID NO 2.

29a. An amino acid sequence comprising the sequence of SEQ ID NO 3.

EXAMPLES

Example 1

Cloning of CHO Protein S cDNA

The Chinese Hamster Ovary, CHO, Protein S cDNA sequence was not known from any nucleotide or protein database but was expected to have high identity to the nucleotide sequence of Protein S from other rodents.

CHO Protein S PCR fragments were generated from CHO cDNA using primers designed from alignment between mouse and rat Protein S cDNA sequences or genomic sequences. The cDNA fragments were sequenced and assembled to form a full-length coding sequence for the CHO Protein S gene. The full-length CHO Protein S cDNA was cloned by PCR using the primers "CHO ProtS forward" and "CHO ProtS reverse" and CHO-K1 derived cDNA as template.

The predicted CHO Protein S amino acid sequence has 90.5% identity to mouse Protein S and 90.7% identity to rat Protein S.

```
CHO ProtS forward (SEQ ID NO 1):
5'-GCCCAGGCTCGCAGCTCCTCTGG-3'

CHO ProtS reverse (SEQ ID NO 2):
5'-CAGGTGACACCTGCCAGCTGGTG-3'

CHO Protein S cDNA sequence (SEQ ID NO 3):
gcccaggctcgcagctcctctgggcggagcgccggctcggtccccgctgc gccagccgtgatccccggcagcctgctcagcaatgagggtcctgagcgcg cgctgtcggctactgctggtatgcctagccctggtgctgccagcctcgga gacaaactttttgtcaaaagaacatgcctcgcaagtcctggtgaggaagc gccgcgcaaataccttgcttgaagaaactaaaaagggcaatcttgaaaga gaatgcatcgaagagctctgcaataaagaggaagccagggaggtctttga aaacaatcccgaaacggattattttttatccaaaatatttgggttgtctgg gcatgttccgtgctggcctgttcagtgctgcgcggcagtctgttaatgct taccccgacctcaggagctgtgtcaatgccatcccagaccaatgtgatcc tatgccatgcaatgaagatgggtatctgagctgcaaagatggccaagctg ctttcacatgcatctgcaaaccaggatggcaaggggacaaatgccagttt
```

-continued gatgtaaatgaatgtaaagatcccttaaatgtaaatgggggctgcagcca gatttgtgacaacactcctggaagttaccactgctcctgcagaagtggct ttgctatgcttttcaaacaaaaaagactgcaaagatgtggatgaatgctct atgaagcccagtgtttgtggctcagctgtgtgcaagaacactccaggaga ctatgagtgtgaatgtcctgacggctacagatatgatccctcatcgaagt cttgcaaagatgtggacgaatgctctgagaacatgtgtgctcaattgtgt gtcaattaccctggaggctactcttgttactgtgatggaaagaaaggatt caagcttgcccaagatcagaagagttgtgagggtattccagtgtgccttc ccttgaaccttgacaaaaattatgaattattgtacttggctgagcagttt gtaggagttgtcttatatctgaaatttcgtttgccagaaattaccagatt ttcagctgaatttgattttcggacatatgattcagagggcatcatcctgt atgcagaatctcttgatcactcaaattggctcctgattgcacttcgtgat ggaaaaattgaagttcagtttaagaatgagttttcaacccaaatcacaac cggaggcaatgttattaacaatggtaaatggaacatggtatccgtggaag aattagacgacagtgttagcattaaaatagctaaagaagctgtgatgaat ataaataaatttgggagcctctttaaacctacagatggatttctggacac caaaatatactttgcaggattacctcgggtagtggaaagtgcactcatta aaccgattaaccctcgtctggatggatgtatacgaggctggaacttgatg aacaaggagctttaggtgcaaaggaaattattcaaggaaaacaaaataag cattgcttcctcatggtggagaagggctcctactaccctggttctggaat tgctcggttcagcatagattacaataatgtaaccaatgcagagggctggc aaataaatgtgaccttgaatattcgtccatccactgcactggaattatg cttgccttggtttctggagacaaagtgcccttgccttgtccttggtggg ctccagctctgaaaattctcaggatattgtggtatttgttgaaaattcag tggtggctcgaatggaggccataactctgtgttctgaccagcaatcccaa ctgaaatgtaatgttaacagacatggcctagagctatggagcccactgaa gaaagatgtcatctactctaaagatattcaaggacaactagcagtcttgg acaaagcaatgaaggaaacgtggccacttatctgggtggcattccagat cttccttcagtgccacgccagtgaatgccttctacagtggctgcatgga agtgaacatcaacggggtgcagttggatctggatgaagccatttctaaac ataatgacatcagagctcactcatgtccttcagttaagaaaatccagaag aacgtctaatgtctgttttctgtgcttataatgccccttccttgtaatt atgctcacgccccctatcaccagctggcaggtgtcacctgtgaagtgcaat gtttgaaatgatgtggtactttgtccttcagattttttgttatataaacca cgttttttttttttttttttaaagtctttcttctattgctgtctagaaatta aataa CHO Protein S coding sequence (SEQ ID NO 4):
atgagggtcctgagcgcgcgctgtcggctactgctggtatgcctagccct ggtgctgccagcctcggagacaaactttttgtcaaaagaacatgcctcgc aagtcctggtgaggaagcgccgcgcaaataccttgcttgaagaaactaaa aagggcaatcttgaaagagaatgcatcgaagagctctgcaataaagagga agccagggaggtctttgaaaacaatcccgaaacggattattttttatccaa aatatttgggttgtctgggcatgttccgtgctggcctgttcagtgctgcg cggcagtctgttaatgcttaccccgacctcaggagctgtgtcaatgccat cccagaccaatgtgatcctatgccatgcaatgaagatgggtatctgagct gcaaagatggccaagctgctttcacatgcatctgcaaaccaggatggcaa ggggacaaatgccagtttgatgtaaatgaatgtaaagatcccttaaatgt aaatgggggctgcagccagatttgtgacaacactcctggaagttaccact gctcctgcagaagtggcttttgctatgcttttcaaacaaaaaagactgcaaa gatgtggatgaatgctctatgaagcccagtgtttgtggctcagctgtgtg caagaacactccaggagactatgagtgtgaatgtcctgacggctacagat atgatccctcatcgaagtcttgcaaagatgtggacgaatgctctgagaac atgtgtgctcaattgtgtgtcaattaccctggaggctactcttgttactg tgatggaaagaaaggattcaagcttgcccaagatcagaagagttgtgagg gtattccagtgtgccttcccttgaaccttgacaaaaattatgaattattg tacttggctgagcagtttgtaggagttgtcttatatctgaaatttcgttt gccagaaattaccagattttcagctgaatttgattttcggacatatgatt cagagggcatcatcctgtatgcagaatctcttgatcactcaaattggctc ctgattgcacttcgtgatggaaaaattgaagttcagtttaagaatgagtt ttcaacccaaatcacaaccggaggcaatgttattaacaatggtaaatgga acatggtatccgtggaagaattagacgacagtgttagcattaaaatagct aaagaagctgtgatgaatataaataaatttgggagcctctttaaacctac agatggatttctggacaccaaaatatactttgcaggattacctcgggtag tggaaagtgcactcattaaaaccgattaaccctcgtctggatggatgtata cgaggctggaacttgatgaaacaaggagctttaggtgcaaaggaaattat tcaaggaaaacaaaataagcattgcttcctcatggtggagaagggctcct actaccctggttctggaattgctcggttcagcatagattacaataatgta accaatgcagagggctggcaaataaatgtgaccttgaatattcgtccatc cactggcactggaattatgcttgccttggtttctggagacaaagtgccct ttgccttgtccttggtgggctccagctctgaaaattctcaggatattgtg gtatttgttgaaaattcagtggtggctcgaatggaggccataactctgtg ttctgaccagcaatcccaactgaaatgtaatgttaacagacatggcctag agctatggagcccactgaagaaagatgtcatctactctaaagatattcaa ggacaactagcagtcttggacaaagcaatgaaggaaacgtggccactta tctgggtggcattccagatctttccttcagtgccacgccagtgaatgcct tctacagtggctgcatggaagtgaacatcaacggggtgcagttggatctg gatgaagccatttctaaacataatgacatcagagctcactcatgtccttc agttaagaaaatccagaagaacgtctaa CHO Protein S amino acid sequence (SEQ ID NO 5):
mrvlsarcrlllvclalvlpasetnfiskehasqvlvrkrrantlleetk kgnlerecieelcnkeearevfennpetdyfypkylgclgmfraglfsaa rqsvnaypdlrscvnaipdqcdpmpcnedgyisckdgqaaftcickpgwq -continued

```
gdkcqfdvneckdplnvnggcsqlcdntpgsyhcscrsgfamlsnkkdck dvdecsmkpsvcgsavckntpgdyececpdgyrydpssksckdvdecsen mcaqlcvnypggyscycdgkkgfklaqdqkscegipvclplnldknyell ylaeqfvgvvlylkfrlpeitrfsaefdfrtydsegiilyaesldhsnwl lialrdgkievqfknefstqittggnvinngkwnmvsveelddsvsikia keavmninkfgslfkptdgfldtkiyfaglprvvesalikpinprldgci rgwnlmkqgalgakeiiqgkqnkhcflmvekgsyypgsgiarfsidynnv tnaegwqinvtlnirpstgtgimlalvsgdkvpfalslvgsssensqdiv vfvensvvarmeaitlcsdqqsqikcnvnrhglelwspikkdviyskdiq gqlavldkamkgnvatylggipdlsfsatpvnafysgcmevningvqldl deaiskhndirahscpsvkkiqknv
```

Example 2

Cho Protein S mRNA Degradation by Use of Small Interfering RNA

The mRNA of Protein S in Chinese Hamster Ovary (CHO) cells can be degraded by the introduction of small interfering RNA, siRNA, into the cells. siRNA is a short double-stranded RNA molecule that may separate inside the cell and the antisense part of the molecule may hybridize to a complementary mRNA and induce cleavage of this mRNA by a process in which the Dicer nuclease plays a key role. The effect of siRNA is described in Elbashir-S M et al., Nature 411 (2001) 494-498. siRNA may be synthesized as single-stranded RNA and subsequently annealed to form the double-stranded siRNA molecule. The siRNA molecule may subsequently be transiently transfected into cells and exert its function. Alternatively, siRNA may be expressed as a hairpin molecule under regulation of a Polymerase III promoter as described in Brummelkamp T R; Bernards R; Agami R, *Science* 296 (2002) 550-553.

A vector that permits the transcription of each of two complementary strands by individual promoters was developed in our laboratory. The vector is called RansiRNA because random DNA can be inserted into it and both strands of the insert can be transcribed. The RansiRNA vector contains the human H1 polymerase III promoter and the mouse U6 polymerase III promoter. The two promoters are pointed towards the siRNA template from each direction, transcribing the sense and antisense strand of the siRNA molecule, respectively. The vector also harbors the hygromycin drug resistance gene. The RansiRNA vector is similar, but not identical, to the pHippy vector described by Kaykas & Moon (Kaykas-A & Moon-R T, BMC Cell Biology Vol. 5 (1) pp. 16 (2004).

Several target siRNA sequences were selected from the CHO Protein S coding sequence, only targets containing the sequence AGN$_{17}$CT (SEQ ID NO 6) were chosen. Each target sequence were purchased as two complementary DNA oligonucleotides extended with A's 5' to the target and T's 3' the target which serve as termination signal when transcribed in reverse and forward direction. The oligonucleotides also harbor a four base-pair 5'-overhang which is compatible with the Bgl II restriction site (GATC). The annealed oligonucleotides are cloned into the BglII-site of the RansiRNA-hygro vector.

The specified siRNA constructs were stably transfected into a CHO K1 cell line expressing a human FVII analogue. Cells were plated in 6-well plates at density of $2\times10^5$ c/well in complete medium (DMEM medium containing 10% FBS, non-essential amino acids and vitamin K). After two days the cells were transfected at 90% confluency. Transfection using Lipofectamine2000 (Invitrogen) was performed according to recommendations from the manufacturer. After 48 hours the cells were transferred to selection medium, which was composed of complete medium additionally supplemented with 300 ug/ml hygromycin. After selection for 14 days, cells were cloned by limiting dilution. After clones had grown up the FBS containing complete medium was changed to serum free medium (PF CHO supplemented with vitamin K, Hyclone) in order to avoid detection of bovine protein S in the following ELISA. The supernatant from approximately 100 clones for each siRNA construct were screened by protein S ELISA using human protein S as standard. The same supernatant was also screened by a human FVII ELISA. The clones that had the lowest expression of protein S and that had not lost the expression of FVII were further characterized. Clones that had down regulated the expression of protein S to the level of only 10% of the expression level exhibited by the parental CHO K1 FVII expressing cell line were isolated.

```
siRNA target sequences
#821 siRNA1 target (SEQ ID NO 7):
5'-agtgtgaatgtcctgacggct-3'

#821 siRNA1 upper oligo (SEQ ID NO 8):
5'-gatctaaaaaagtgtgaatgtcctgacggcttttta-3'

#821 siRNA1 lower oligo (SEQ ID NO 9):
5'-gatctaaaaaagccgtcaggacattcacactttttta-3'

#822 siRNA2 target (SEQ ID NO 10):
5'-agctgcaaagatggccaagct-3'

#822 siRNA2 upper oligo (SEQ ID NO 11):
5'-gatctaaaaaagctgcaaagatggccaagcttttta-3'

#822 siRNA2 lower oligo (SEQ ID NO 12):
5'-gatctaaaaaagcttggccatctttgcagcttttta-3'

#835 siRNA4 target (SEQ ID NO 13):
5'-agaacatgcctcgcaagtcct- 3'

#835 siRNA4 upper oligo (SEQ ID NO 14):
5'-gatctaaaaaagaacatgcctcgcaagtcctttttta-3'

#835 siRNA4 lower oligo (SEQ ID NO 15):
5'-gatctaaaaaaggacttgcgaggcatgttcttttta-3'

#836 siRNA5 target (SEQ ID NO 16):
5'-agaaactaaaaagggcaatct-3'

#836 siRNA5 upper oligo (SEQ ID NO 17):
5'-gatctaaaaaagaaactaaaaagggcaatcttttta-3'

#836 siRNA5 lower oligo (SEQ ID NO 18):
5'-gatctaaaaaagattgcccttttttagtttcttttta-3'

#837 SiRNA6 target (SEQ ID NO 19):
5'-agccagatttgtgacaacact-3'

#837 SiRNA6 upper oligo (SEQ ID NO 20):
5'-gatctaaaaaagccagatttgtgacaacactttttta-3'

#837 SiRNA6 lower oligo (SEQ ID NO 21):
5'-gatctaaaaaagtgttgtcacaaatctggctttttta-3'
```

Example 3

Gene Targeting of CHO Protein S

A definitive way of abolishing protein expression of Protein S is to disrupt the gene. The technique of "gene targeting" or "gene knock-out" in mice has been known for many years. Gene targeting in cultured cells is also well established, and an example of a CHO knock-out cell was recently described in Yamane-Ohnukiet et al. Biotechnology and Bioengineering, 87(5): 614-622, 2004.

We predicted the exon structure of the CHO Protein S gene by an alignment of the CHO Protein S cDNA to the human gene. Primers designed to bind in exon 1 and exon 2 of CHO Protein S was used in a Polymerase Chain Reaction, PCR, the template was CHO genomic DNA. The amplified 4,4 kb product was sequenced. Primers binding exon 2 and exon 3 was used to PCR amplify intron 2. An amplified fragment of 3.5 kb harboring intron 2 was cloned and sequenced.

The regions upstream of exon 1 from mouse and rat Protein S were aligned and sequence stretches with high identity were used to design oligonucleotide primers for use in PCR. A 1650 bp 5'UT/promoter band was cloned and sequenced. The gene targeting construct will combine the "1.6 kb 5' UT/promoter fragment", "Plox-PGK-hygromycin resistance gene-Plox", "intron 1", "exon 2" and "PGK-TK". This construct is omitting the coding sequence from exon 1 in CHO Protein S, encoding the amino acids MRVLSVRCRLLLVCLALVL-PASETN (SEQ ID NO 22). A second construct containing the blasticidin drug resistance gene can be made in a similar way.

The "hygromycin"-gene targeting construct can electroporated into CHO cells and cells plated in dishes. The next days the cells are exposed to 600 microg/ml hygromycin and 1 micromolar ganciclovir. The clones are now selected for hygromycin resistance gene and against herpes simplex thymidine kinase gene. After colonies appeared they will be transferred to 96 wells plates. The cells grow to confluence and duplicates of the plates will be made. Genomic DNA is harvested from the cell clones and PCR-reactions using a hygromycin resistance gene specific primer and a primer 3' the promoter present in the construct are performed. Clones with a positive PCR-band are grown in flasks and a Southern blot will be made to verify the PCR result.

Second, the targeting construct harboring the blasticidin resistance gene are electroporated into the hemizygous CHO cells whereafter the cells are selected for the blasticidin resistance gene and against thymidine kinase gene using 10 microg/ml blasticidin and 1 micro-molar ganciclovir. Again, cell clones are PCR verified using a blasticidin resistance gene specific primer and a primer 3' to the promoter present in the construct. Positive clones are again tested by Southern blots. Homozygous disruptants are transfected with a Cre recombinase expressing plasmid. Cre recombinase will recombine the lox sites and remove the drug-resistance genes.

```
Intron 1 primers:
CHO-protein-S-exon1-forw2 (SEQ ID NO 23):
5'-CTGCTGGTATGCCTAGCCCTGGTG-3'

CHO-protein-S-exon2-rev2 (SEQ ID NO 24):
5'-TGCAGAGCTCTTCGATGCATTCTC-3'

Intron 2 primers:
CHO-protein-S-exon2-forw2 (SEQ ID NO 25):
5'-AAGG GCAATCTTGAAAGAGAATGC-3'

CHO-protein-S-exon3rev (SEQ ID NO 26):
5'-CCAAATATTTTGGATAAAAATAATC-3'

5'UT/promoter primers:
PS-CHO promoter f2 (SEQ ID NO 27):
5'-AARCAACCCCTTTTGACCAT-3'

CHO-protein-S.promoterRev1 (SEQ ID NO 28):
5'-CCCAGAGGAGCTGCGAGCCTG-3'

5'UT/promoter (immediately 5' to coding sequence)
(SEQ ID NO 29):
aarcaaccccttttgaccatacacatttctactctttgtgtttgctggag ctgttttctccccacactcaaccccctttgctgaagcctggaacttgctt tccacagcttaagttgttataggtttcaatcatctgtccacctccctgac tttcataattttgtgaaatcccttgcatatatatatgggactaaatatta ttttctcctggttgtccataatagattaatttaattcctaaacaaagaac agaacatagattggtatagtagaagagtttcccttctccctactgcatga atggaaattccccaaaccatccttatcagagaaattaactcacatactag tcacctttcattcagctggatgacaaaatcattttaaaaaaagagaataa agaaaacagataagaacaactagatctaggaataatacttaaaatatgat tctgcttagtaggtttcattcacacacctagaaaaaaaaatcagtcaatg tttcctttgggcagaaaatgagcaataatgggtatgcattgaccactact gttggacatagccttattgcttcatatagcatctattcaaagtctcagat caacactatgaaaacctgtcatctctgtattagatgatgtgactgggggct gtaaagggtaagctcttttcttacagctatacaacaacgctaagaccaag ttctgtgctttgagcccaggcagtttagtttcccaggagcaacctaaagc ctgattcacaggcatatgtatgatccaaactgaatggtagtacatcaata ccaaaacaatctattggtggaaacacaccataggtgatcgaaatactcca ttttcttttcctctcatgacttctgttctgagcagtcctcttcctaaagt ctacattgtcttctgagttcaggctgacatcttgacatcctcctggctgg cacagtctctggacaaggagggaagaaggagagaaggggaaagggagagg aggggggagggagagaaagaatgggaagaggaaggatatgaaagagaga agagaggagggaaggcgggaggaagggagggagggagggagggagagagg gagagagaggagagagagagagagagagagagagagagagagagagagag agagagagagagagagggagagggagagagagacagagagagagagaggg agagggagagagagagagagagagagagagagagagagagagagagagag tgaggagagagagagagttttcttcaccattggacattcctaaagaaa agaagtaaatgcaggattggggacagtgacagaggacctctgataaactt tctgaggcctctgacctcactctctcggagccctcctccaccacccaccc cccccctccctagctgagaaaagcttccaggaaatgtcccagtcatcgct tcccctcccgggctggggctgggagcgggcggtcccctcaggccagggc tgctccggccgcgctcgggcagggccacaacagagctgggaaagctgagc ccaggctcgcagctcctctgggcggagcgccggctcggtccccgctgcgc cagccgtgatccccggcagcctgctcagca
```

-continued exon1 (SEQ ID NO 30):
atgagggtcctgagcgtacgctgtcggctactgctggtatgcctagccct ggtgctgccagcctcggagacaaac intron1 (SEQ ID NO 31):
tgtaagtaatccatacctcctggcttctccattccctatgtgccccggct tgaagattttccactaggctgtttgctgcctcctaagtttccagtaagtc cgccaccattcagagagtcgcggcagcctgggtctggtgggcagtgtaaa ggtgggacaggatcaaagcttgccttgctttgagaaccattgtccacagg acttgattccagaacccgggtgacactaagtgtcaaaggaattgcttgaa catagtcctaaatattgctaggaaagctaagtcaagcctgttgccctcct cccgtttacaagagtgccccagcccgcaccctctcctgcggctaaccttc cttttgcaatttctggacttttgaacttgattgactggtctcacattgaca aactgtttggggactgctggggtgttacatatgattctctaaccttgata taagaaatagctgttggatgttaccttgtaccgaggatcattttctgagg gttttgactgttgccgcttttgagatggcagcaagaattctgtacaacaca cacattttgtgtttcttggtctttcctcttcccattctcagattccggg cagtatatcgagttttctcttagaaatataaaacgaaccacaaggtttta gtacattttaatggtcaattaaattgttttagaagcttaaatatgttca taattaacactgctttcttttgctcttttgtagtcccagtcactggcatg ggagcaataactgtataacaaataccacttaggtcactgcgagcaccaaa gaaacttttcaaagatggtaattaagtaggagtttgctggaattgcaagt ttttattaattagtaaggaatctagcctgatattttttaaatgtctaacta agttaaagaccagaatgaaactggttcactttttattgaggataaacaag ttacagttataaagcctcaacaatcaaagccctacgatgaagcagcgtgt gactgtatgcacatgatctatcttgttcagaggaacaatcaaacattttc agatagcatcagggcggtggtggtactcgcctataatcctagcaaagtca gaggcaagcagatctctgtgttcaaggccagcctagtctacagagtgagt tccaggacaactggggctacacagagaaacctgtctcagagaaaacaaa ataaaaccaaattcagatagctggtgtttgggaaaagagcaaaagacagc agtgctggccacacagagagtagacaagttcattctacaaggacatcaca gaaagaatatgtgacccaatgacgaccataaactttcttgttcctgtgtc aaattatctccggtttattgatgaagaaccagacactatgagctgcgtct cctccttaagattttgttttggtgtcttgttttttgtcaaggggtttcatt gtggccctgagcattagatccagggctttgtgcatgctaggccagggagc tatattcccgaactccagaagactaggaatttgagatataaatagaattt gaattaccttctgtacaattgattgtatggttctagaaatattgctatat taagggaagcctttgcagaagacagttattttgagatggtgcataacaca aaagaaatgaactaaagcctgaggcctgctctgtagctctgccttgccct tagcctacaataactttctttacctttcaagcatgtgccaccacgcctga ctttcaggcccttcattttaacaagaaagcaagtattcagttatcaactg actttccaaatgcatttgtatgaataaaaactacaaaaatataaaataa gaactatacacacaaaagccttgtatttaaaatttacgctgtggacatat tttgctcatcattcgtgagagcttgcggtaaaaaggcaaaggggaagagg aggatatctattttgggtaggctaatttggccttatccagacttcccttt tgggtggatgcagtctgcccagcacactattggcccatttcttctacatg gctttgtgctctgctctgcccttagctaattgtcccccttttgacatgcttt tgtcttccttaaagtttctatacttcaaaaaccatcccgctacactaat ggagtgattttctcaagggttgctttatgtttggggtttgtactgcaaga gttagtttctgatatagcaatggtgatagtatagtcttctaccatgaact ctatgccagcaagtacaggggtatatttcacatgggtgtttctgttcac tgagtttcatgtcttcttttgtatcttttgtttttgttttgtgagacaggg tttctctgtagcttttgagtcagtcctggaacttgctggccggccttgaa ctcacagagattcacctgcctctgcctcccaagtgctgggatttaaggtg tgagtcaccactgccaggttttttcttttgtatcttgagtgaactaaatag gtaagctttaaataataatatgagcagtctatttatatacattaaatatt aaatgcattgtgagatgagcatagcctttgaggcccaggaacagaaagat ttacttcacattgtaaatatactggtatacatacaaacgtacatacnnnn nngtgtgtgtgtgtgtgtgtgtgtgtgtgtgcatgccatagcacacatgt gaagtccagagtacagcattctcttttctaccttctgtagattcttgt ggtcagagtcaggtcaaatcaaatcagacagatgcatgtataaaatgctc ttacccactgaaccatcttgctgcttggtccacaagcttagtggaagaat gctgggaagtgaatagtatgtttttaaatgtagttaaccttgacttttg ttgttgttgctgttattgaggccacattttcattgttctgagaaaatatt actattttcctcagacagaattatatatttatttgaagttcatgaattcc atattattttcctgtatttattacaaatagcatgcttaaacacttccaag tagtgaaacagctgctcatgtaggacacggattattgacagtgctgccat ttatcagccagtaatccacttggcaggtagcacgctcatcgttatccttt atgcacacaaagccttgtttgaatttatctttaatgagtgtcaatgaa atggaaagagataagagttaaaaatacaacccaaactattgtatttacat ttctcttttagaagaaacctaaagcagcattacttcttgcccatatttaa taaataacatcatttaccccttgttccctgcctccagactctcccatatac tcctctttcaatttattggcccctttaaatgacatatcattacatgtat atccctacacataagtataaccagttcagtttgtataatgttacttgcat gtgtgttttcaatgctgatcatttggtagtggataaccaatggtgtgccc tatgaaggggcagagtatttgtatcatgcttagcattcctttgttgactg taggattttgttttaaggttgaggtctcttggtctttcccctgtctgcttc tgcatgtccatggccatccttgttcagctcatgtttatgtagtcatgctg atgaggctttatggatgtagcttctgacattgctaagcaacacagtctca gcaaactccccagtcctctggttcttacaatcttttccacactgtttcacc atgttgtctgagccttaggtgctgaagttgttttgtgtctgtatccattg ggactaggctccacatgtctgcatttgattacttgtggttttctgtaac ggtctctatgtgttgcaacgagaaggagtagttgctttgacgatgtgtaa agactatcttgtgggtataaggacaaatatttgcatgaagctatggatta
tgctggtctcaagcatgaactggataaattgtacagctcacacaaaacag
ctatagctagctgcacagtcaggcatgcactgatctgcttggggagttgt
taaccaaagggcttacatagctatgtattttctaagctctagttttacta
tcacaaagaaaattaattcacccttaattgtttaataagatgatatatct
tagggaaaaaatgaaggtctttttttgacttatataaaagcttatgtttt
ctacagttt exon2 (SEQ ID NO 32):
tgtcaaaagaacatgcctcgcaagtcctggtgaggaagcgccgcgcaaat
accttgcttgaagaaactaaaaagggcaatcttgaaagagaatgcatcga
agagctctgcaataaagaggaagccagggaggtctttgaaaacaatcccg
aaacg intron2 (SEQ ID NO 33):
gtaagagttcgtggaaatgaccaagtccacactcggatatatattggcag
tcagaacactgccagcttgagctaccttgcttctgtttgaaagctaatga
cttaggagttcatttctcatgtgttaccactgacatttcaggcaggctgc
caatgacaggcactccagccaaactccatttcccttaagtctcattactc
gcaactagtatcgactttataatgtgtgactattttattatcctaaccaa
atctggtagccttgagggtgcaagagaagatgcgactgaagggtaagtga
ccatatatgtacttgcattgtcactgtgcttttgttttggttgattgtgt
ttgagacagtctcttactctgtagctccaactacaaggagctccctatcc
atctgctttggcttcagcctcccaagtactgtgattatagactggtgtgt
cttgccatttatctttaagaggctctagatagaaatggggccacctaact
gagattagtcattacagcattatgtatgctgactgtatactattctgtaa
ccttcatgaagtttcccgaggccactgataatcagcagtaatcattagtg
tctaaaaatttccaagttacccacccgccaaacataacataaagacagca
acatgggactctttgtccattctgtgtttcaggagagggcaatttatagt
atgcttgtaactaacaggagtagcattaatatctccaaggagcactttga
gcatgaccttgagagtctacatggaacactgttcagggtctcctcagatg
ttctacctgagctgaattatacaatctggaggaaaagaaagagatgacat
acacaaggctcctcctttgcctctgccacagctcccagaaccatgacaac
agctgagtgataaagagcaaggactctttgtccatacttagaaaatttgt
ccccaactgtagctacttgtggtctgtggttgttattgtagctcttttt
aatcccatgtgttctgataggttcaaagaagaaattttccccaaatatg
caacaattaaattttaatctacctagaattgagacaaaaatgtgacgaaa
taccttgatcaaaaaacaactcaggaggaaagggtttttttttttttttt
ttggtttactaacctgaattgagggaagcaaaagtaggagctcaaaccag
gtgggaacctggaggcaggagctgatgcagaggcatggaggagtgctgct
tactggtctgctcctcatggcttctcagcttgttttcttatagaaccag
ggccaccgtcacaaaagtaccatcacctgcaatgggttgggcccttcccc
agggatctctgattaagaaaatttccctacaggtctgtctacaattcttt ttgtttgtttgtttgtttgtttgtttgtttcgagacagggtttgt
ctgtatagctttggagcctgtcctggaactcactctgtagaccaggttgg
cctcgaagtcacaaagatccacctgcctttgcctccctagtgctggatt
aaaggcttgtgtcaccactgccaggcctattttaaggaagcattttttctc
cttgagattccttcctctcaaatgattctagcttgtatcaagttgacata
aaattagccagcacagacaacaacaatagaaaattttctatcctacacaa
tgtaataaatttattgggtaggatttaacatatgtattctatgttttaca
ttctcattctaaaaaggaatgtgtatgcactcttacaaacttccataata
caaaagaatacagtatgtattagatatgtgcatatattccttcccttat
ggaaagtttaaaaagtagaaagaatggtataataaactgcaacacaacac
gtccctctaataagatcaaggctttcatttgattttgcctatccaccaca
tctaatcaatggttttgctttgagcaatcaagtcacatgattatattacc
catacttgagttgtatatctgcattgtagatatgttctcaaagctcagcc
tttaaagagtagtagggagggaagatggaccacaggaagaagggggagga
aggtgaagaaggaaaaacacattcgtgtttctttaccttcactaatagttt
tgttgacagattccacctactccctgtccatatccctcatactcttaggc
cagtattcccagtgttattgaccctgatgtttacctgttcgcttgtcatc
agcatgtcaccaatctttaaatgccattgtttgtctccttattgtcttgt
ctctgcttctgcagtaaacacactgttgtctgaatgagtcagtgtcaggc
ccctttcttataagccagtagaaacgtgcaagtttgtacatgataagagg
aaagagtgtagattttgatgtagaaaaagccaagctccactctaagccag
aattttgaatactttttatgcagaaattttgttttgtatgaaatattct
tgtgttatttatttacattatgagtgtactgtcagaagctcataaaaatt
accctgttcataaaatacattccttcatccatatgtcatcattattttgc
tatccatcaatatataaggaaggtgtttcacatgcattagatgcaataag
gtaagtggtcattttagttctcttaaatgatttcattgttgactccagt
gtagatagtcatcatggcataagatgtatcaaatgaagactaggtgtggt
ggtgcataccttcagtcccagcacacagaggcagaggaacatggattgct
gtgagtttcaggtggacctggtctacatagtgagttccaaggtagataga
gggtgtctcgagagaccctgtaagaaaagtctatgtttaattgccatgaa
aaaattagaggattataaagagggaatatattgttatagttatcaacta
caaccagttcaaatcagaagctttaaaatgttattttattgttcagtagt
gttttaagcatatatatgtatacacacaaacatatgtgtttatatata
tgtatatgtatactggtcaagtattggctatctattcttgaagtatttat
agaaaaattagaaatgtgaaaacatacaacatgtaggtcatttccatatt
catataaaagcaaattagaaaaattaatctttaactctgtagtgatattt
gagtttgctaatatctatttttttattttctttctag exon3 (SEQ ID NO 34):
gattattttatccaaaatatttgg

Example 4

Transcription Factor Engineering

Expression of Protein S may be reduced or abolished by transcriptional down regulation of Protein S mRNA. Transcription factors can be designed to bind specific DNA elements in the promoter region of the CHO Protein S gene. Zinc finger proteins are ideal for such a manipulation and common procedures are reviewed by Wolfe-S A et al. Annu. Rev. Biophys. Struct. vol 3:183-212, 1999 and Jamieson-A C et al. Nature Reviews, vol 2:361-368, 2003. Typically a single zinc finger binds three bases adjacent to each other on the same DNA strand and a forth base on the complementary strand. Thus, several zinc fingers can be combined in order to bind a desired DNA element. Recognition of a DNA element of 15-18 base pairs, which actually can be universal in the genome, needs a combination of 5-6 zinc fingers.

A DNA element having the sequence GGAGAG-GAGGGGGGG (SEQ ID NO 35) from the CHO Protein S promoter are chosen and Zinc finger proteins binding the DNA element is predicted based on the publications by Liu-P Q et al., Journal of Biological Chemistry, Vol. 276 (14), pp. 11323-11334, 2001 and Zhang-L et al. Journal of Biological Chemistry, Vol. 275 (43), pp. 33850-33860, 2000. A synthetic five zinc finger protein based on SP1 and BTEB4 is made by PCR from overlapping oligonucleotides as described in Zhang-L et al. Journal of Biological Chemistry, Vol. 275 (43), pp. 33850-33860, 2000: Zinc finger 5 CXXCXXXXXQS-GHLQRHXXXH (SEQ ID NO 36) interacts with GGAg; zinc finger 4 CXXXXCXXXXXRSDNLARHXXXH (SEQ ID NO 37) interacts with GAGg; zinc finger 3 CXX-CXXXXXRSDNLTRHXXXH (SEQ ID NO 38) interacts with GAGg; zinc finger 2 CXXXXCXXXXXRSDHL-TRHXXXH (SEQ ID NO 39) interacts with GGGg; zinc finger 1 CXXXXCXXXXXRSDHLARHXXXH (SEQ ID NO 40) interacts with GGGa; and N-terminal to the zinc fingers the KRAB domain of KOX1 is inserted.

Upon binding of the engineered zinc finger protein to the GGAGAGGAGGGGGGG (SEQ ID NO 41) DNA element the CHO Protein S transcription was expected to be down regulated.

The CHO Protein S promoter region (SEQ ID NO 29) was cloned into pGL3-basic (Promega, Madison) and was used as reporter construct in a luciferase reporter assay to determine the effect of ZNF-PS. The plasmid encoding the ZNF-PS gene and the CHO Protein S reporter plasmid were transfected into CHO-K1 cells and luciferase activity was determined. ZNF-PS can downregulate Protein S transcription 50% in a dose-response independent manner. FIG. 3a illustrates ZNF-PS downregulation of Protein S. In a similar experiment the CHO-K1 cells were transfected with ZNF-PS and pEGFP (Enhanced Green Fluorescent Protein) and Protein S and pEGFP mRNA were determined by real-time PCR. pEGFP served as transfection control. FIG. 3b shows a downregulation of Protein S by 50%.

```
ZNF-PS
                                          (SEQ ID NO 42)
Mdaksltawsrtlvtfkdvfvdftreewklldtaqqivyrnvmlenyknl vslgyqltkpdvilrlekgeepwlvereihqethpdsetafeikssvssr sifkdkqscdikmegmarndlwylsleevwkpgkkkqhichiqgcgkvyg rsdhlarhlrwhtgerpfmctwsycgkrftrsdhltrhkrthtgekkfac pecpkrfmrsdnltrhikthtgerpfacdwqgcdkkfarsdnlarhhrth tgekrfscplcskrftqsghlqrharrhpgfhpdllrrpgarstspsdsl pcslagspapspapspapagl
```

Example 5

Determination of Numbers of Protein S Alleles in the CHO K1 Genome

The CHO-K1 cell line has only 21 chromosomes, compared to the Chinese Hamster which has 22 chromosomes, and only 8 of these 21 are normal. In the 13 altered chromosomes translocations, deletions, and pericentric inversions have been detected (Deaven & Petersen, Chromosoma 1973; 41(2), 129-144). It is not known whether the Protein S gene is present on normal or altered chromosomes or how many alleles are present in the CHO-K1 genome.

Figure 4:
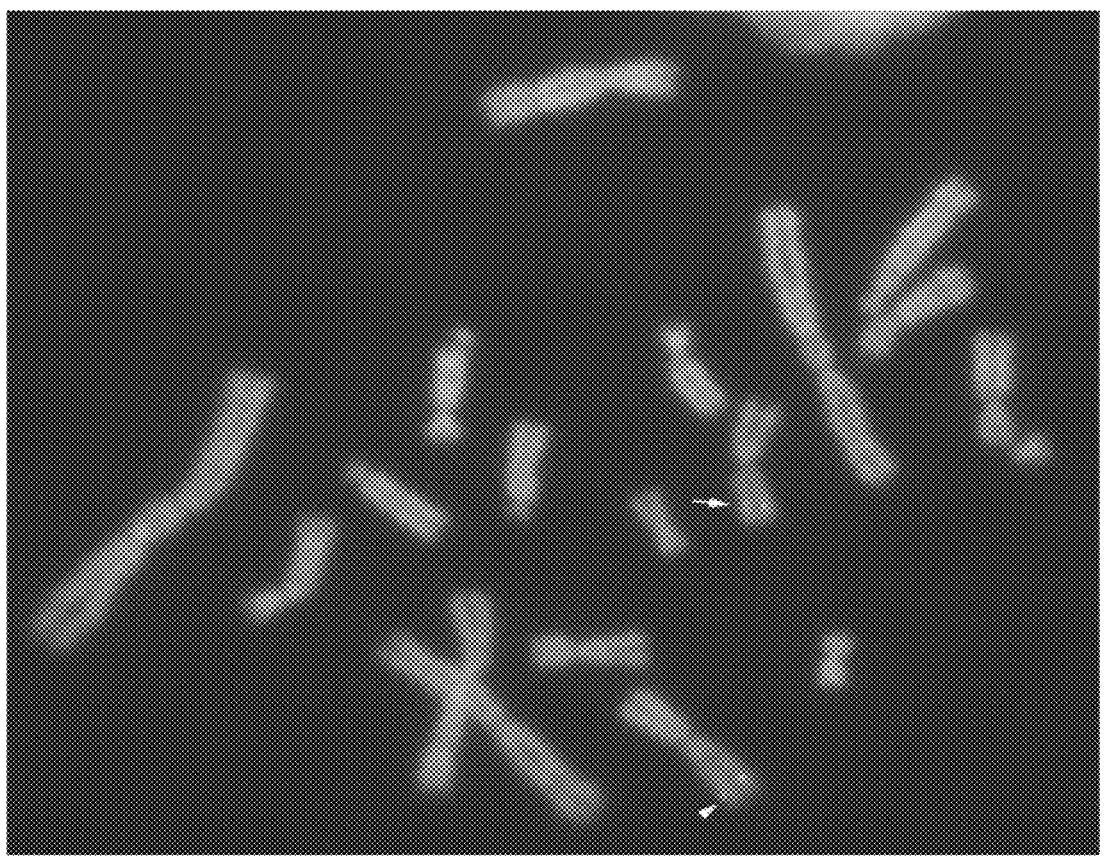
FIG. 4: The Protein S gene is localized onto two different chromosomes in the same metaphase of CHO-K1 cells. The figure illustrates Protein S gene localization in the CHO-K1 genome. FISH was per-formed on CHO-K1 chromosomes using Protein intron 1 as probe.

The SeeDNA Biotech Inc. company performed a FISH (Fluorescence In Situ Hybridization) analysis on the genome of CHO K1 cells (ATCC# CCL-61) using a plasmid containing the Protein S Intron 1 probe (SEQ ID NO 43) in pCR2.1 (Invitrogen, Carlsbad) cloned and supplied by us. The results of the FISH analysis is shown i FIG. 4. The Protein S gene is localized onto two different chromosomes in the same metaphase. The chromosome with locus A (shown by an arrow) is submetacentric and of smaller size. The chromosome with locus B (shown by an arrowhead) is metacentric and of bigger size. The banding pattern of these two chromosomes is also different.

```
The Protein S Intron 1 probe
                                          (SEQ ID NO 43)
ctgctggtatgcctagccctggtgctgccagcctcggagacaaactgtaa gtaatccatacctcctggcttctccattccctatgtgccccggcttgaag attttccactaggctgtttgctgcctcctaagtttccagtaagtccgcca ccattcagagagtcgcggcagcctgggtctggtgggcagtgtaaaggtgg gacaggatcaaagcttgccttgctttgagaaccattgtccacaggacttg attccagaacccgggtgacactaagtgtcaaaggaattgcttgaacatag tcctaaatattgctaggaaagctaagtcaagcctgttgccctcctcccgt ttacaagagtgccccagcccgcaccctctcctgcggctaaccttccttt gcaatttctggactttgaacttgattgactggtctcacattgacaaactg tttggggactgctggggtgttacatatgattctctaaccttgatataaga aatagctgttggatgttaccttgtaccgaggatcattttctgagggtttt gactgttgccgctttgagatggcagcaagaattctgtacaacacacacat ttttgtgtttcttggtctttcctcttcccattctcagattccgggcagta tatcgagttttctcttagaaatataaaacgaaccacaaggttttagtaca ttttaatggtcaattaaattgtttttagaagcttaaatatgttcataatt aacactgctttcttttgctcttttgtagtcccagtcactggcatgggagc aataactgtataacaaataccacttaggtcactgcgagcaccaaagaaac ttttcaaagatggtaattaagtaggagtttgctggaattgcaagttttta ttaattagtaaggaatctagcctgatatttttaaatgtctaactaagtta
```

-continued
aagaccagaatgaaactggttcacttttattgaggataacaagttacag
ttataaagcctcaacaatcaaagccctacgatgaagcagcgtgtgactgt
atgcacatgatctatcttgttcagaggaacaatcaaacattttcagatag
catcagggcggtggtggtactcgcctataatcctagcaaagtcagaggca
agcagatctctgtgttcaaggccagcctagtctacagagtgagttccagg
acaactggggctacacagagaaacctgtctcagagaaaaacaaaataaaa
ccaaattcagatagctggtgtttgggaaaagagcaaaagacagcagtgct
ggccacacagagagtagacaagttcattctacaaggacatcacagaaaga
atatgtgacccaatgacgaccataaactttcttgttcctgtgtcaaatta
tctccggtttattgatgaagaaccagacactatgagctgcgtctcctcct
taagatttgttttggtgtcttgttttgtcaaggggtttcattgtggcc
ctgagcattagatccagggctttgtgcatgctaggccagggagctatatt
cccgaactccagaagactaggaatttgagatataaatagaatttgaatta
ccttctgtacaattgattgtatggttctagaaatattgctatattaaggg
aagcctttgcagaagacagttattttgagatggtgcataacacaaaagaa
atgaactaaagcctgaggcctgctctgtagctctgccttgccttagcct
acaataactttcttacctttcaagcatgtgccaccacgcctgactttca
ggcccttcattttaacaagaaagcaagtattcagttatcaactgactttc
caaatgcatttgtatgaataaaaactacaaaaatataaaaataagaacta
tacacacaaaagccttgtatttaaaatttacgctgtggacatattttgct
catcattcgtgagagcttgcggtaaaaaggcaaaggggaagaggaggata
tctattttgggtaggctaatttggccttatccagacttccttttgggtg
gatgcagtctgcccagcacactattggcccatttcttctacatggctttg
tgctctgctctgcccttagctaattgtcccctttgacatgcttttgtctt
tccttaaagtttctatacttcaaaaaccatcccgctacactaatggagtg
attttctcaagggttgctttatgtttggggtttgtactgcaagagttagt
ttctgatatagcaatggtgatagtatagtcttctaccatgaactctatgc
cagcaagtacaggggtatatttcacatgggtgttttctgttcactgagtt
tcatgtcttctttgtatcttttgttttgttttgtgagacagggtttctc
tgtagcttttgagtcagtcctggaacttgctggccggccttgaactcaca
gagattcacctgcctctgcctcccaagtgctgggatttaaggtgtgagtc
accactgccaggttttttctttgtatcttgagtgaactaaataggtaagc
tttaaataataatgagcagtctatttatatacattaaatattaaatgc
attgtgagatgagcatagcctttgaggcccaggaacagaaagatttactt
cacattgtaaatatactggtatacatacaaacgtacatacnnnnnngtgt
gtgtgtgtgtgtgtgtgtgtgtgcatgccatagcacacatgtgaagtc
cagagtacagcattctctttttctaccttctgtagattcttgtggtcag
agtcaggtcaaatcaaatcagacagatgcatgtataaaatgctcttaccc
actgaaccatcttgctgcttggtccacaagcttagtggaagaatgctggg
aagtgaatagtatgtttttaaatgtagttaaccttgacttttttgttgttg
ttgctgttattgaggccacattttcattgttctgagaaaatattactatt -continued
ttcctcagacagaattatatatttatttgaagttcatgaattccatatta
ttttcctgtatttattacaaatagcatgcttaaacacttccaagtagtga
aacagctgctcatgtaggacacggattattgacagtgctgccatttatca
gccagtaatccacttggcaggtagcacgctcatcgttatcctttatgcac
acaaagccttgtttgaattttatcttttaatgagtgtcaatgaaatggaa
agagataagagttaaaaatacaacccaaactattgtatttacatttctct
tttagaagaaacctaaagcagcattacttcttgcccatatttaataaata
acatcatttacccttgttccctgcctccagactctcccatatactcctct
ttcaattttattggcccctttaaatgacatatcattacatgtatatccct
acacataagtataaccagttcagtttgtataatgttacttgcatgtgtgt
tttcaatgctgatcatttggtagtggataaccaatggtgtgccctatgaa
ggggcagagtatttgtatcatgcttagcattcctttgttgactgtaggat
tttgtttaaggttgaggtctcttggtctttccctgtctgcttctgcatg
tccatggccatccttgttcagctcatgtttatgtagtcatgctgatgagg
ctttatggatgtagcttctgacattgctaagcaacacagtctcagcaaac
tccccagtcctctggttcttacaatctttccacactgtttcaccatgttg
tctgagccttaggtgctgaagttgttttgtgtctgtatccattgggacta
ggctccacatgtctgcatttgattacttgtggttttctgtaacggtctc
tatgtgttgcaacgagaaggagtagttgctttgacgatgtgtaaagacta
tcttgtgggtataaggacaaatatttgcatgaagctatggattatgctgg
tctcaagcatgaactggataaattgtacagctcacacaaaacagctatag
ctagctgcacagtcaggcatgcactgatctgcttggggagttgttaacca
aagggcttacatagctatgtattttctaagctctagttttactatcacaa
agaaaattaattcacccttaattgtttaataagatgatatatcttaggga
aaaaatgaaggtcttttttgacttatataaaagcttatgttttctacag
ttttgtcaaaagaacatgcctcgcaagtcctggtgaggaagcgccgcgca
aataccttgcttgaagaaactaaaaagggcaatcttgaaagagaatgcat
cgaagagctctgc Example 6

Gene Targeting of CHO Protein S Enhanced by Zinc Finger-Nuclease Fusion Proteins Gene targeting by homologous recombination is hard and laborious work because the somatic recombinations that takes place in mammalian cells not very often are homologous. However, site-specific cleavage of the DNA strands can enhance homologous recombination. Engineering of DNA binding zinc fingers fused to endonucleases makes it possible to design almost exactly where the DNA cleavage should occur (Durai et al., Nucleic Acids Research, 2005; 33(18), 5970-5990 and Smith et al., Nucleic Acids Research, 2000; 28(17), 3361-3369). Two zinc finger proteins, designed to bind 5'-GTCCTGAGC-3' (right finger) and 5'-GCTGG-TATG-3' (left finger) elements, were made in the framework published by Mani et al. (Mani et al., Biochemical and Biophysical Research Communications 2005, 335; 447-457).

Zinc finger DNA binding specificity of zinc finger has previously been described by (Rebar-E J, et al. Nature Medicine 8 (2002) 1427-1432; Liu-P Q, et al. Journal of Biological Chemistry 276 (2001) 11323-11334; Ren-D, et al. Genes & Development 16 (2002) 27-32; Mani-M, et al Biochemical and Biophysical Research Communications 335 (2005) 447-457).

Figure 5:
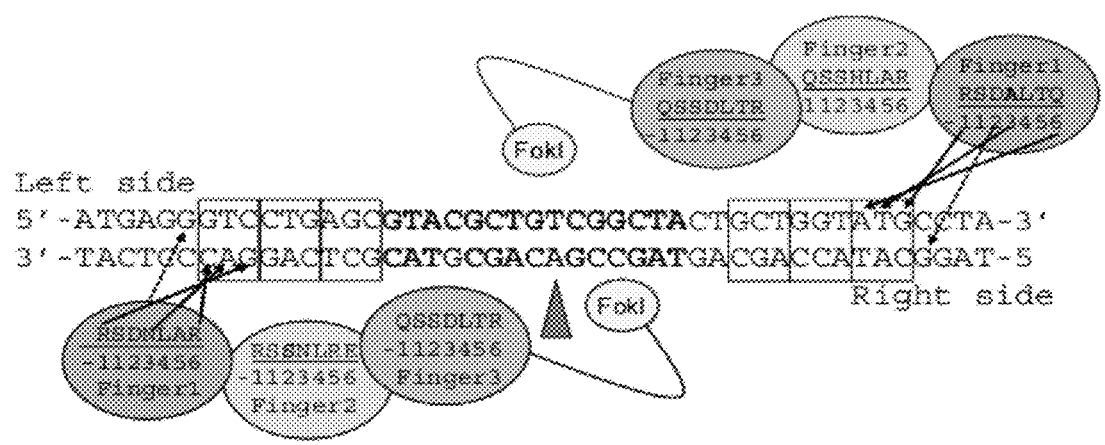
FIG. 5: Two zinc finger proteins fused to nucleases bind inside exon1 of the CHO Protein S gene (SEQ ID NO: 30). The figure illustrates DNA binding specificity of two zinc finger proteins fused to Fok I nuclease.
The left zinc finger protein is expected to bind to 5'-GTCCT-GAGC-3' (upper strand) and the right zinc finger will bind to 5'-GCTGGTATG-3' (upper strand) both sequence element is harbored by Protein S exon 1. The two zinc finger are either fused to Fok I og Sts I nucleases, the nucleases will homodimerize and perform the cleavage of the DNA strands.
Figure 6:
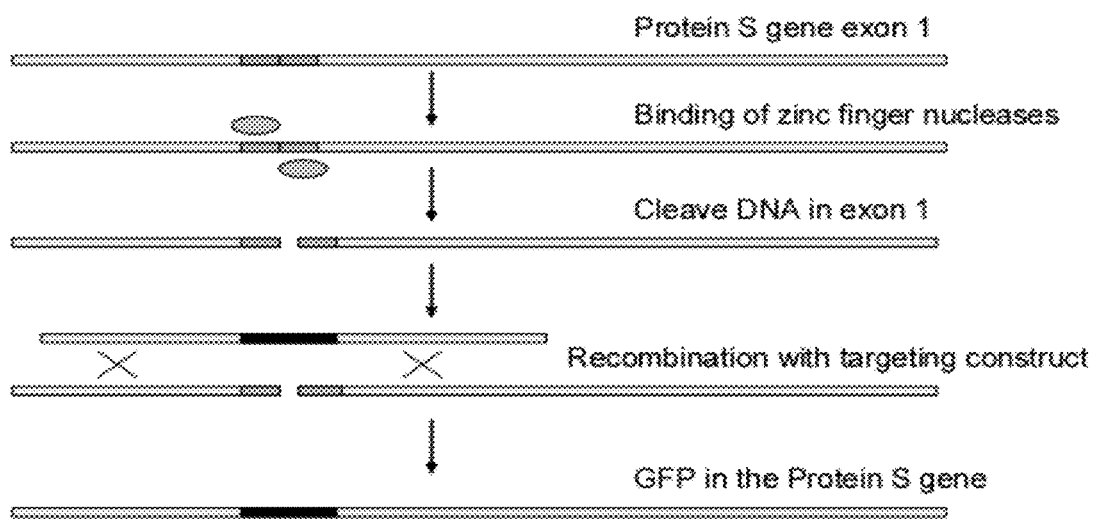
FIG. 6: Gene targeting by homologous recombination enhanced by zinc finger nuclease cleavage. The figure illustrates the step in homologous recombination enhanced by zinc finger nucleases.
The zinc finger nucleases will bind their specific binding sites within Protein S exon 1 and cleave the DNA strands. The gene targeting vector transfected along with the nucleases contains a large fragment identical to the Protein S gene, on each side of the EGFP gene. Recombination occurs between the Protein S gene and targeting vector. Recombinant cells can be sorted due to EGFP expression.

The right and left zinc finger were both either fused to the nuclease domain of Fok I and Sts I restriction enzyme (SEQ ID NO 44-51). Fok I and Sts I restriction enzyme needs to homodimerize to be able to cleave DNA, which also increase the specificity of the zinc finger pair. The function of the engineered nucleases are illustrated in FIGS. 5 and 6. When the genomic DNA has been cleaved by the zinc finger nucleases the repair mechanism will seek to repair the gap, very likely by homologous recombination. The gene targeting construct (SEQ ID NO 52) devoid of the Protein S gene will be transfected along with the nucleases. In the place of Protein S exon 1 in the genome the EGFP gene will be inserted. FIG. 6 illustrates the flow scheme of the homologous recombination. The gene targeting construct was made by exchanging the luciferase gene in the Protein S reporter construct (example 4) by the EGFP-gene and further inserting Protein S intron 1 after the poly A signal. The construct consists of Protein S promoter, EGFP-gene, PolyA-signal and Protein S intron1, no exon1. The homozygous recombinant CHO cell line will express EGFP and not Protein S because the Protein S signal peptide has been deleted and the transcript will be truncated right after the EGFP coding sequence due to the PolyA signal. Heterozygous cell clones are expected to be most abundant and a PCR analysis will reveal whether we have succeeded to make a homozygous cell clone. A heterozygous cell clone can be treated a second time with a targeting vector containing an antibiotical resistance gene in place of the EGFP gene to facilitate selection.

```
Left zinc finger-Fok I DNA sequence
                                        (SEQ ID NO 44)
atgaagctactgtcttctatcgaacaagcatgcccaaaaaagaagagaaa ggtagatgaaaaaccttacaagtgtccggaatgtgggaagtcctttagtc ggagcgacaacctggcccggcaccagcggacgcataccggtgagaagccc tacaaatgcccagaatgcggaaaatcattttcgcggagcagcaacctgcg ggagcaccaacgaacccacacaggcgagaaaccatttaaatgtcctgagt gtggtaagagctttagccggagcgacaacctgacccggcatcaagctact catacgggcggcggtggcagcggtggcggtagcggcggtggcagcggtgg cggatcccaactagtcaaaagtgaactggaggagaagaaatctgaacttc gtcataaattgaaatatgtgcctcatgaatatattgaattaattgaaatt gccagaaattccactcaggatagaattcttgaaatgaaggtaatggaatt ttttatgaaagtttatggatatagaggtaaacatttgggtggatcaagga accggacggagcaatttatactgtcggatctcctattgattacggtgtga tcgtggatactaaagcttatagcggaggttataatctgccaattggccaa gcagatgaaatgcaacgatatgtcgaagaaaatcaaacacgaaacaaaca tatcaaccctaatgaatggtggaaagtctatccatcttctgtaacggaat ttaagtttttatttgtgagtggtcactttaaaggaaactacaaagctcag cttacacgattaaatcatatcactaattgtaatggagctgttcttagtgt
```

```
agaagagcttttaattggtggagaaatgattaaagccggcacattaacct tagaggaagtgagacggaaatttaataacggcgagataaactttag Left zinc finger-Sts I DNA sequence
                                        (SEQ ID NO 45)
atgaagctactgtcttctatcgaacaagcatgcccaaaaaagaagagaaa ggtagatgaaaaaccttacaagtgtccggaatgtgggaagtcctttagtc ggagcgacaacctggcccggcaccagcggacgcataccggtgagaagccc tacaaatgcccagaatgcggaaaatcattttcgcggagcagcaacctgcg ggagcaccaacgaacccacacaggcgagaaaccatttaaatgtcctgagt gtggtaagagctttagccggagcgacaacctgacccggcatcaagctact catacgggcggcggtggcagcggtggcggtagcggcggtggcagcggtgg cggatccgtattagaaaaaagtgatattgaaaaatttaagaatcaattgc gtacggaactaaccaatattgaccattcttatcttaaaggaattgatata gctagtaaaaagaaaaccagtaatgttgaaaatacggaatttgaagcaat atcaaccaagattttttacggatgagttgggtttttcaggcaaacatctag gaggaagcaacaaaccagatggactcctgtgggatgatgattgtgcaatt attcttgattcaaaagcttactcagaaggctttccactcactgcctccca cacagatgctatgggaagatatttgaggcaatttacagagcgaaaagaag aaataaagccaacgtggtgggatattgctccagaacatttagacaataca tatttcgcttacgtttctgggagttttcgggtaattataaggaacagtt acaaaaatttaggcaagatacaaaccatttaggtggggcactagagtttg ttaaattgttattactagcaaataattataaaactcaaaaaatgagtaaa aaagaagttaagaaaagtattcttgattataatatttcatatgaagaata tgctccattacttgcagaaatagagtaa Right zinc finger-Fok I DNA sequence
                                        (SEQ ID NO 46)
atgaagctactgtcttctatcgaacaagcatgcccaaaaaagaagagaaa ggtagatgaaaaaccttacaagtgtccggaatgtgggaagtcctttagtc ggagcgacgccctgacccagcaccagcggacgcataccggtgagaagccc tacaaatgcccagaatgcggaaaatcattttcgcagagcagccacctggc ccggcaccaacgaacccacacaggcgagaaaccatttaaatgtcctgagt gtggtaagagctttagccagagcagccacctgacccggcatcaagctact catacgggcggcggtggcagcggtggcggtagcggcggtggcagcggtgg cggatcccaactagtcaaaagtgaactggaggagaagaaatctgaacttc gtcataaattgaaatatgtgcctcatgaatatattgaattaattgaaatt gccagaaattccactcaggatagaattcttgaaatgaaggtaatggaatt ttttatgaaagtttatggatatagaggtaaacatttgggtggatcaagga aaccggacggagcaatttatactgtcggatctcctattgattacggtgtg atcgtggatactaaagcttatagcggaggttataatctgccaattggcca agcagatgaaatgcaacgatatgtcgaagaaaatcaaacacgaaacaaac atatcaaccctaatgaatggtggaaagtctatccatcttctgtaacggaa tttaagttttttatttgtgagtggtcactttaaaggaaactacaaagctca gcttacacgattaaatcatatcactaattgtaatggagctgttcttagtg
```

Right zinc finger-Sts I DNA sequence (SEQ ID NO 47)

atgaagctactgtcttctatcgaacaagcatgcccaaaaaagaagagaaa ggtagatgaaaaaccttacaagtgtccggaatgtgggaagtcctttagtc ggagcgacgccctgacccagcaccagcggacgcataccggtgagaagccc tacaaatgcccagaatgcggaaaatcattttcgcagagcagccacctggc ccggcaccaacgaacccacacaggcgagaaaccatttaaatgtcctgagt gtggtaagagctttagccagagcagccacctgacccggcatcaagctact catacgggcggcggtggcagcggtggcggtagcggcggtggcagcggtgg cggatccgtattagaaaaaagtgatattgaaaaatttaagaatcaattgc gtacggaactaaccaatattgaccattcttatcttaaaggaattgatata gctagtaaaaagaaaaccagtaatgttgaaaatacggaatttgaagcaat atcaaccaagattttttacggatgagttgggtttttcaggcaaacatctag gaggaagcaacaaaccagatggactcctgtgggatgatgattgtgcaatt attcttgattcaaaagcttactcagaaggctttccactcactgcctccca cacagatgctatgggaagatatttgaggcaatttacagagcgaaaagaag aaataaagccaacgtggtgggatattgctccagaacatttagacaataca tatttcgcttacgtttctgggagttttcggggtaattataaggaacagtt acaaaaatttaggcaagatacaaaccatttaggtggggcactagagtttg ttaaattgttattactagcaaataattataaaactcaaaaatgagtaaa aaagaagttaagaaaagtattcttgattataatatttcatatgaagaata tgctccattacttgcagaaatagagtaa Left zinc finger-Fok I protein sequence (SEQ ID NO 48)

mkllssieqacpkkkrkvdekpykcpecgksfsrsdnlarhqrthtgekp ykcpecgksfsrssnlrehqrthtgekpfkcpecgksfsrsdnltrhqat htggggsgggsgggsgggsqlvkseleekkselrhklkyvpheyieliei arnstqdrilemkvmeffmkvygyrgkhlggsrkpdgaiytvgspidygv ivdtkaysggynlpigqademqryveenqtrnkhinpnewwkvypssvte fkflfvsghfkgnykaqltrinhitncngavlsveelliggemikagtlt leevrrkfnngeinf Left zinc finger-Sts I protein sequence (SEQ ID NO 49)

mkllssieqacpkkkrkvdekpykcpecgksfsrsdnlarhqrthtgekp ykcpecgksfsrssnlrehqrthtgekpfkcpecgksfsrsdnltrhqat htggggsgggsgggsgggsvleksdiekfknqlrteltnidhsylkgidi askkktsnventefeaistkiftdelgfsgkhlggsnkpdgllwdddcai ildskaysegfpltashtdamgrylrqfterkeeikptwwdiapehldnt yfayvsgsfsgnykeqlqkfrqdtnhlggalefvklllllannyktqkmsk kevkksildynisyeeyapllaeie Right zinc finger-Fok I protein sequence (SEQ ID NO 50)

mkllssieqacpkkkrkvdekpykcpecgksfsrsdaltqhqrthtgekp ykcpecgksfsqsshlarhqrthtgekpfkcpecgksfsqsshltrhqat htggggsgggsgggsgggsqlvkseleekkselrhklkyvpheyieliei arnstqdrilemkvmeffmkvygyrgkhlggsrkpdgaiytvgspidygv ivdtkaysggynlpigqademqryveenqtrnkhinpnewwkvypssvte fkflfvsghfkgnykaqltrinhitncngavlsveelliggemikagtlt leevrrkfnngeinf Right zinc finger-Sts I protein sequence (SEQ ID NO 51)

mkllssieqacpkkkrkvdekpykcpecgksfsrsdaltqhqrthtgekp ykcpecgksfsqsshlarhqrthtgekpfkcpecgksfsqsshltrhqat htggggsgggsgggsgggsvleksdiekfknqlrteltnidhsylkgidi askkktsnventefeaistkiftdelgfsgkhlggsnkpdgllwdddcai ildskaysegfpltashtdamgrylrqfterkeeikptwwdiapehldnt yfayvsgsfsgnykeqlqkfrqdtnhlggalefvklllllannyktqkmsk kevkksildynisyeeyapllaeie Protein S promoter-EGFP-Protein S intron 1 targeting construct (SEQ ID NO 52)

ggtaccgagctcttacgcgtgctagcccgggctcgagatctcaacccctt ttgaccatacacatttctactctttgtgtttgctggagctgttttctccc cacactcaacccccctttgctgaagcctggaacttgctttccacagcttaa gttgttataggtttcaatcatctgtccacctccctgactttcataatttt gtgaaataccctttgcatatatatgggactaaatattattttctcctgg ttgtccataatagattaatttaattcctaaacaaagaacagaacatagat tggtatagtagaagagtttccctttctccctactgcatgaatggaaattcc ccaaaccatccttatcagagaaattaactcacatactagtcacctttcat tcagctggatgacaaaatcattttaaaaaagagaataaagaaaacagat aagaacaactagatctaggaataatacttaaaatatgattctgcttagta ggtttcattcacacacctagaaaaaaaaatcagtcaatgtttcctttggg cagaaaatgagcaataatgggtatgcattgaccactactgttggacatag ccttattgcttcatatagcatctattcaaagtctcagatcaacactatga aaacctgtcatctctgtattagatgatgtgactggggctgtaaagggtaa gctcttttcttacagctatacaacaacgctaagaccaagttctgtgcttt gagcccaggcagtttagtttcccaggagcaacctaaagcctgattcacag gcatatgtatgatccaaactgaatggtagtacatcaataccaaaacaatc tattggtggaaacacaccataggtgatcgaaatactccattttcttttcc tctcatgacttctgttctgagcagtcctcttcctaaagtctacattgtct tctgagttcaggctgcatcttgacatcctcctggctggcacagtctctg gacaaggagggaagaaggagaagaggggaaagggagaggagggggggagg gagagaaagaatgggaagaggaaggatatgaaagagagaagagaggaggg aaggcgggaggaagggagggagggagggagggagggagagagggagagagga -continued gagagagagagagagagagagagagagagagagagagagagagagaga
gagagggagagggagagagagacagagagagagagagggagagggagaga
gagagagagagagagagagagagagagagagagagtgaggagagag
agagagagtttttcttcaccattggacattcctaaagaaaagaagtaaatg
caggattggggacagtgacagaggacctctgataaactttctgaggcctc
tgacctcactctctcggagccctcctccaccacccacccccccctccct
agctgagaaaagcttccaggaaatgtcccagtcatcgcttcccctcccgg
gctgggggctgggagcgggcggtcccctcaggccagggctgctccggccg
cgctcgggcagggccacaacagagctgggaaagctgagcccaggctcgca
gctcctctgggcggagcgccggctcggtcccgctgcgccagccgtgatc
cccggcagcctgctcagccatggtgagcaagggcgaggagctgttcaccg
gggtggtgcccatcctggtcgagctggacggcgacgtaaacggccacaag
ttcagcgtgtccggcgagggcgagggcgatgccacctacggcaagctgac
cctgaagttcatctgcaccaccggcaagctgcccgtgccctggcccaccc
tcgtgaccaccctgacctacggcgtgcagtgcttcagccgctaccccgac
cacatgaagcagcacgacttcttcaagtccgccatgcccgaaggctacgt
ccaggagcgcaccatcttcttcaaggacgacggcaactacaagacccgcg
ccgaggtgaagttcgagggcgacaccctggtgaaccgcatcgagctgaag
ggcatcgacttcaaggaggacggcaacatcctggggcacaagctggagta
caactacaacagccacaacgtctatatcatggccgacaagcagaagaacg
gcatcaaggtgaacttcaagatccgccacaacatcgaggacggcagcgtg
cagctcgccgaccactaccagcagaacacccccatcggcgacggccccgt
gctgctgcccgacaaccactacctgagcacccagtccgccctgagcaaag
accccaacgagaagcgcgatcacatggtcctgctggagttcgtgaccgcc
gccgggatcactctcggcatggacgagctgtacaagtaaagcggccgcga
ctctagagtcggggcggccggccgcttcgagcagacatgataagatacat
tgatgagtttggacaaaccacaactagaatgcagtgaaaaaaatgcttta
tttgtgaaatttgtgatgctattgctttatttgtaaccattataagctgc
aataaacaagttaacaacaacaattgcattcattttatgtttcaggttca
ggggggaggtgtgggaggttttttaaagcaagtaaaacctctacaaatgtg
gtaaaatcgataaggatcctgctggtatgcctagccctggtgctgccagc
ctcggagacaaactgtaagtaatccatacctcctggcttctccattccct
atgtgccccggcttgaagattttccactaggctgtttgctgcctcctaag
tttccagtaagtccgccaccattcagagagtcgcggcagcctgggtctgg
tgggcagtgtaaaggtgggacaggatcaaacttgccttgctttgagaacc
attgtccacaggacttgattccagaacccgggtgacactaagtgtcaaag
gaattgcttgaacatagtcctaaatattgctaggaaagctaagtcaagcc
tgttgccctcctcccgtttacaagagtgccccagcccgcaccctctcctg
cggctaaccttccttttgcaatttctggactttgaacttgattgactggt
ctcacattgacaaactgtttggggactgctgggtgttacatatgattct
ctaaccttgatataagaaatagctgttggatgttaccttgtaccgaggat -continued cattttctgagggttttgactgttgccgctttgagatggcagcaagaatt
ctgtacaacacacacattttgtgtttcttggtctttcctcttcccattc
tcagattccgggcagtatatcgagttttctcttagaaatataaaacgaac
cacaaggttttagtacattttaatggtcaattaaattgttttagaagct
taaatatgttcataattaacactgctttcttttgctcttttgtagtccca
gtcactggcatgggagcaataactgtataacaaataccacttaggtcact
gcgagcaccaaagaaacttttcaaagatggtaattaagtaggagtttgct
ggaattgcaagttttattaattagtaaggaatctagcctgatattttta
aatgtctaactaagttaaagaccagaatgaaactggttcacttttttattg
aggataaacaagttacagttataaagcctcaacaatcaaagccctacgat
gaagcagcgtgtgactgtatgcacatgatctatcttgttcagaggaacaa
tcaaacattttcagatagcatcagggcggtggtggtactcgcctataatc
ctagcaaagtcagaggcaagcagatctctgtgttcaaggccagcctagtc
tacagagtgagttccaggacaactgggggctacacagagaaacctgtctca
gagaaaaacaaaataaaaccaaattcagatagctggtgtttgggaaaaga
gcaaaagacagcagtgctggccacacagagagtagacaagttcattctac
aaggacatcacagaaagaatatgtgacccaatgacgaccataaactttct
tgttcctgtgtcaaattatctccggtttattgatgaagaaccagacacta
tgagctgcgtctcctccttaagattttgttttggtgtcttgttttttgtca
aggggtttcattgtgggccctgagcattagatccagggctttgtgcatgct
aggccagggagctatattcccgaactccagaagactaggaatttgagata
taaatagaatttgaattaccttctgtacaattgattgtatggttctagaa
atattgctatattaagggaagcctttgcagaagacagttattttgagatg
gtgcataacacaaaagaaatgaactaaagcctgaggcctgctctgtagct
ctgccttgcccttagcctacaataactttctttacctttcaagcatgtgc
caccacgcctgactttcaggcccttcattttaacaagaaagcaagtattc
agttatcaactgactttccaaatgcatttgtatgaataaaaactacaaaa
atataaaaataagaactatacacacaaaagccttgtatttaaaatttacg
ctgtggacatattttgctcatcattcgtgagagcttgcggtaaaaaggca
aaggggaagaggaggatatctatttgggtaggctaatttggccttatcc
agacttccctttgggtggatgcagtctgcccagcacactattggcccat
ttcttctacatggctttgtgctctgctctgcccttagctaattgtccct
ttgacatgcttttgtctttccttaaagtttctatacttcaaaaaccatcc
cgctacactaatggagtgattttctcaagggttgctttatgtttggggtt
tgtactgcaagagttagtttctgatatagcaatggtgatagtatagtctt
ctaccatgaactctatgccagcaagtacaggggtatatttcacatgggtg
ttttctgttcactgagtttcatgtcttctttgtatcttttttgttttgttt
tgtgagacagggtttctctgtagcttttgagtcagtcctggaacttgctg
gccggccttgaactcacagagattcacctgcctctgcctcccaagtgctg
ggatttaaggtgtgagtcaccactgccaggttttttctttgtatcttgag

```
tgaactaaataggtaagcttttaaataataatatgagcagtctatttatat
acattaaatattaaatgcattgtgagatgagcatagcctttgaggcccag
gaacagaaagatttacttcacattgtaaatatactggtatacatacaaac
gtacatacnnnnnngtgtgtgtgtgtgtgtgtgtgtgtgtgcatgcca
tagcacacatgtgaagtccagagtacagcattctcttttctacctttct
gtagattcttgtggtcagagtcaggtcaaatcaaatcagacagatgcatg
tataaaatgctcttacccactgaaccatcttgctgcttggtccacaagct
tagtggaagaatgctgggaagtgaatagtatgttttttaaatgtagttaac
cttgacttttttgttgttgttgctgttattgaggccacattttcattgttc
tgagaaaatattactatttttcctcagacagaattatatatttatttgaag
ttcatgaattccatattattttcctgtatttattacaaatagcatgctta
aacacttccaagtagtgaaacagctgctcatgtaggacacggattattga
cagtgctgccatttatcagccagtaatccacttggcaggtagcacgctca
tcgttatcctttatgcacacaaagccttgtttgaattttatcttttaatg
agtgtcaatgaaatggaaagagataagagttaaaaatacaacccaaacta
ttgtatttacatttctcttttagaagaaacctaaagcagcattacttctt
gcccatatttaataaataacatcatttaccctcgttccctgcctccagac
tctcccatatactcctctttcaattttattggccccttaaatgacatat
cattacatgtatatccctacacataagtataaccagttcagtttgtataa
tgttacttgcatgtgtgttttcaatgctgatcatttggtagtggataacc
aatggtgtgccctatgaaggggcagagtatttgtatcatgcttagcattc
ctttgtcgaccgatgcccttgagagccttcaacccagtcagctccttccg
gtgggcgcggggcatgactatcgtcgccgcacttatgactgtcttcttta
tcatgcaactcgtaggacaggtgccggcagcgctcttccgcttcctcgct
cactgactcgctgcgctcggtcgttcggctgcggcgagcggtatcagctc
actcaaaggcggtaatacggttatccacagaatcaggggataacgcagga
aagaacatgtgagcaaaaggccagcaaaaggccaggaaccgtaaaaaggc
cgcgttgctggcgtttttccataggctccgcccccctgacgagcatcaca
aaaatcgacgctcaagtcagaggtggcgaaacccgacaggactataaaga
taccaggcgtttccccctggaagctccctcgtgcgctctcctgttccgac
cctgccgcttaccggatacctgtccgcctttctcccttcgggaagcgtgg
cgctttctcatagctcacgctgtaggtatctcagttcggtgtaggtcgtt
cgctccaagctgggctgtgtgcacgaaccccccgttcagcccgaccgctg
cgccttatccggtaactatcgtcttgagtccaacccggtaagacacgact
tatcgccactggcagcagccactggtaacaggattagcagagcgaggtat
gtaggcggtgctacagagttcttgaagtggtggcctaactacggctacac
tagaagaacagtatttggtatctgcgctctgctgaagccagttaccttcg
gaaaaagagttggtagctcttgatccggcaaacaaaccaccgctggtagc
ggtggtttttttgtttgcaagcagcagattacgcgcagaaaaaaaggatc
tcaagaagatcctttgatcttttctacggggtctgacgctcagtggaacg
aaaactcacgttaagggattttggtcatgagattatcaaaaaggatcttc acctagatccttttaaattaaaaatgaagttttaaatcaatctaaagtat
atatgagtaaacttggtctgacagttaccaatgcttaatcagtgaggcac
ctatctcagcgatctgtctatttcgttcatccatagttgcctgactcccc
gtcgtgtagataactacgatacgggagggcttaccatctggccccagtgc
tgcaatgataccgcgagacccacgctcaccggctccagatttatcagcaa
taaaccagccagccggaagggccgagcgcagaagtggtcctgcaacttta
tccgcctccatccagtctattaattgttgccgggaagctagagtaagtag
ttcgccagttaatagtttgcgcaacgttgttgccattgctacaggcatcg
tggtgtcacgctcgtcgtttggtatggcttcattcagctccggttcccaa
cgatcaaggcgagttacatgatccccatgttgtgcaaaaaagcggttag
ctccttcggtcctccgatcgttgtcagaagtaagttggccgcagtgttat
cactcatggttatggcagcactgcataattctcttactgtcatgccatcc
gtaagatgcttttctgtgactggtgagtactcaaccaagtcattctgaga
atagtgtatgcggcgaccgagttgctcttgcccggcgtcaatacgggata
ataccgcgccacatagcagaactttaaaagtgctcatcattggaaaacgt
tcttcggggcgaaaactctcaaggatcttaccgctgttgagatccagttc
gatgtaacccactcgtgcacccaactgatcttcagcatcttttactttca
ccagcgtttctgggtgagcaaaaacaggaaggcaaaatgccgcaaaaaag
ggaataagggcgacacggaaatgttgaatactcatactcttcctttttca
atattattgaagcatttatcagggttattgtctcatgagcggatacatat
ttgaatgtatttagaaaaataaacaaatagggggttccgcgcacatttccc
cgaaaagtgccacctgacgcgccctgtagcggcgcattaagcgcggcggg
tgtggtggttacgcgcagcgtgaccgctacacttgccagcgccctagcgc
ccgctcctttcgctttcttcccttcctttctcgccacgttcgccggctt
ccccgtcaagctctaaatcggggctccctttagggttccgatttagtgc
tttacggcacctcgaccccaaaaaacttgattagggtgatggttcacgta
gtgggccatcgccctgatagacggtttttcgccctttgacgttggagtcc
acgttctttaatagtggactcttgttccaaactggaacaacactcaaccc
tatctcggtctattcttttgatttataagggattttgccgatttcggcct
attggttaaaaaatgagctgatttaacaaaaatttaacgcgaattttaac
aaaatattaacgcttacaatttgccattcgccattcaggctgcgcaactg
ttgggaagggcgatcggtgcgggcctcttcgctattacgccagcccaagc
taccatgataagtaagtaatattaaggtacgggaggtacttggagcggcc
gcaataaaatatctttattttcattacatctgtgtgttggttttttgtgt
gaatcgatagtactaacatacgctctccatcaaaacaaaacgaaacaaaa
caaactagcaaaataggctgtccccagtgcaagtgcaggtgccagaacat
ttctctatcgata.
```

The invention claimed is:

1. A nucleic acid sequence comprising the sequence of SEQ ID NO 1.

2. A nucleic acid sequence comprising the sequence of SEQ ID NO 2.

* * * * *